United States Patent [19]
Berliner et al.

[11] Patent Number: 5,925,774
[45] Date of Patent: Jul. 20, 1999

[54] ESTRENES FOR INDUCING HYPOTHALAMIC EFFECTS

[75] Inventors: David L. Berliner, Atherton, Calif.; Nathan W. Adams; Clive L. Jennings-White, both of Salt Lake City, Utah

[73] Assignee: Pherin Corporation, Menlo Park, Calif.

[21] Appl. No.: 08/460,133

[22] Filed: Jun. 1, 1995

Related U.S. Application Data

[60] Division of application No. 08/316,050, Sep. 29, 1994, abandoned, which is a continuation-in-part of application No. 08/127,980, Sep. 28, 1993, Pat. No. 5,783,571, which is a continuation-in-part of application No. 07/903,525, Jun. 24, 1992, abandoned, which is a continuation-in-part of application No. 07/707,862, May 31, 1991, abandoned, which is a continuation-in-part of application No. 07/638,743, Jan. 7, 1991, abandoned.

[51] Int. Cl.[6] ....................................................... C07J 3/00
[52] U.S. Cl. ............................................................ 552/611
[58] Field of Search ............................................... 552/611

[56] References Cited

PUBLICATIONS

Garcia–Velasco et al., "Nose Surgery and the Vomeronasal Organ", *Aesth. Plast. Surg.* 19:451–454, 1995.

Axel, "The Molecular Logic of Smell", *Scientific American*, Oct. 1995 pp. 154–159.

CA 53: 18985, RN 102471–98–7, 101863–76–7, 1967.

CA 97: 145109, RN 83059–92–1, 1967.

CA 79: 105459, RN 50394–23–5, 1967.

CA 87: 102517, RN 63779–91–9, 1967.

CA 80: 15104, RN 50865–75–3, 50704–61–5, 1967.

CA 79: 115762, RN 50686–66–3, 1967.

CA 76: 72701, RN 35456–74–7, 1967.

CA 90: 121877, RN 69283–69–8, 1967.

CAOLD, RN 103212–27–7, 1967.

RN 93998–04–0, 1967.

CA 70: 97046 Bascoul et al 1969.

CA 62: 789 Nakamura et al 1965.

*Primary Examiner*—Rebecca Cook
*Attorney, Agent, or Firm*—Heller Ehrman White & McAuliffe

[57] ABSTRACT

The invention relates to estrene steroids, which bind to neuroepithelial receptors. The steroid is preferably administered in the form of a pharmaceutical composition containing one or more pharmaceutically acceptable carriers.

14 Claims, 38 Drawing Sheets

ESTRENES FOR INDUCING HYPOTHALAMIC EFFECTS

CROSS-REFERENCE TO RELATED APPLICATIONS

This is a divisional of application Ser. No. 08/316,050, filed Sep. 29, 1994, abandoned. which is a continuation-in-part of Ser. No. 08/127,980 filed Sep. 28, 1993, now U.S. Pat. No. 5,783,571 which is a continuation-in-part of U.S. patent application Ser. No. 07/903,525, filed 24 Jun. 1991, abandoned, which in turn is a continuation-in-part of U.S. patent application Ser. No. 07/707,862, filed 31 May 1991, abandoned, which in turn is a continuation-in-part of U.S. patent application Ser. No. 07/638,743, filed 7 Jan. 1991 and now abandoned.

The application also relates to another continuation-in-part of U.S. patent application Ser. No. 07/903,525, U.S. patent application Ser. No. 08/077,140, filed 15 Jun. 1993, and to commonly assigned, co-pending U.S. patent application Ser. No. 07/903,604, filed 24 Jun. 1991, (a continuation-in-part of U.S. patent application Ser. No. 07/708,936, filed 31 May 1991, which in turn is a continuation-in-part of Ser. No. 07/638,185, filed 7 Jan. 1991 and now abandoned) entitled "Androstene Steroids as Neurochemical Initiators of Change in Human Hypothalamic Function and Related Pharmaceutical compositions and Methods"; and to the commonly assigned, co-pending continuation-in-part of Ser. No. 07/903,604, filed Jun. 24, 1992 U.S. patent application Ser. No. 08/077,359. The aforementioned U.S. patent applications are each incorporated herein by reference.

Finally, this application may relate to a copending U.S. Patent Application entitled "Fragrance Compositions Containing Human Pheromones", filed 24 Mar. 1992, U.S. Ser. No. 07/856,435.

BACKGROUND

1. Technical Field

This invention relates generally to novel compounds and methods for effectuating change in human hypothalamic function, thereby altering certain behavior and physiology mediated by the hypothalamus of individuals. More particularly, the invention relates to the use of certain Estrene steroids as neurochemical effectuators of physiology and behavior.

2. Description of the Related Art

The present invention relates to certain compounds, namely Estrene steroids and related compounds as will be described herein, and methods of using these compounds as human semiochemicals in order to alter hypothalamic function, thereby affecting certain consequent behavior and physiology, e.g. the reduction of anxiety. Estrene steroids are typified by 17β-Estradiol (1,3,5(10)-Estratriene-3,17β-diol), and are characterized by a phenolic 1,3,5(10) A-ring and a hydroxy or hydroxy derivative, such as an ether or ester, at the 3-position. The pheromone properties of some Estrene steroids for some mammalian species has been described. Michael, R. P. et al., *Nature* (1968) 218:746 refers to Estrogens (particularly Estradiol) as a pheromonal attractant of male rhesus monkeys. Parrot, R. F., *Hormones and Behavior* (1976) 7:207–215, reports Estradiol benzoate injection induces mating behavior in ovariectomized rats; and the role of the blood level of Estradiol in make sexual response (Phoenix, C. H., *Physiol. and Behavior* (1976) 16:305–310) and female sexual response (Phoenix, C. H., *Hormones and Behavior* (1977) 8:356–362) in Rhesus monkeys has been described. On the other hand, there is little agreement in the literature as to whether or not pheromones as such play any role in the reproductive 10 behavior and interpersonal communication of mammals (Beauchamp, G. K., et al., "The Pheromone Concept in Mammalian Chemical Communication: A Critique", In: *Mammalian Olfaction, Reproductive Processes, and Behavior,* Doty, R. L., Ed., Academic Press, 1976).

An embodiment of the subject invention concerns the non-systemic, nasal administration of certain Estrene steroids to affect a specific behavioral or physiological response in human subjects, e.g. a reduction of negative affect, mood, and character traits. In particular, nasal administration provides for contacting neuroreceptors of a heretofore poorly understood neuroendocrine structure, commonly known as the vomeronasal organ ("VNO"; also known as "Jacobson's organ"), with one or more steroid(s) or with compositions containing the steroid(s). This organ is accessed through the nostrils of most higher animals—from snakes to humans, and has been associated, inter alia, with pheromone reception in certain species (see generally Muller-Schwarze & Silverstein, *Chemical Signals,* Plenum Press, New York (1980)). The axons of the neuroepithelia of the vomeronasal organ, located supra palatial, form the vomeronasal nerve and have direct synaptic connection to the accessory olfactory bulb and indirect input from there to the corticomedial amygdaloid forebrain and hypothalamic nuclei of the brain. The distal axons of the terminal is nerve neurons may also serve as neurochemical receptors in the VNO. Stensaas, L. J., et al., *J. Steroid Biochem. and Molec. Biol.* (1991) 39:553.

This nerve has direct synaptic connection with the hypothalamus.

Johnson, A. et al. (*J. Otolaryngology* (1985) 14:71–79) report evidence for the presence of the vomeronasal organ in most adult humans, but conclude that the organ is probably non-functional. Contravening results which suggest that the VNO is a functional chemosensory receptor are reported by Stensaas, L., et al., supra; and by Moran, D. T., et al., Garcia-Velasco, J. and M. Mondragon; Monti-Bloch, L. and B. Grosser—all in *J. Steroid Biochem. and Molec. Biol.* (1991) 39.

It is apparent that it would be desirable to identify and synthesize human semiochemicals and pheromones and to develop pharmaceutical compositions and methods of use to influence hypothalamic function. This invention relates to the unexpected discovery that, when nasally administered to human subjects, certain neurochemical ligands, particularly certain Estrene steroids and related compounds, or pharmaceutical compositions containing certain Estrenes or related compounds, specifically bind to chemoreceptors of nasal neuroepithelial cells and this binding generates a series of neurolophysiological responses resulting in an alteration of hypothalamic function of an individual. When properly administered, the effect of certain of these compounds on the hypothalamus affects the function of the autonomic nervous system and a variety of behavioral or physiological phenomena which include, but are not limited to the following: anxiety, premenstrual stress, fear, aggression, hunger, blood pressure, and other behavioral and physiological functions normally regulated by the hypothalamus. Otto Appenzeller. The Autonomic Nervous System. An introduction of basic and clinical concepts (1990); Korner, P. I. Central nervous control of autonomic cardiovascular function, and Levy, N. M. and Martin, P. J. Neural control of the heart, both in Handbook of Physiology; Section 2: Cardiovascular System—the heart, Vol I, Washington D.C., 1979, American Physiological Society; Fishman, A. P., et al. editors, Handbook of Physiology. Section 3: Respiratory System. Vol. II. Control of breathing. Bethesda Md.. 1986. American Physiological Society.

In some instances a single Estrene steroid, or related compound, is administered, in some instances combinations of Estrene steroids and/or related compounds are administered.

SUMMARY OF THE INVENTION

Accordingly, it is an object of this invention to provide novel steroids which are human semiochemicals or pheromones and are suitable for nasal administration in an individual.

Additional objects, advantages and novel features of the invention will be set forth in part in the description which follows, and in part will become apparent to those skilled in the art upon examination of the following, or may be learned by practice of the invention.

Objects of this invention are achieved by steroids with the formula:

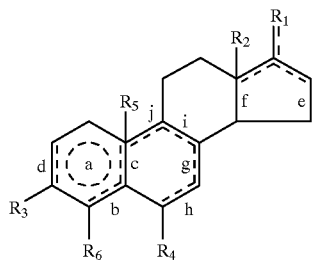

wherein $R_1$ is selected from the group consisting essentially of one or two hydrogen atoms, methyl, methylene, and one or two halo atoms; $R_2$ is absent or is selected from the group consisting essentially of hydrogen and methyl; $R_3$ is selected from the group consisting essentially of oxo, hydroxy, lower alkoxy, lower acyloxy, benzoyl, cypionyl, glucuronide and sulfonyl; $R_4$ is selected from the group consisting essentially of hydrogen, hydroxy, lower alkoxy, lower acyloxy, oxo and halo; $R_5$ is absent or is selected from the group consisting essentially of hydrogen, hydroxy, lower alkoxy and lower acyloxy; $R_6$ is a hydrogen or a halo; and "a" represents optional aromatic unsaturation of ring A of said steroid, or "b", "c", and "d" are each optional double bonds; and "e", "f", "g", "h", "i" and "j" are each optional double bonds. In this embodiment, the steroid is preferrably administered in the form of a pharmaceutical composition containing one or more pharmaceutically acceptable carriers; with the provisos that:

(I) when "a" is present, $R_3$ is hydroxy, and "j", "i", "g" and "h" are all absent, then (a) $R_4$ cannot be hydrogen; or (b) $R_4$ cannot be oxo if "e" and "f" are absent;

(II) when "a" is present, $R_3$ is hydroxy; and "j", "i" and "g" are all absent, "h" is present, then $R_1$ cannot be methylene;

(III) when "a", "h" and "i" are present, (a) then at least one of "e" or "f" is present, (b) $R_1$ is methylene, or (c) $R_1$ is not hydrogen.

(IV) when "b" is present, $R_3$ is oxo, "g", "h", "i", "j" are all absent, $R_5$ is hydrogen, (a) then $R_1$ cannot be one or two hydrogens if "f" is absent, or (b) if "f" is present $R_1$ cannot be methyl;

(V) when "b" and "J" are present and $R_3$ is oxo, hen at least one of "e" or "f" must be present or $R_1$ must be methylene;

(VI) when "c" is present, "d" is absent and $R_3$ is hydroxy, then (a) at least "e" or "f" must be present, or (b) $R_1$ must be methylene;

(VII) when "c" and "d" are present and $R_3$ is methoxy, then (a) at least "e" or "f" must be present or (b) $R_1$ must be methylene;

(VIII) when "b" is present, $R_3$ is hydroxy and $R_5$ is hydrogen, then (a) at least "e" or "f" must be present or (b) $R_1$ must be methylene.

A preferred class of compounds are those in which "a" is present and "g", "h" or "i" are optional double bonds. Another preferred class contains "b", "c" or "j" as a double bond. Yet another class contains "c" and "d" as double bonds. Still another class contains $R_2$ as methyl and "e" as a double bond.

The term lower alkyl, lower alkoxy, etc., encompasses carbon chains of 1 to 6 carbon atoms, preferrably 1 to 4 carbon atoms. Halo includes I, Br, F and Cl.

The steroids of the invention alter hypothalamic function and autonomic function in an individual. A ligand for a chemoreceptor displayed on the surface of a nasal neuroepithelial cell is provided wherein the cell is a part of tissue other than olfactory epithelia; and, the ligand is administered within a nasal passage of the individual such that the ligand binds specifically to the chemoreceptor, resulting in an alteration of hypothalamic function of the individual.

All embodiments of this application relate to and include the functional equivalents of the steroid structures disclosed in these embodiments and to those modified steroids which demonstrate said functional equivalence, whether or not the modified steroids are explicitly disclosed.

BRIEF DESCRIPTION OF THE DRAWINGS

FIG. 2B is a graphic comparison of the effect of an Estrene on the VNO receptor potential of male and female subjects.

A=1, 3, 5(10),16-Estratetraen-3-yl acetate
B=Androsta-4,16-dien-3-one
C=1,3,5(10),16-Estratetraen-3-ol
D=3-Methoxy-Estra-1,3,5(10),16-tetraene
E=Androsta-4,16-dien-3α-ol
F=Androsta-4,16-dien-3β-ol

G=Androst-4-en-3-one
H=Androsta-4,16-diene-3,6-dione
J=10,17-Dimethylgona-4,13(17)-dien-3-one
K=1,3,5(10),16-Estratetraen-3-ol-methyl ether
L=1,3,5(10),16-Estratetraen-3-yl-propionate
EVG=Electro-vomeronasogram
GSR=Galvanic Skin Response
=Electrodermal Activity (EDA)
ST=Skin Temperature

M=1,3,5(10)-Estratrien-3-ol

Figure 10:
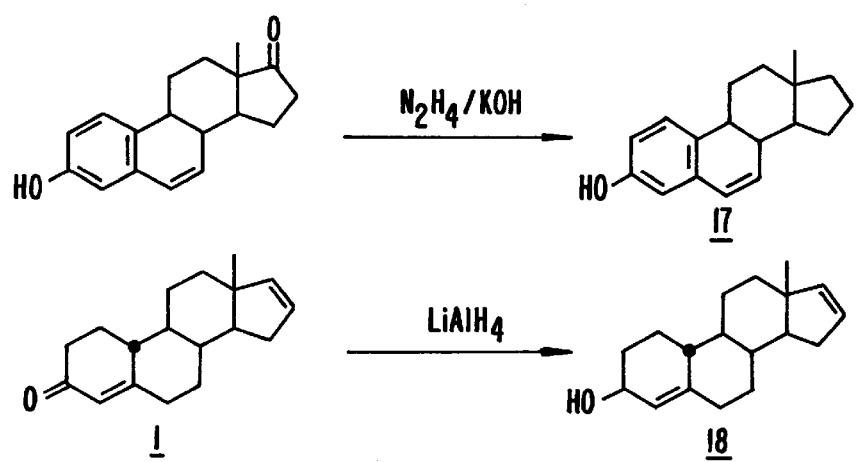

FIG. 10 depicts the synthesis of Estra-1,3,5(10),6-tetraen-3-ol and Estra-4,16-dien-3-ol.

Figure 11:
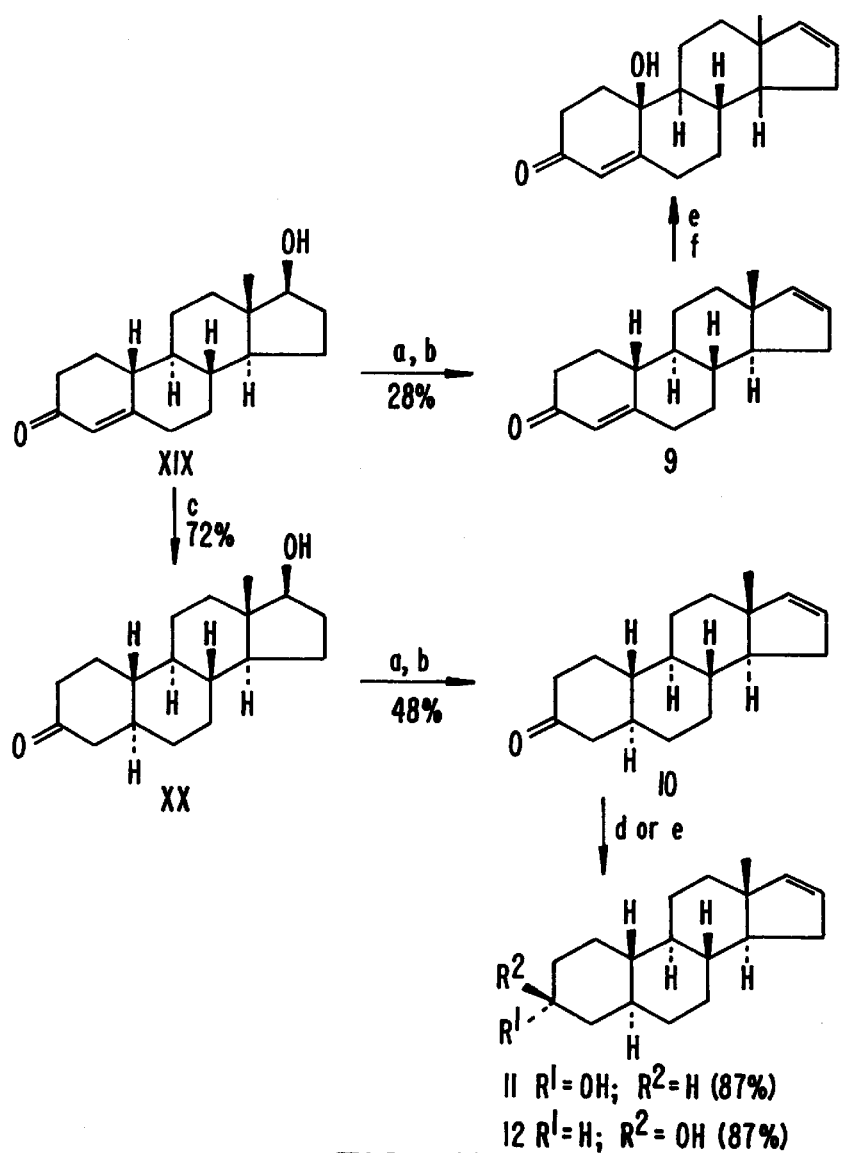

FIG. 11 depicts the synthesis of compounds described in Examples 16 through 19.

Figure 12:
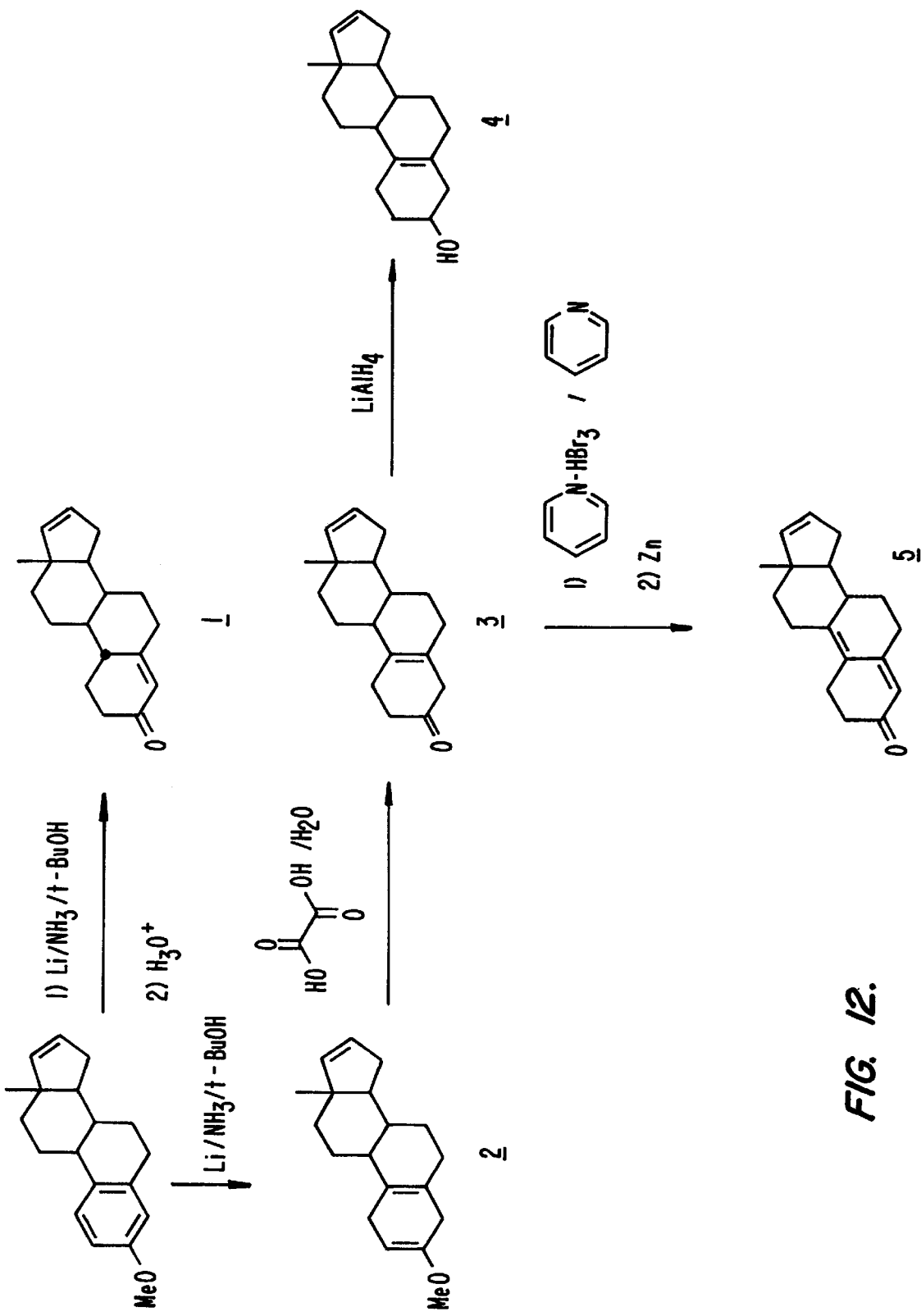

FIG. 12 illustrates the steps of synthesis described in Examples 20 through 24.

Figure 13:
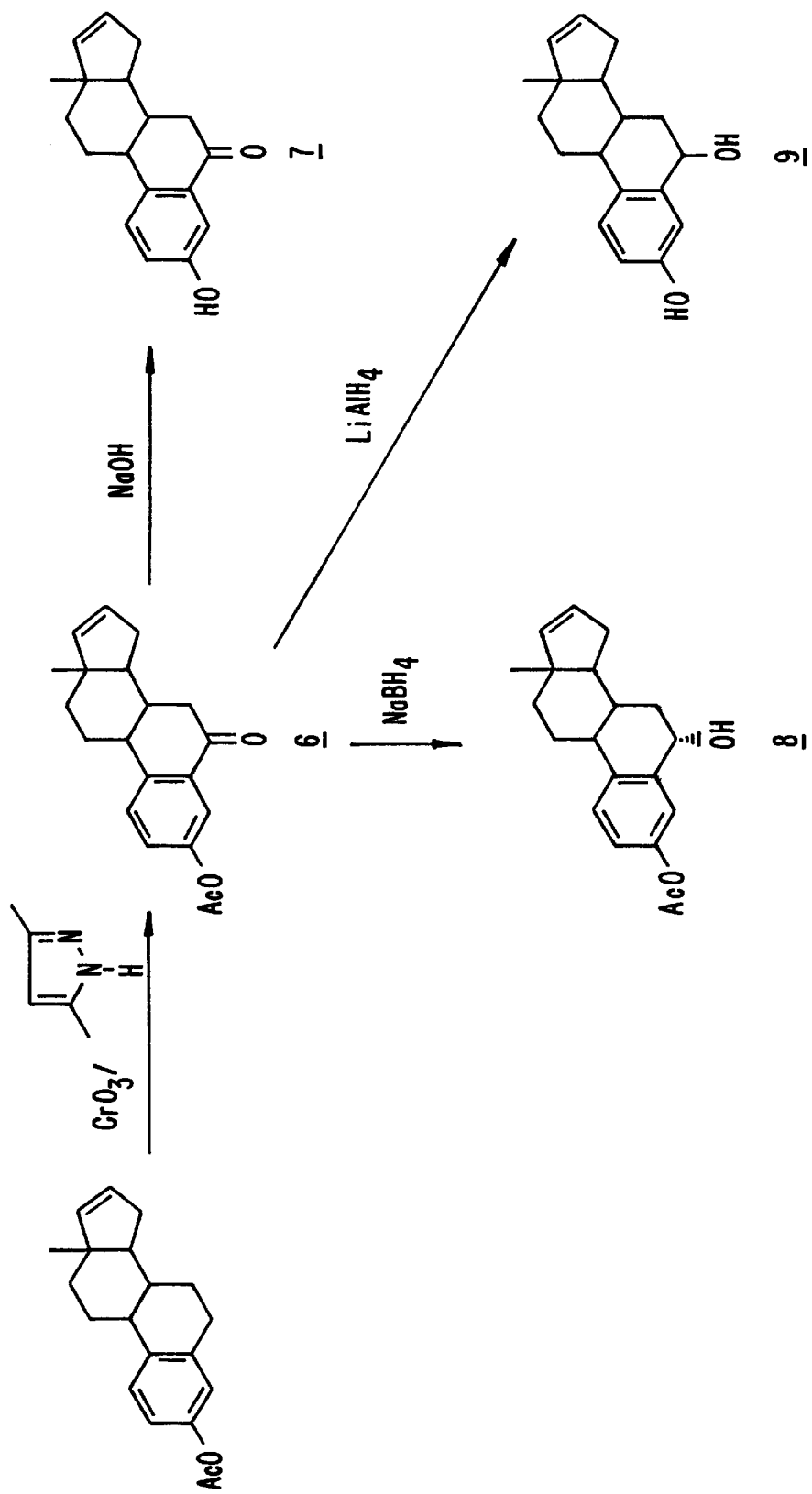

FIG. 13 illustrates the steps of synthesis described in Examples 25 through 28.

Figure 14:
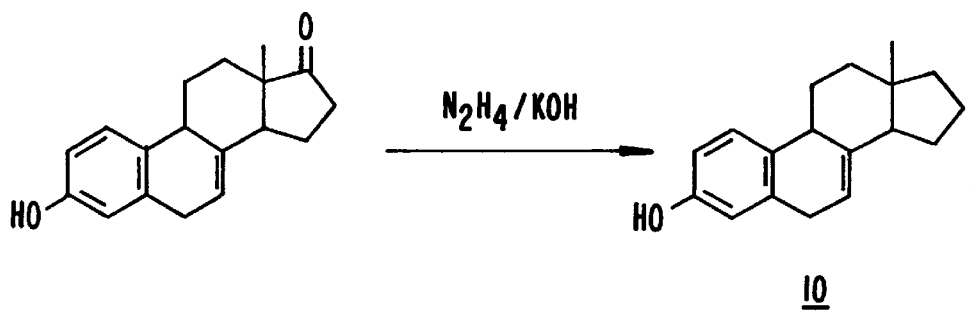
Figure 14:
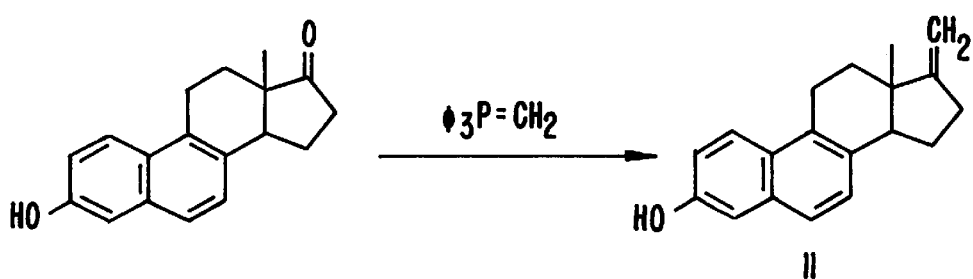

FIG. 14 illustrates the steps of synthesis described in Examples 29 through 30.

Figure 15:
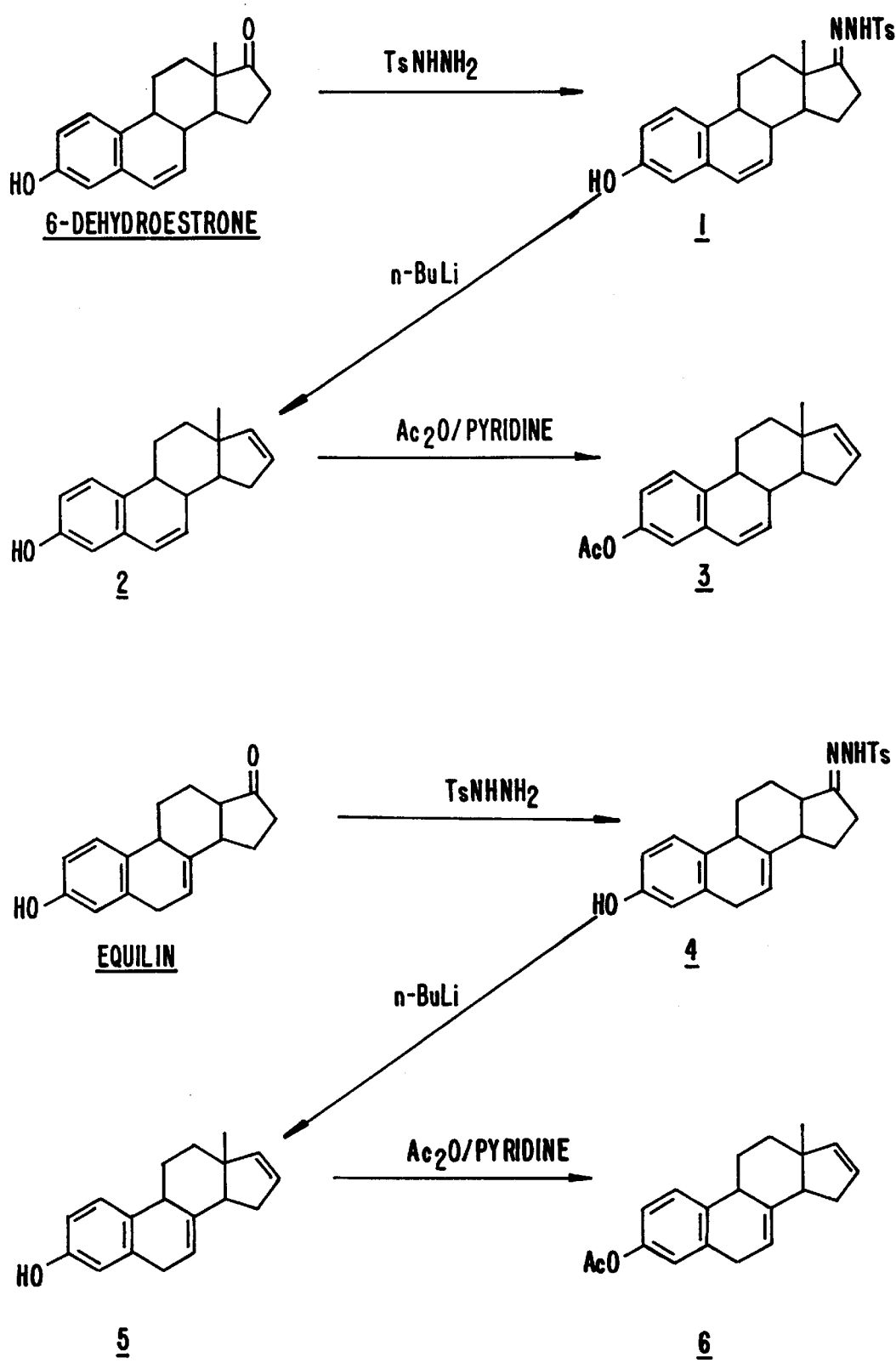

FIG. 15 illustrates the steps of synthesis described in Examples 31 through 36.

Figure 16:
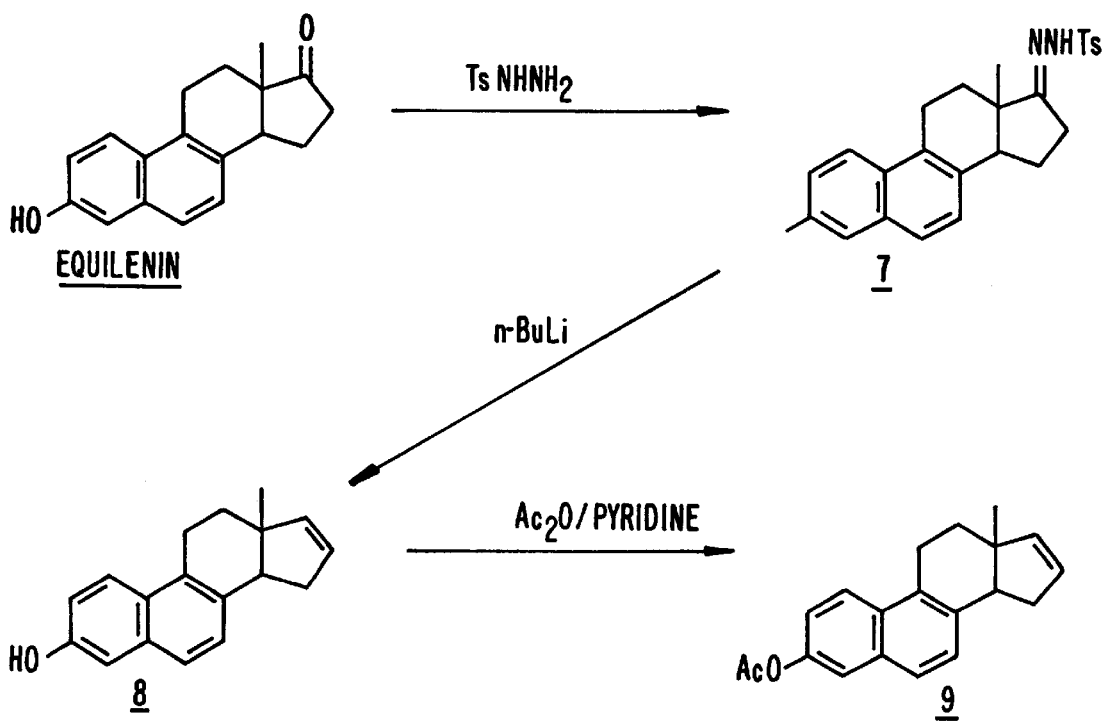

FIG. 16 illustrates the steps of synthesis described in Examples 37 through 39.

Figure 17:
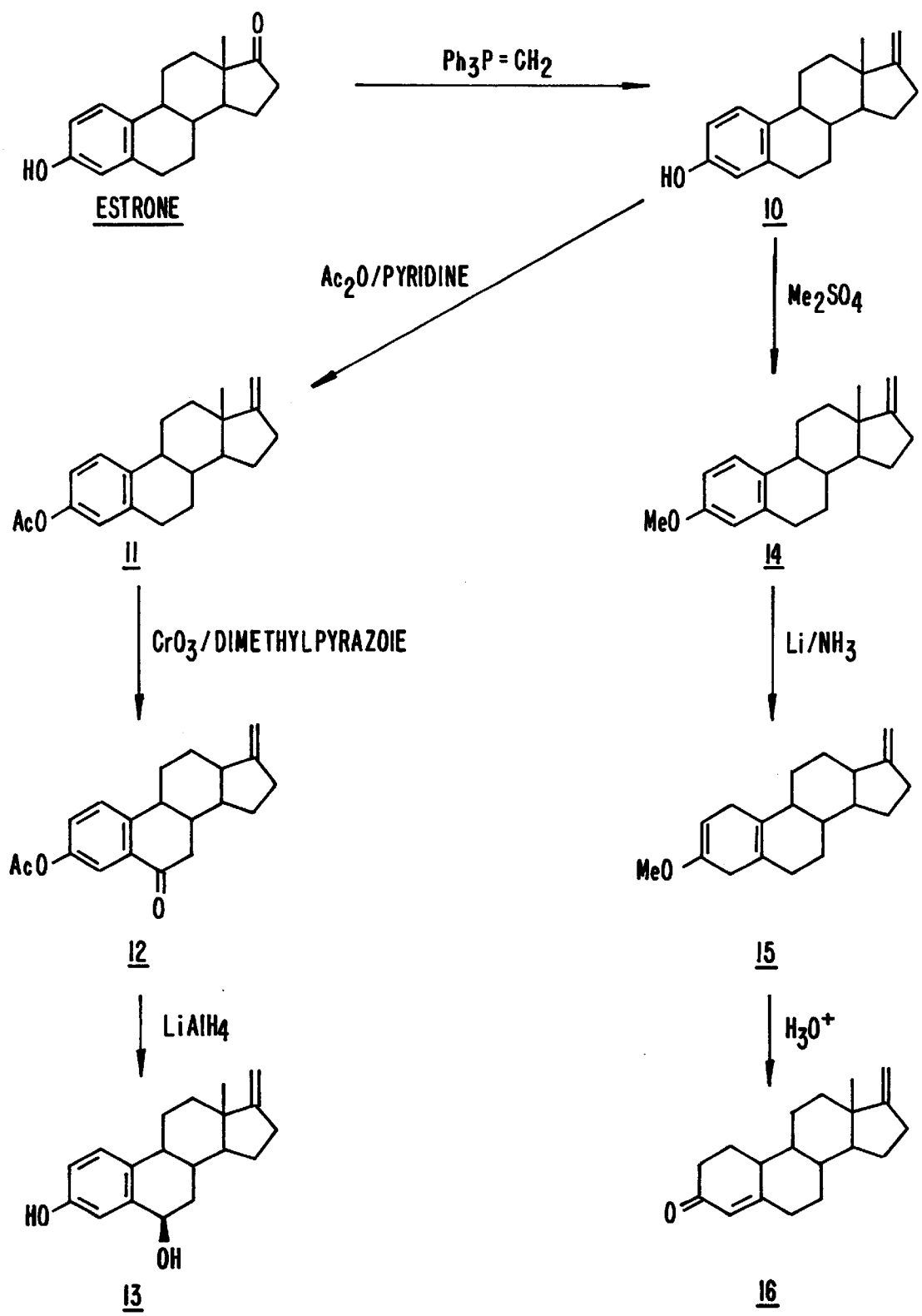

FIG. 17 illustrates the steps of synthesis described in Examples 40 through 46.

Figure 18:
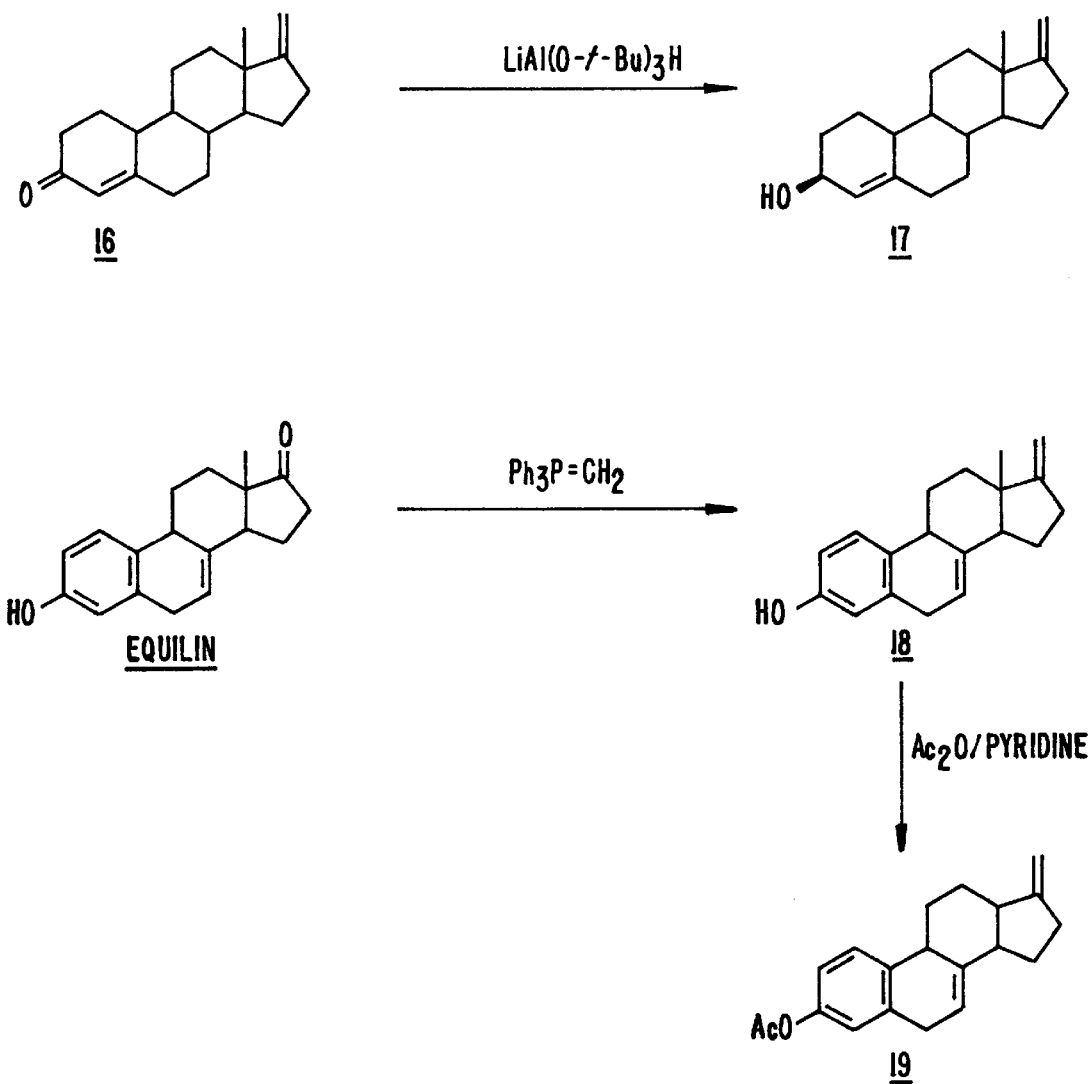

FIG. 18 illustrates the steps of synthesis described in Examples 47 through 49.

Figure 19:
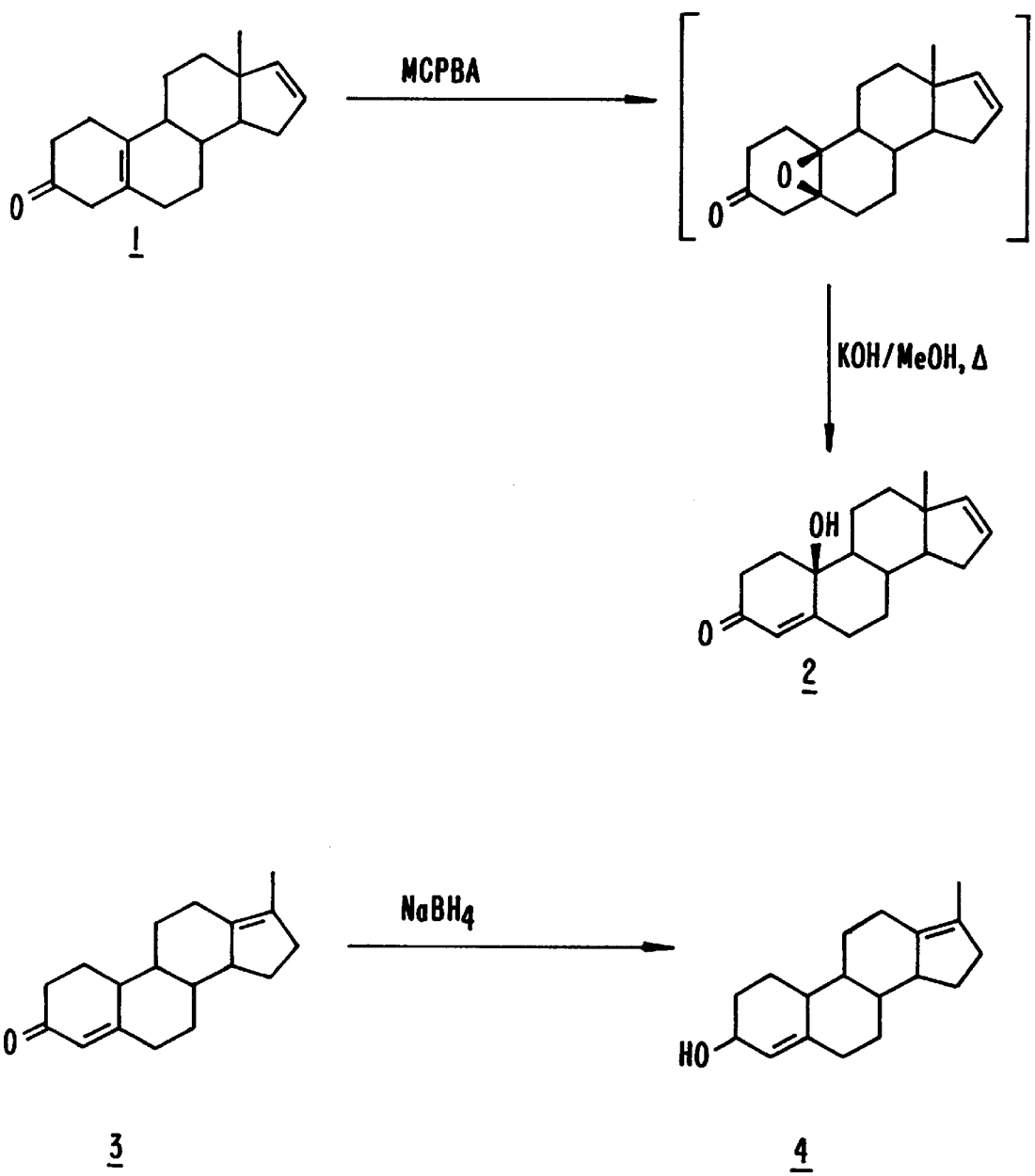

FIG. 19 illustrates the steps of synthesis described in Examples 50 through 51.

Figure 20A:
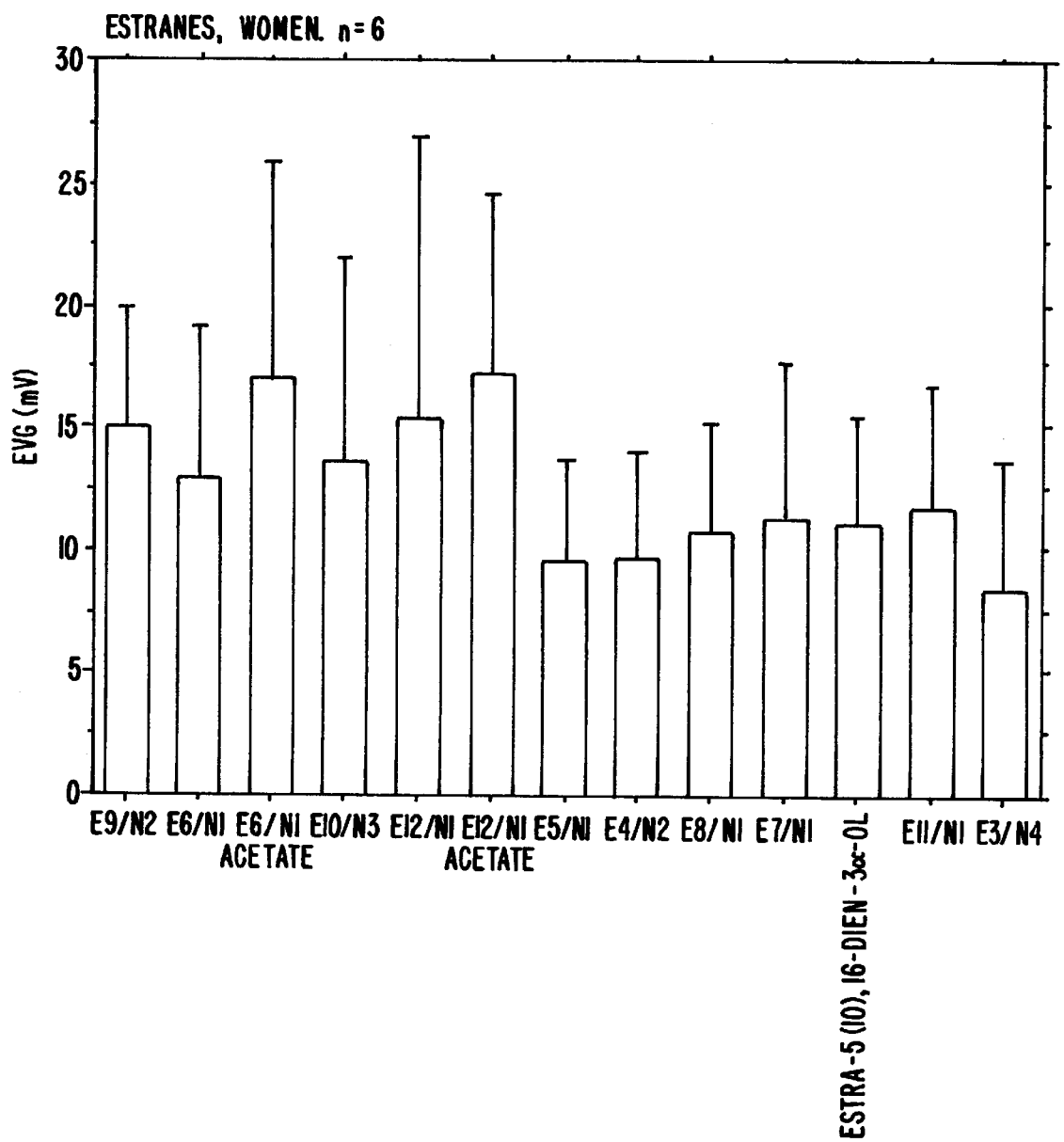
Figure 20B:
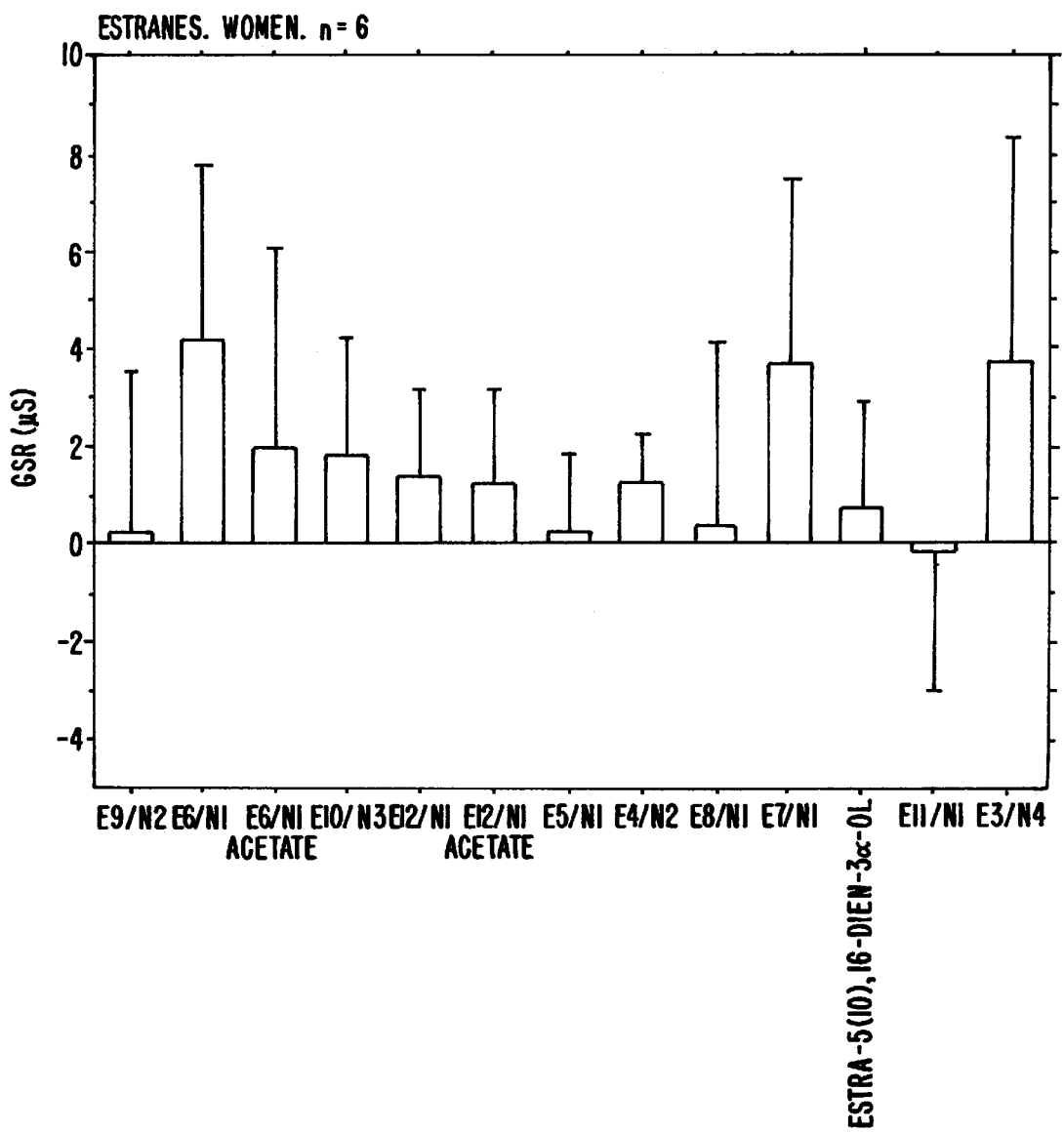
Figure 20C:
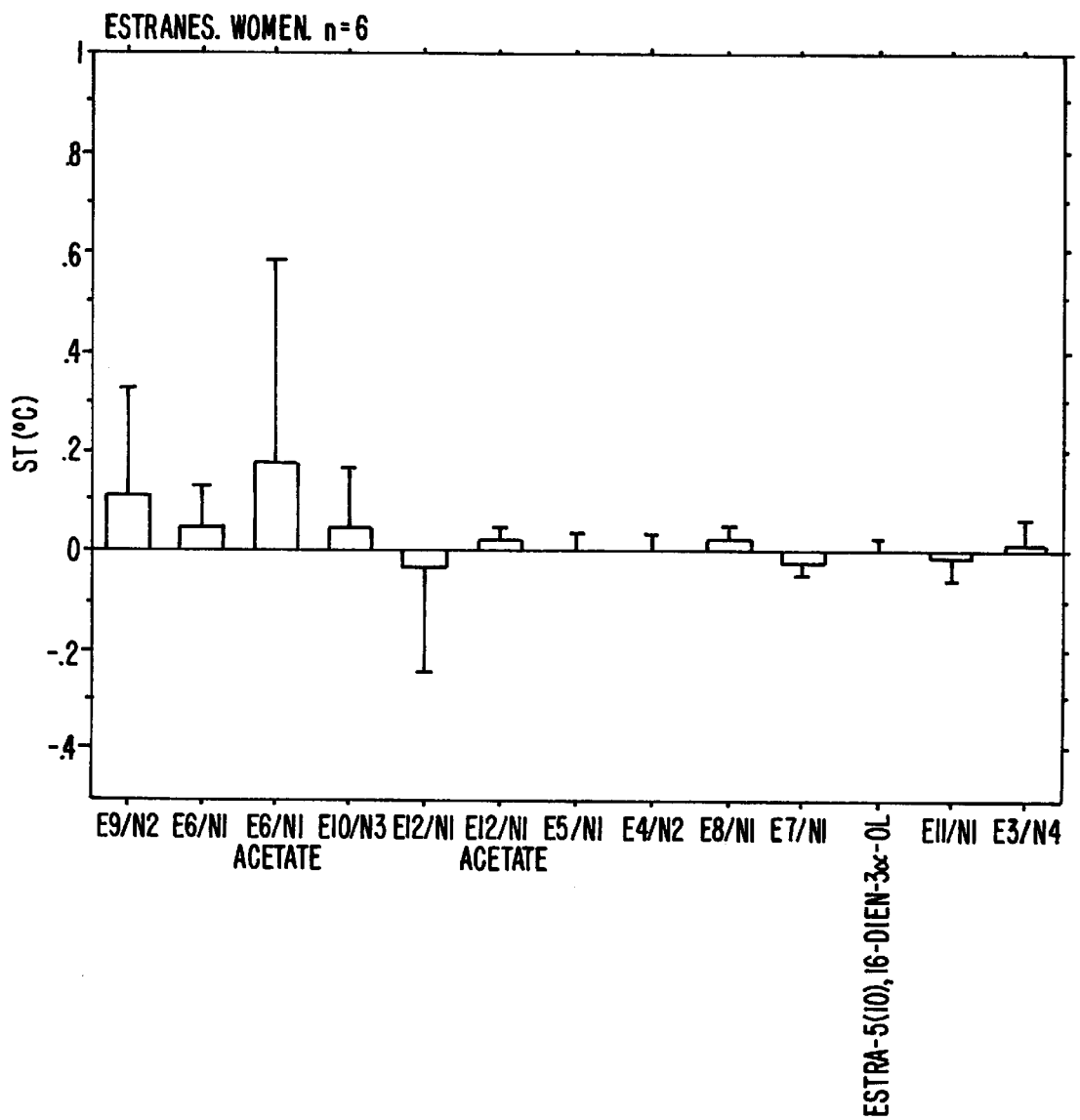

FIGS. 20A, 20B and 20C illustrate the EVG, SR and ST data on women, respectively, for 13 estranes on Chart 1.

Figure 21A:
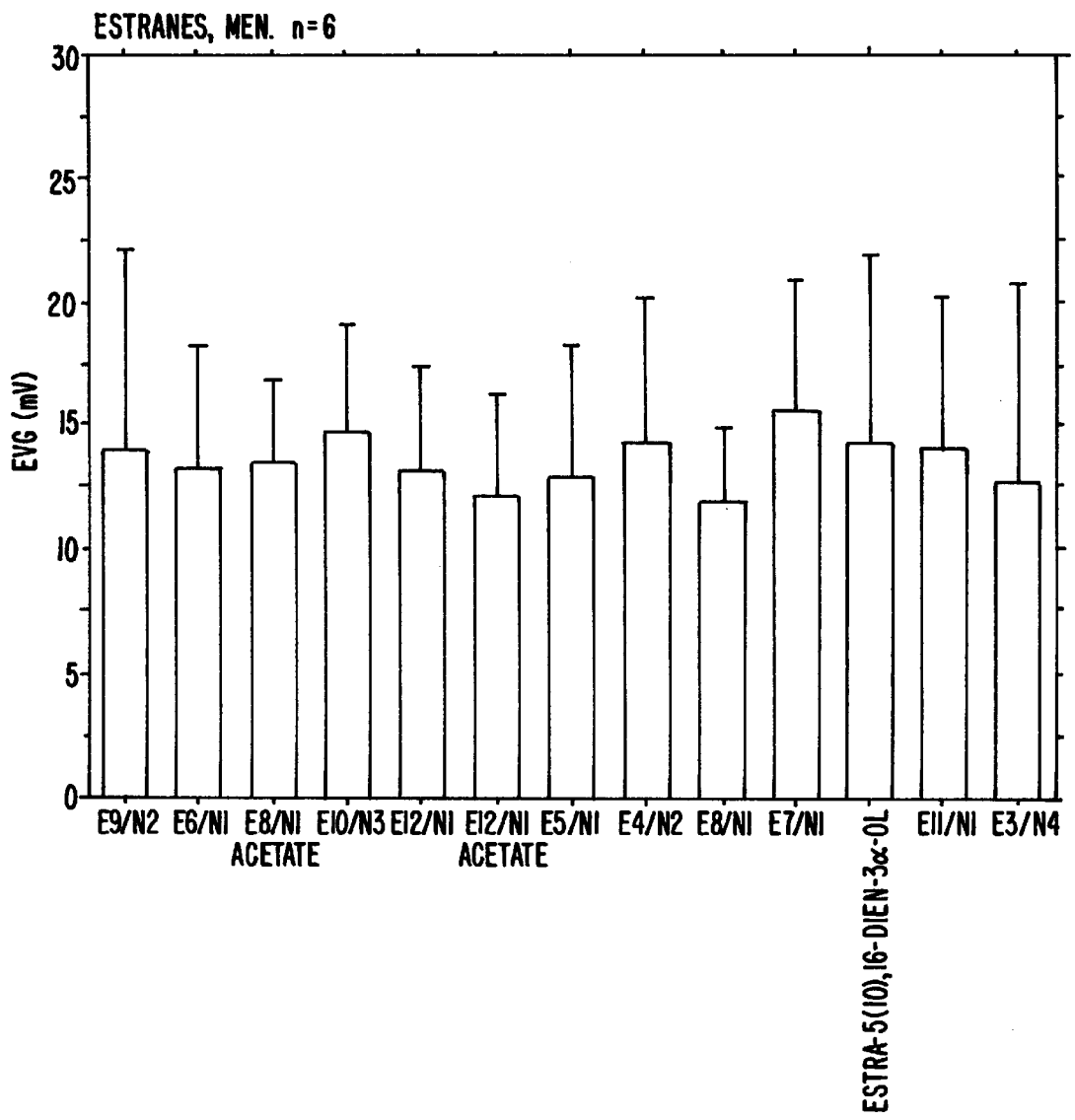
Figure 21B:
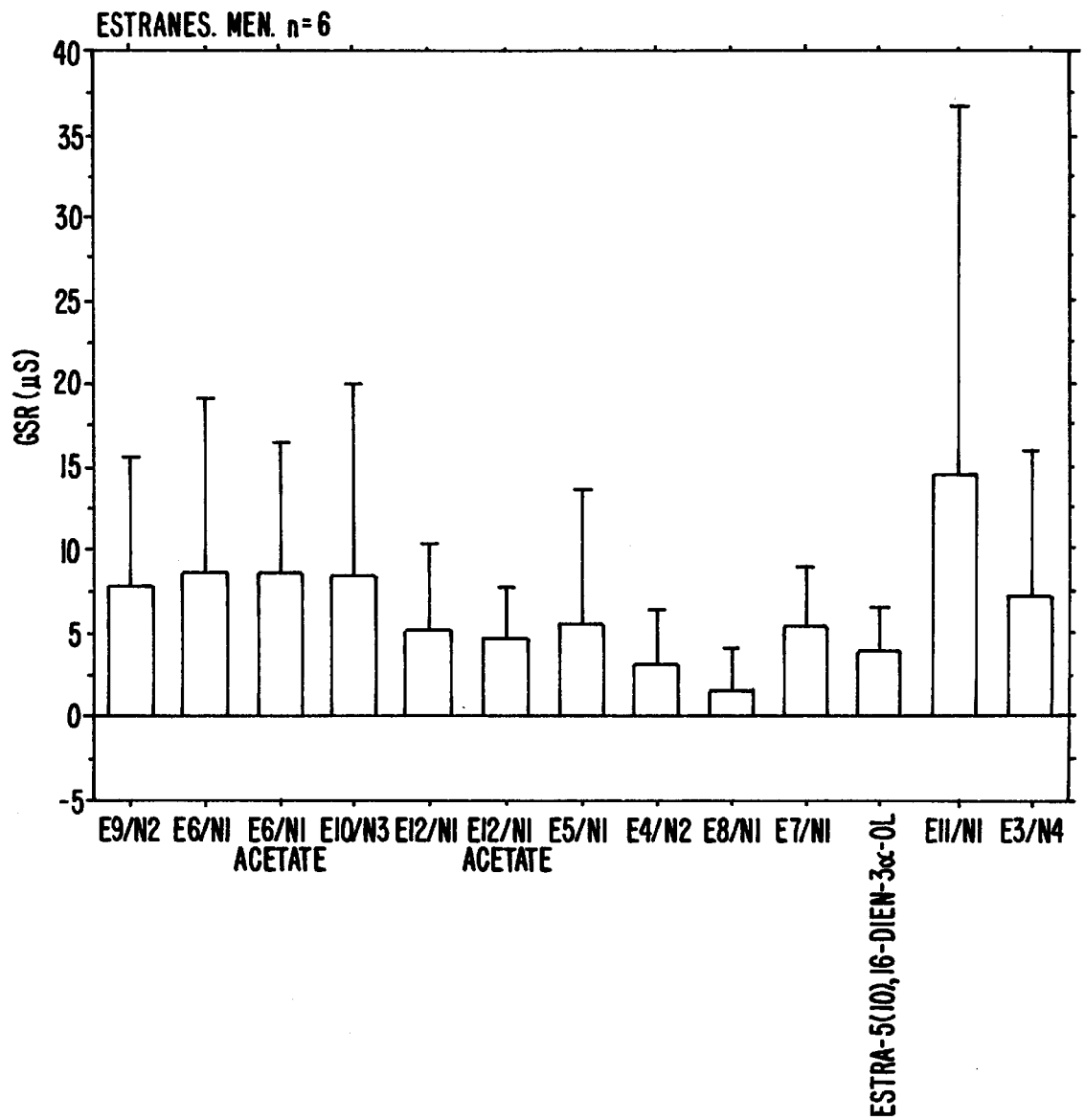
Figure 21C:
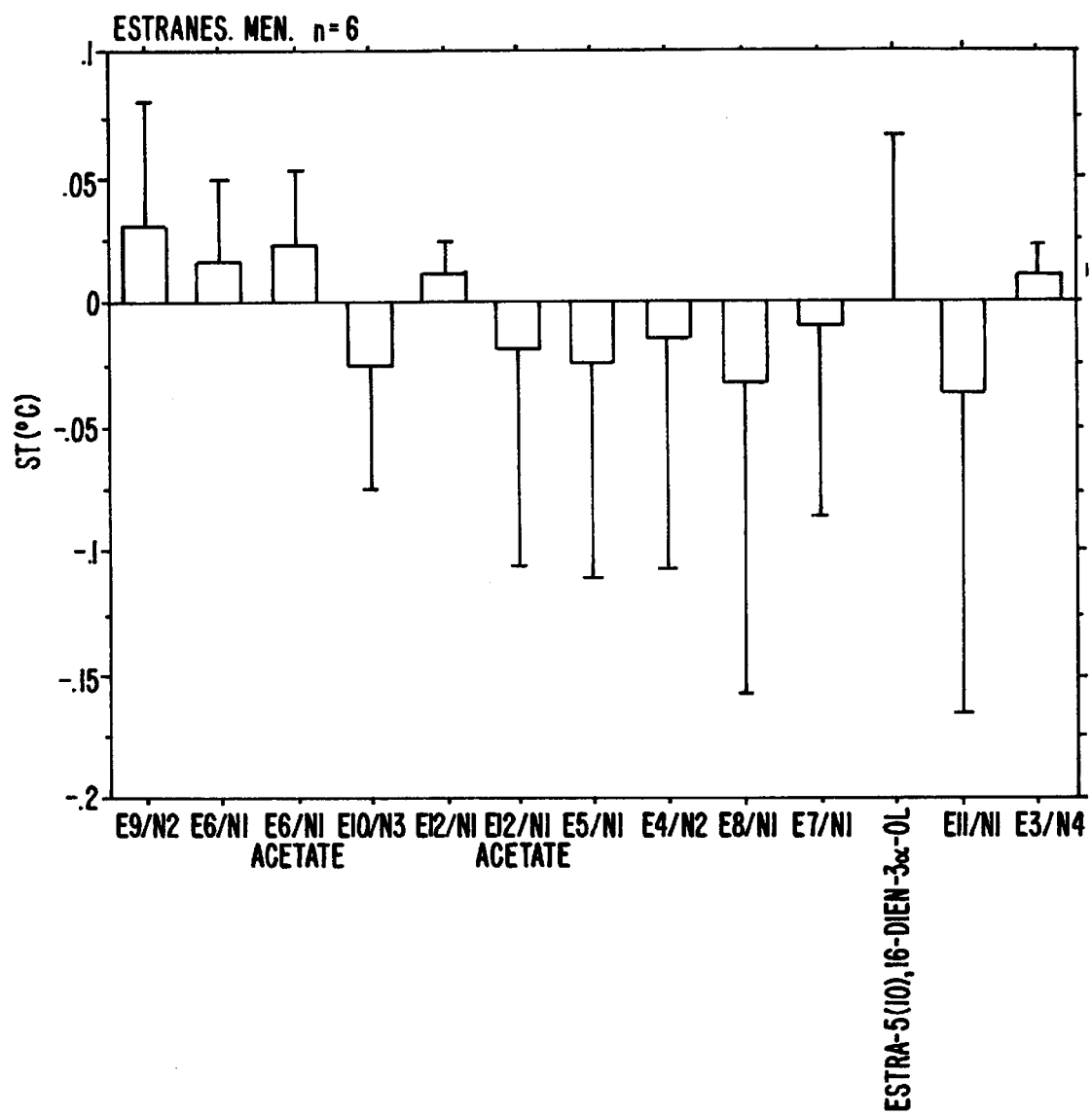

FIGS. 21A, 21B and 21C illustrate the EVG, GSR and ST data on men, respectively, for 13 estranes on Chart 1.

Figure 22A:
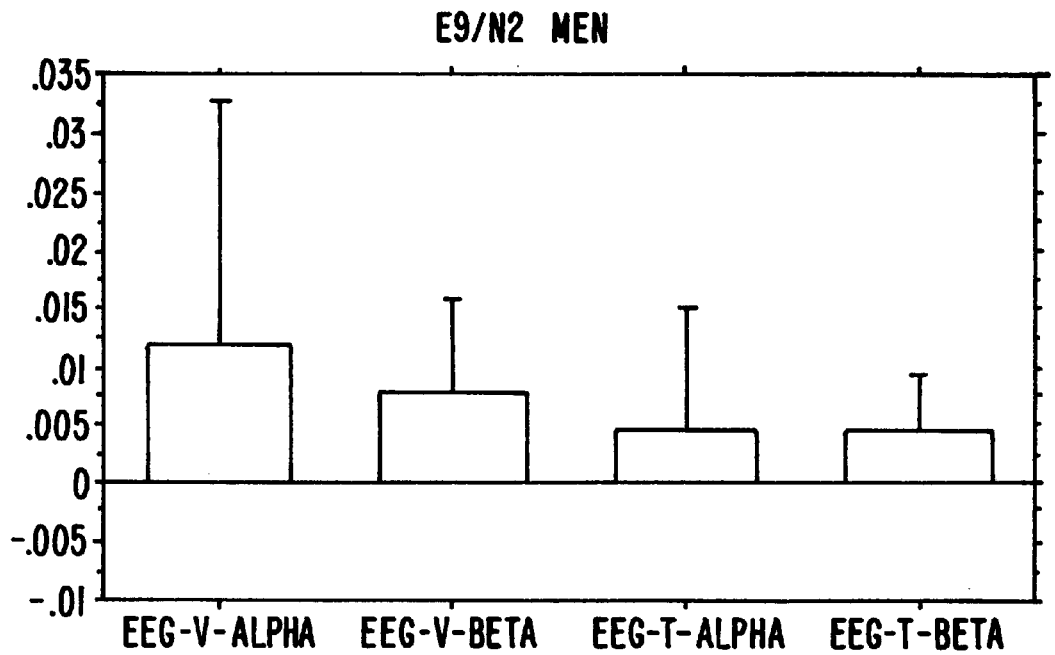
Figure 22B:
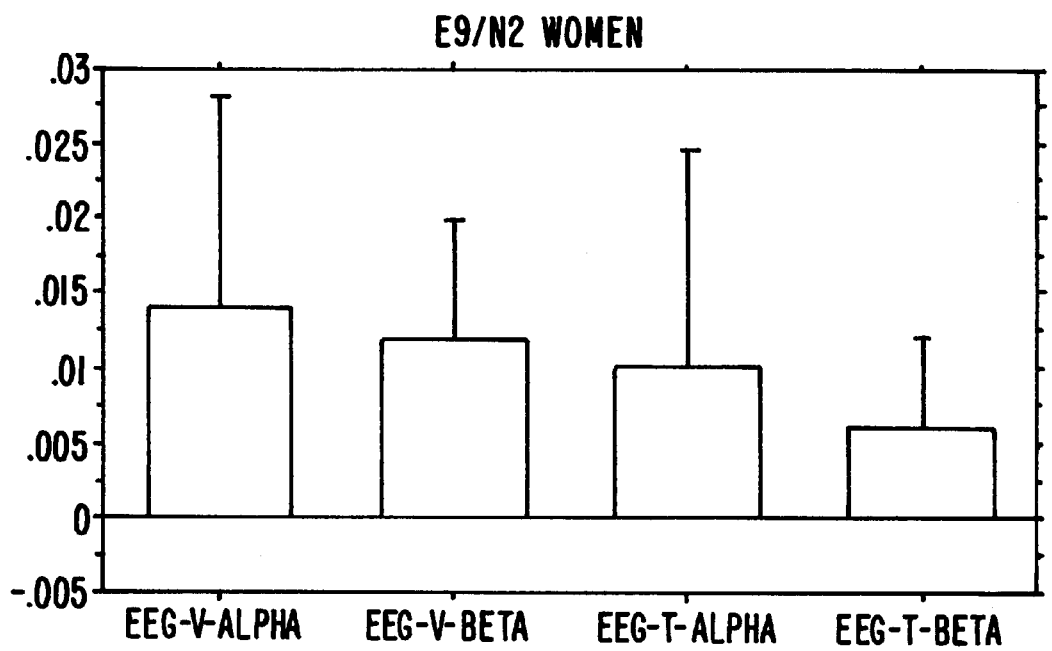
Figure 23A:
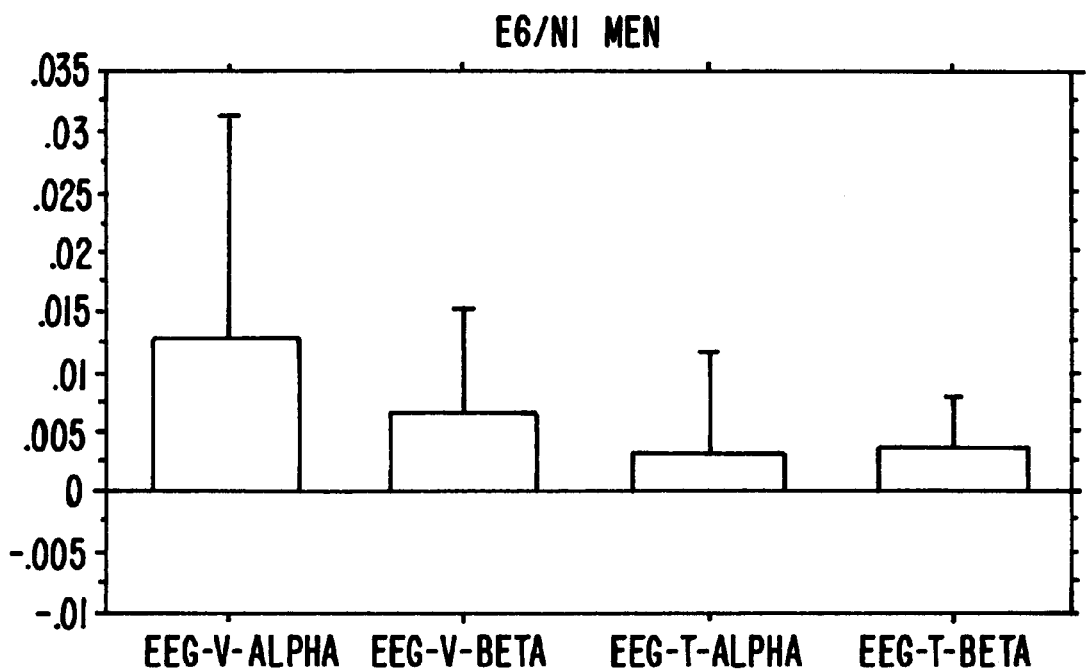
Figure 23B:
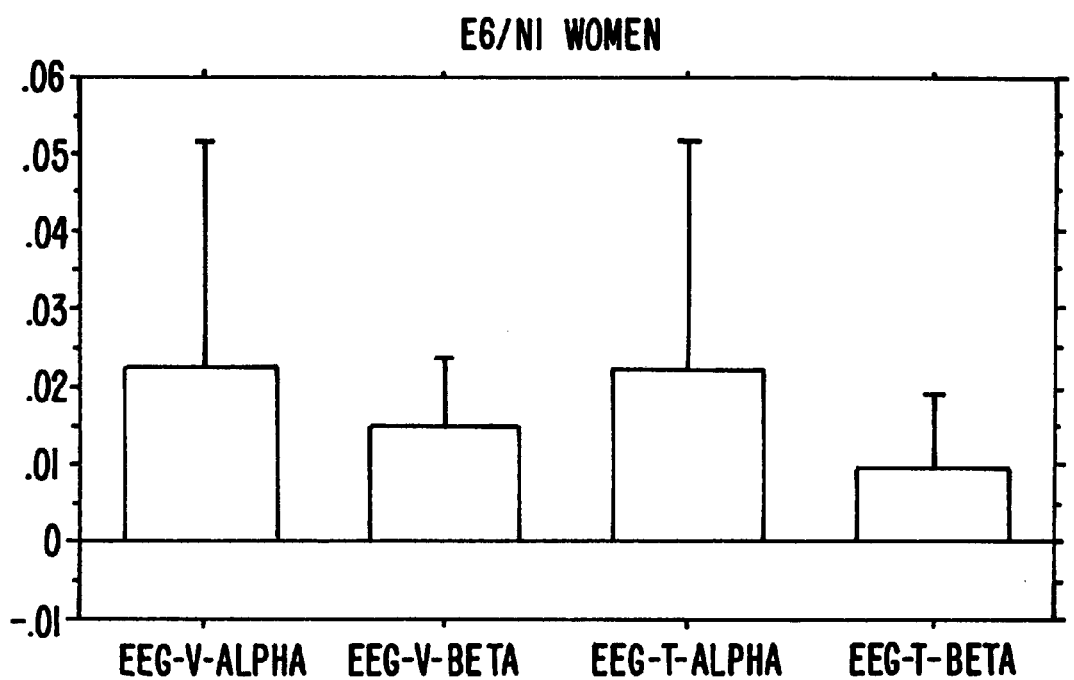
Figure 24A:
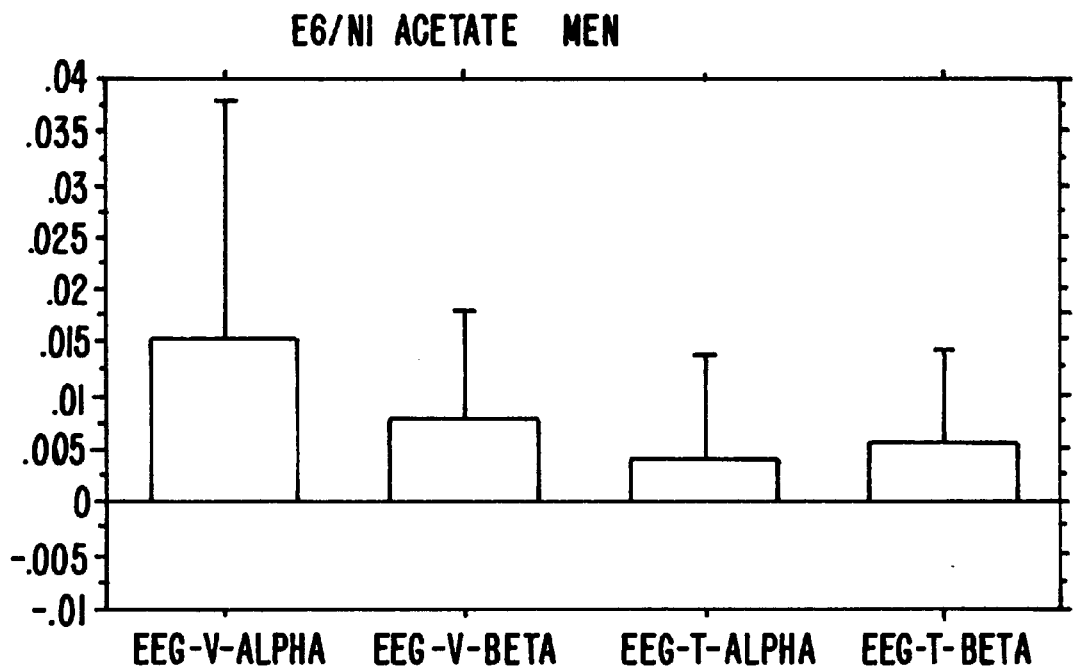
Figure 24B:
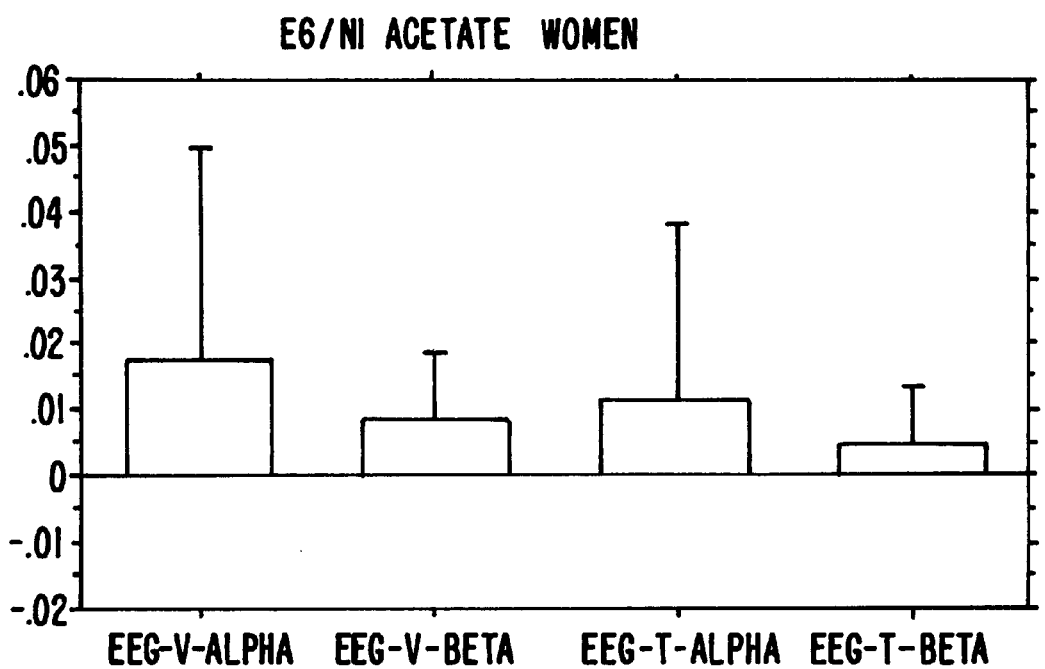
Figure 25A:
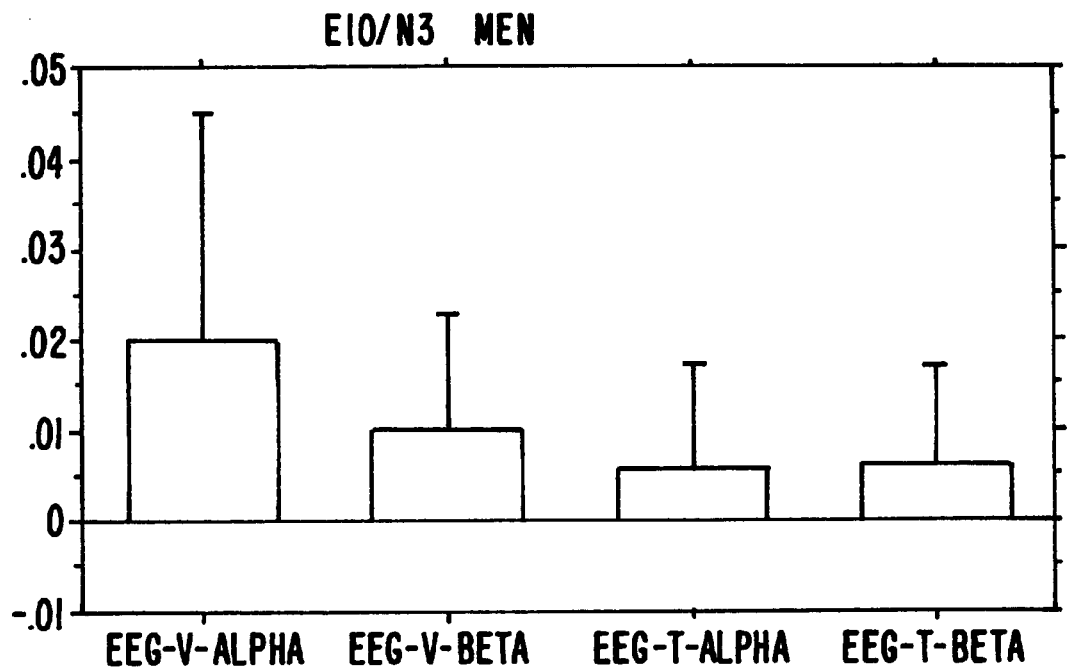
Figure 25B:
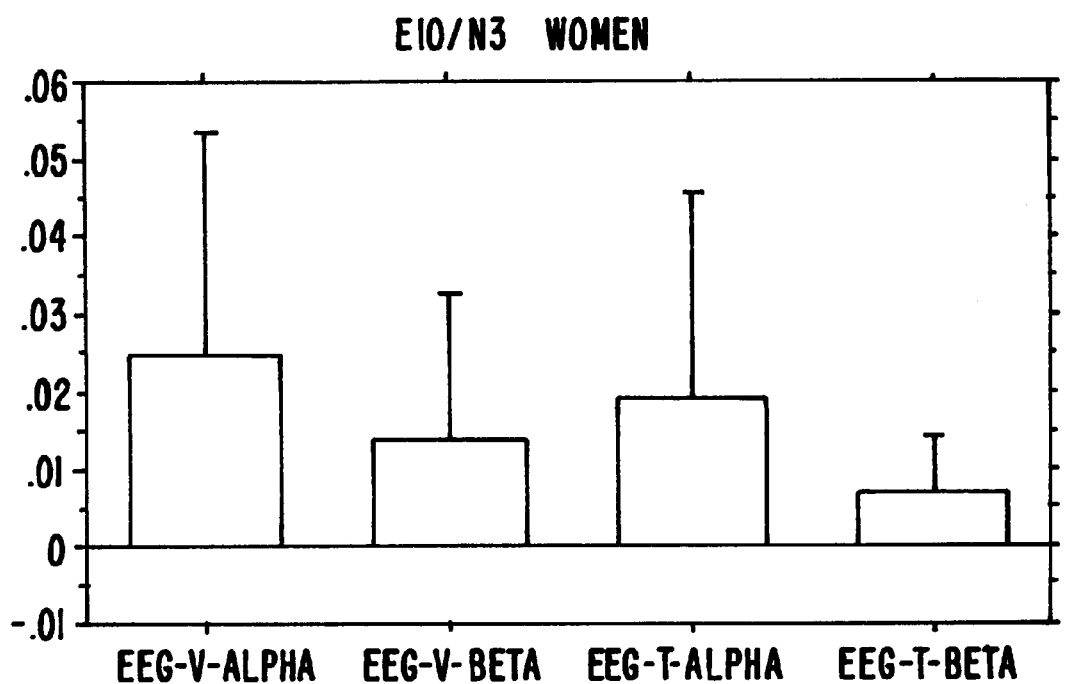
Figure 26A:
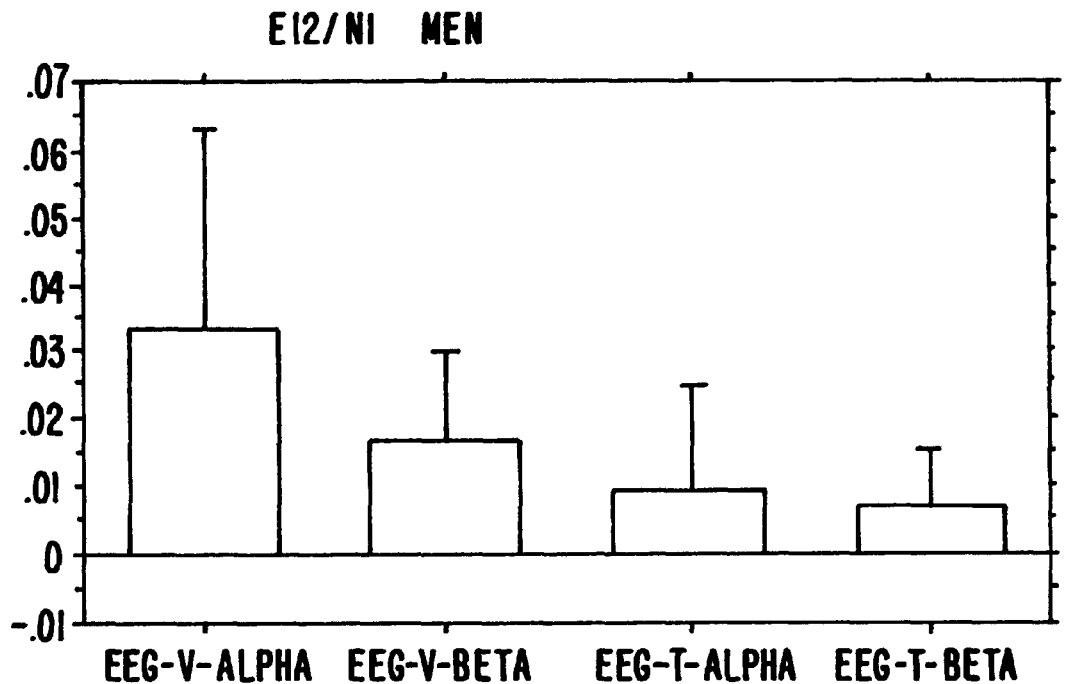
Figure 26B:
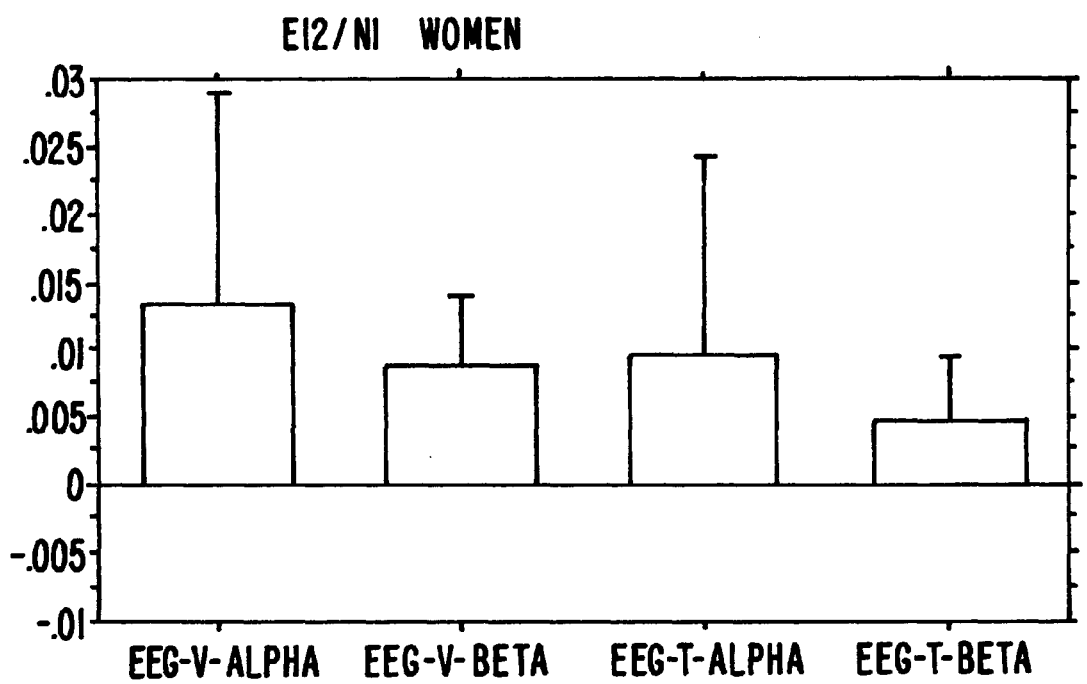
Figure 27A:
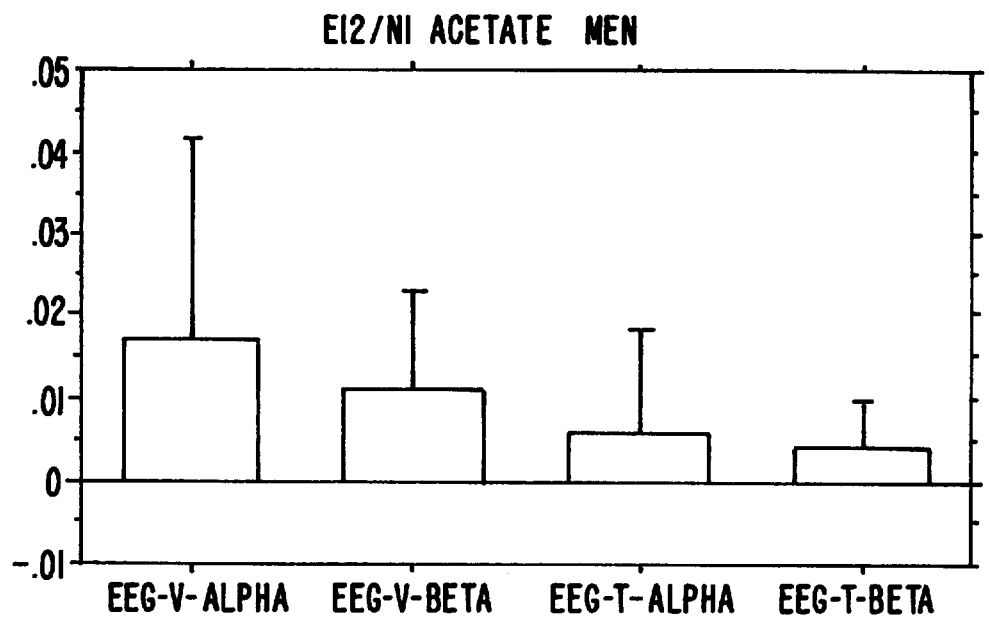
Figure 27B:
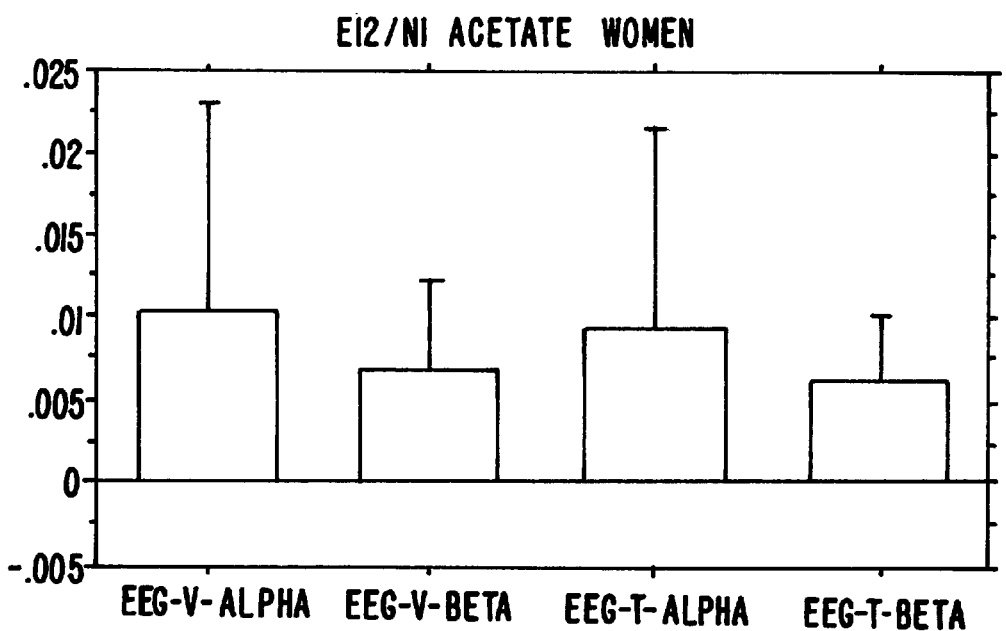
Figure 28A:
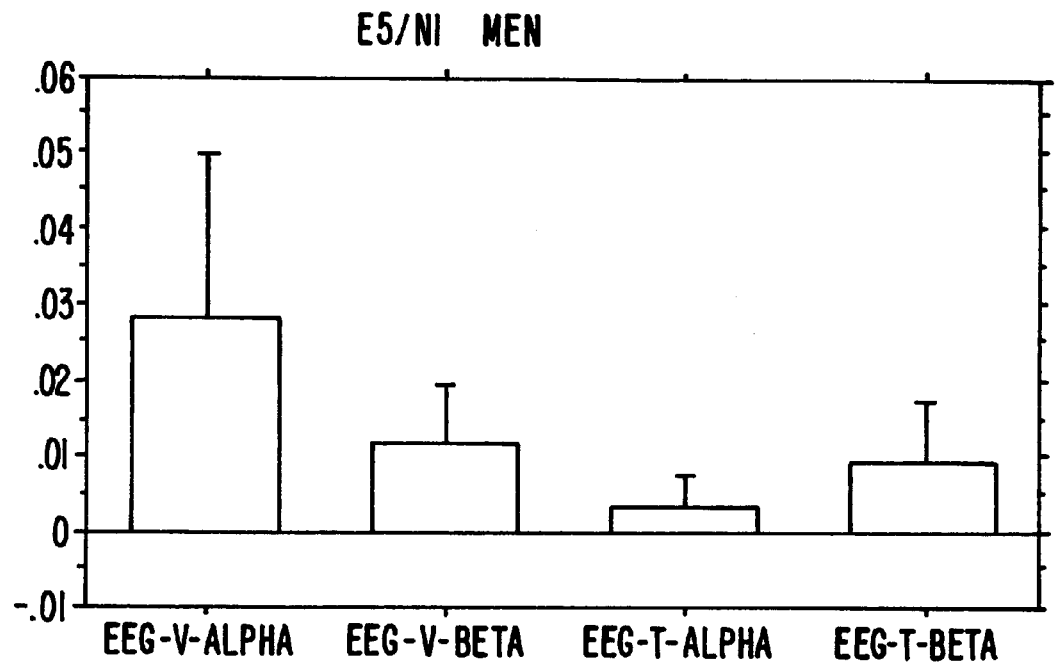
Figure 28B:
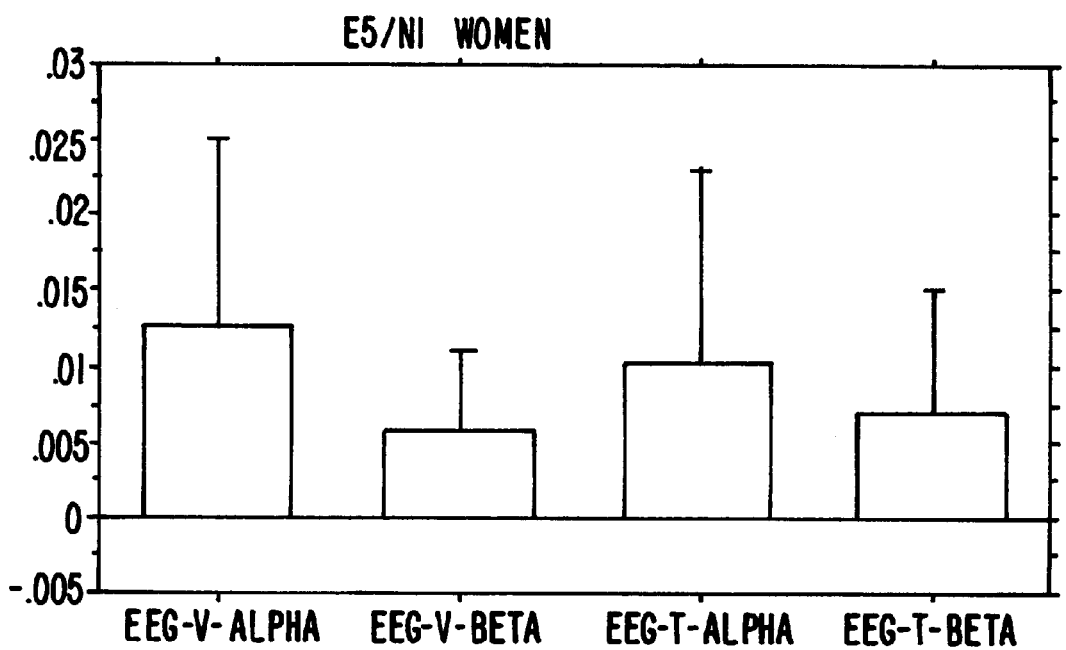
Figure 29A:
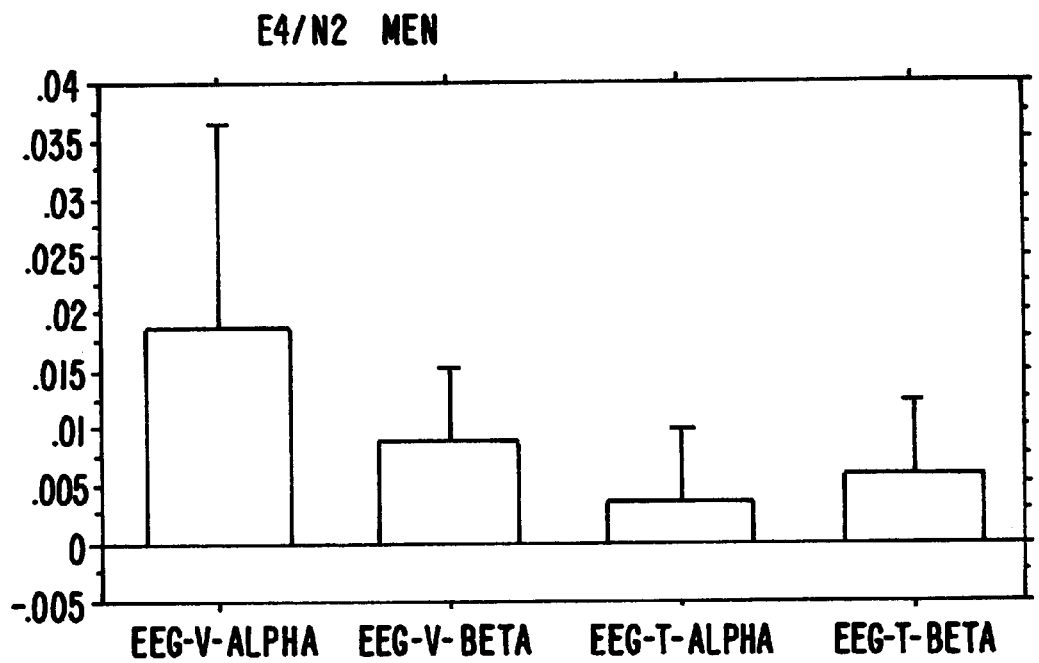
Figure 29B:
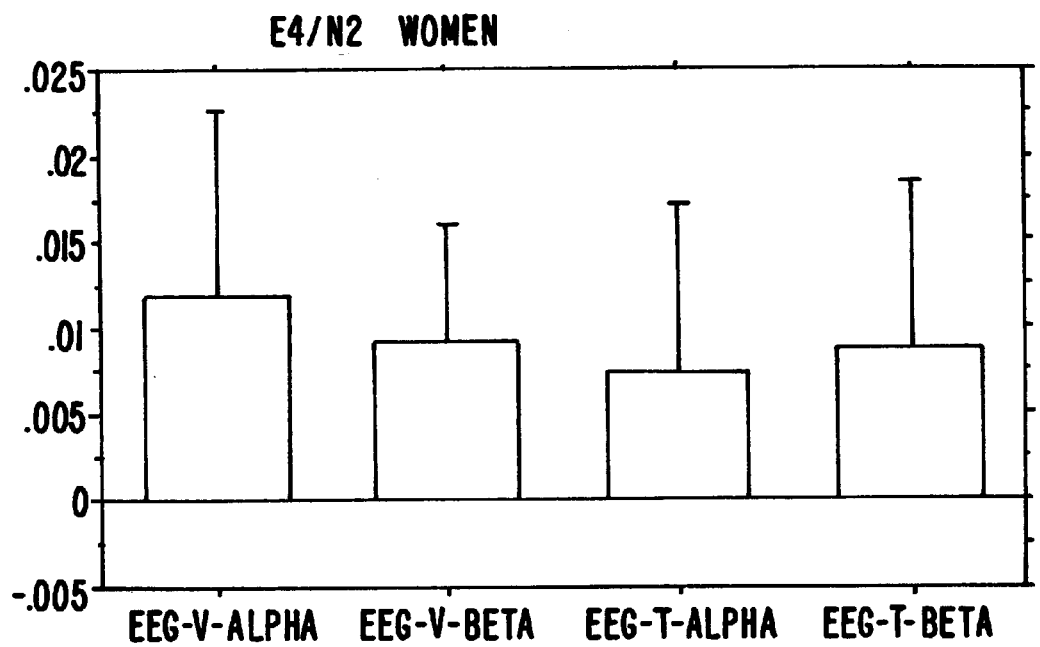
Figure 30A:
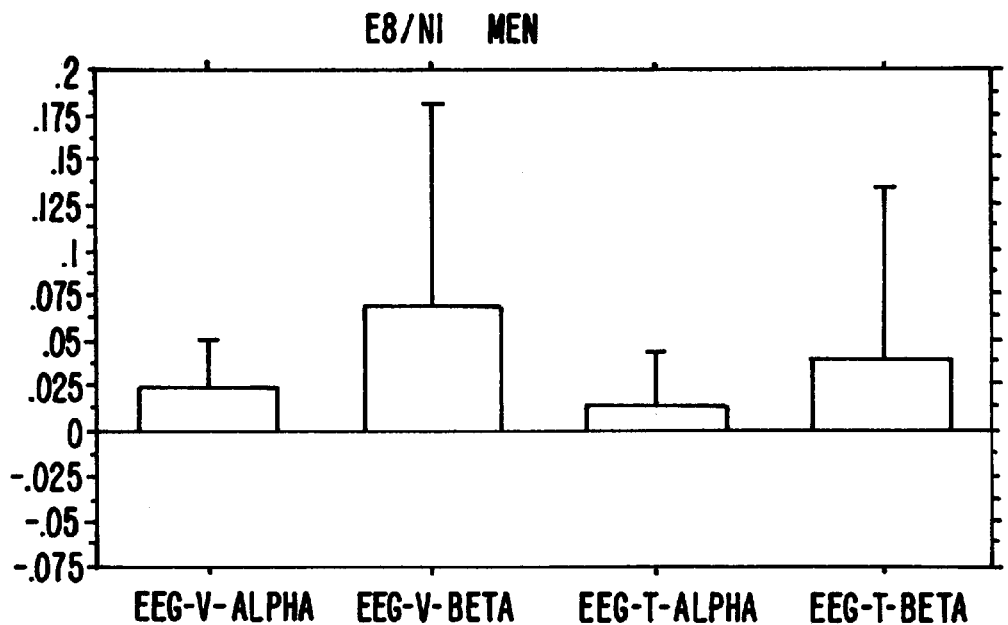
Figure 30B:
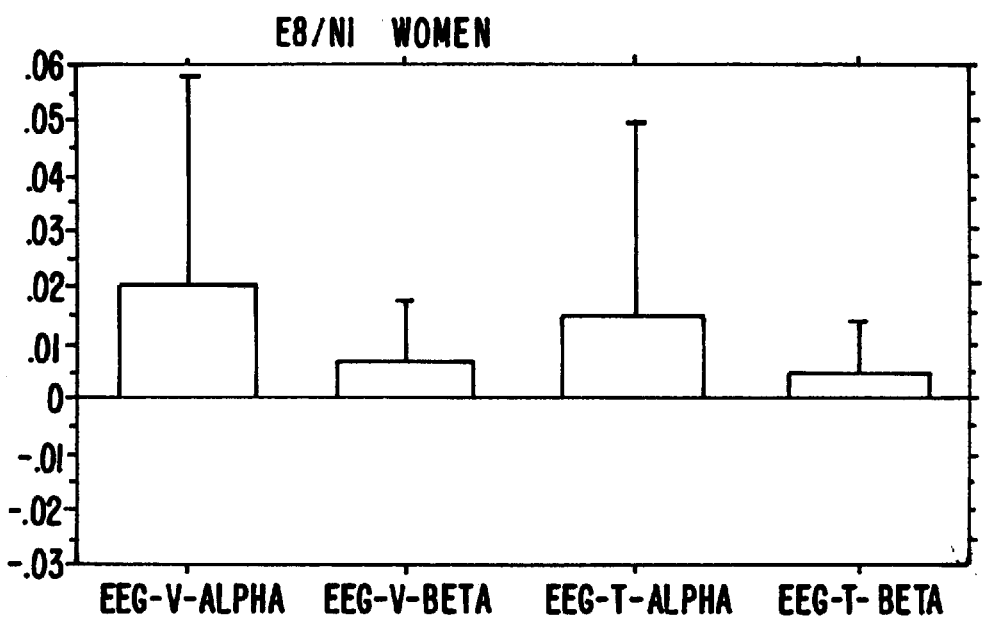

FIGS. 22A and B through 34A and B illustrate the EEG data on men (A) and women (B) for the 13 estranes, respectively, identified in FIG. 20.

DETAILED DESCRIPTION OF THE INVENTION

I. Definitions

An "affect" is a transient feeling state. Typical negative affects are feelings of nervousness, tenseness, shame, anxiousness, irritability, anger, rage, and the like. "Moods" are longer lasting feeling states such as guilt, sadness, hopelessness, worthlessness, remorsefulness, misery, unhappiness and the like. "Character" traits are more permanent aspects of an individual's personality. Typical negative character traits are sensitivity, regretfulness, blameworthiness, stubbornness, resentfulness, bitterness, timidness, laziness and the like.

"Androstane steroids" are aliphatic polycyclic hydrocarbons characterized by a four-ring steroidal structure, with a methylation at the 10- and 13- positions. An Androstene steroid is a subset of Androstanes, commonly understood to mean that the compound has at least one double bond. Commonly, unless a compound is described as a gonane it is understood that the compound has an 18- carbon group. However, it is intended that 18-Nor-Androstanes are herein regarded as Androstane steroids. Furthermore, all derivatives which have the structural characteristics described above are also referred to generically herein as Androstane steroids.

The following structure shows the four-ring steroidal structure common to Androstene and Estrene steroids. In describing the location of groups and substituents, the following numbering system will be employed:

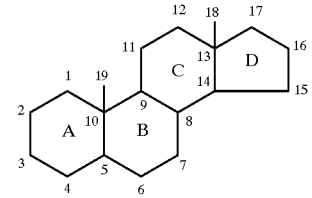

"Sexually dimorphic" refers to a difference in the effect of, or response to, a pharmaceutical agent between males and females of the same species.

An "effective amount" of a drug is a range of quantity and/or concentration which brings about a desired physiological and/or psychological effect when administered to a subject in need of the drug. In the present case, a needy subject is one in need of hypothalamic modulation or regulation, or a subject in need of alteration of a physiological or behavioral characteristic normally affected by the hypothalamus. The effective amount of a given drug may vary depending upon the route of administration. For example, when the steroid is administered as a solution applied to the facial skin of a subject an effective concentration is from about 1 to about 100 µg/ml, preferably about 10 to about 50 µg/ml and most preferably about 20 to about 30 µg/ml. When the steroid is introduced directly into the VNO an effective amount is about 1 pg to about 1 ng, more preferably about 10 pg to about 50 pg. When the steroid is administered to the nasal passage by ointment, cream, aerosol, or the like, an effective amount is about 100 pg to about 100 micrograms, preferably about 1 ng to about 10 micrograms. It follows that some drugs may be effective when administered by some routes, but not effective when administered by other routes.

The "hypothalamus" is the portion of the diencephalon comprising the ventral wall of the third ventricle below the hypothalamic sulcus and including structures forming the ventricle floor, including the optic chiasma, tuber cinereum, infundibulum, and mammillary bodies. The hypothalamus regulates the autonomic nervous system and controls several physiological and behavioral functions such as the so-called fight and flight responses, sexual motivation, water balance, sugar and fat metabolism, hunger, regulation of body temperature, endocrine secretions, and others. The hypothalamus is also the source of vasopressin which regulates blood pressure, and oxytocin which induces parturition and milk release. All hypothalamic functions are potentially modulatable by the semiochemical therapy described herein.

A "ligand", as used herein, is a molecule which acts as a chemical signal by specifically binding to a receptor molecule displayed on the surface of a receptor cell, thereby initiating a signal transduction across the cell surface. Binding of ligands to chemosensory receptors can be measured. Chemosensory tissue, such as vomeronasal neuroepithelium or olfactory neuroepithelium, contains a multiplicity of neuroreceptors cells, each displaying at least one cell surface receptor. Many of the receptor molecules have identical ligand specificity. Therefore, when the tissue is exposed to a ligand for which it has specificity (for example a exposure of the VNO to a semiochemical) a summated change in cell surface receptor potential can be measured.

As used herein, "lower alkyl" means a branched or unbranched saturated hydrocarbon chain of 1 to 4 carbons, such as, for example, methyl, ethyl, n-propyl, i-butyl and the like. "Alkoxy" as used herein is used in its conventional sense to mean the group -OR where in R is an alkyl as defined herein.

A "pheromone" is a substance that provides chemical means of communication between members of the same species through secretion and nasus reception. In mammals pheromones are usually detected by receptors in the vomeronasal organ of the nose. Commonly, pheromones effect development, reproduction and related behaviors. A "semiochemical" is a more general term which includes pheromones and describes a substance from any source which functions as a chemosensory messenger, binds to a specific neuroepithelial receptor, and induces a physiological or behavioral effect. A "vomeropherin" is a semiochemical whose physiologic effect is mediated through the vomeronasal organ.

A picogram (pg) is equal to 0.001 nanograms (ng). A ng is equal to 0.001 microgram (µg). A µg is equal to 0.001 mg.

II. Modes for Carrying Out the Invention

A. Estrenes Useful in the Invention

The invention is directed in part to certain Estrene steroids which are structurally related to Estradiol (also referred to as 1,3,5(10)-Etratriene-3,17β-diol). Steroids within the group are characterized by a aromatic 1,3,5(10) A-ring and a hydroxyl or hydroxyl derivative at the 3-position.

Estrenes especially suitable for use in the present invention include those where, independently, $R_1$=oxo, β-hydroxy, hydrogen; $R_2$=methyl, hydrogen; (as depicted in formula I).

Most of these steroids and their glucuronide, sulfate, cypionate, and benzoate derivatives, are compounds known in the art and are commercially available, e.g., from Sigma Chemical Co., Aldrich Chemical Co., etc. Alkoxy derivatives and their synthesis are also known in the art and taught in U.S. Pat. No. 2,984,677, herein incorporated by reference.

Chart 1 includes estrenes to which the invention is directed, but do not limit its scope. The synthesis diagrams that follow depict intermediate and substructure syntheses for the preparation of these estrenes:

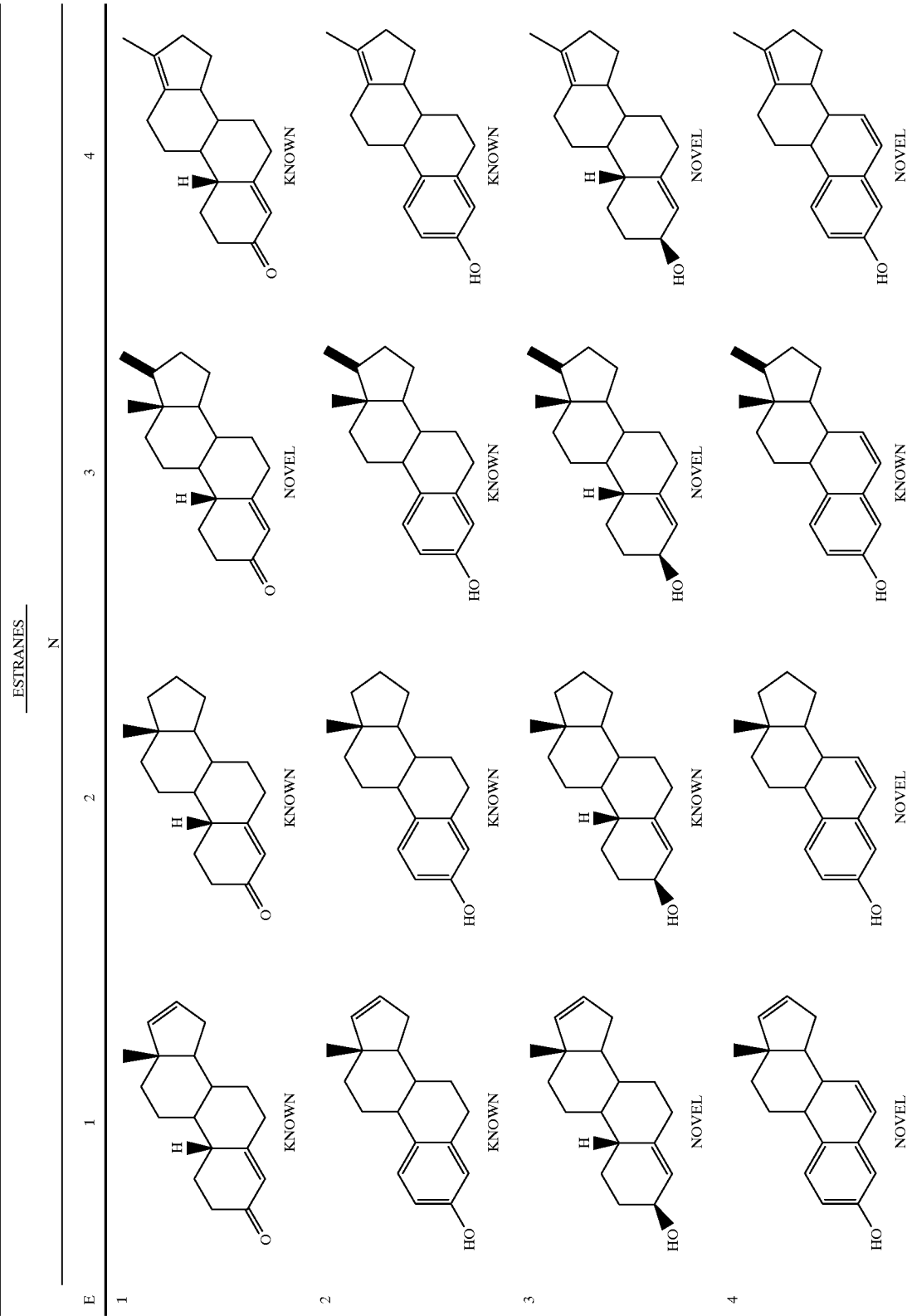

CHART 1-continued
ESTRANES
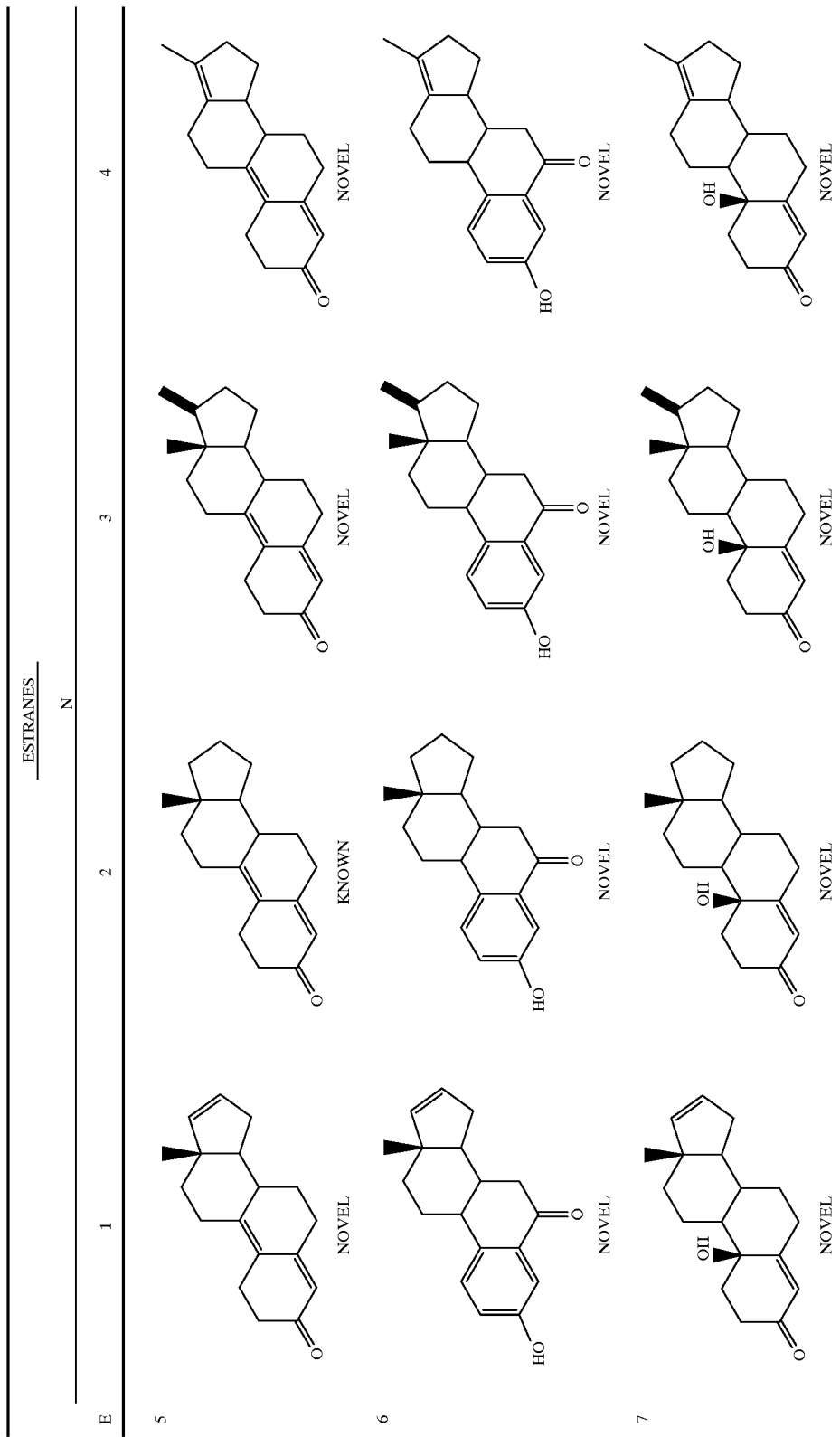

CHART 1-continued
ESTRANES
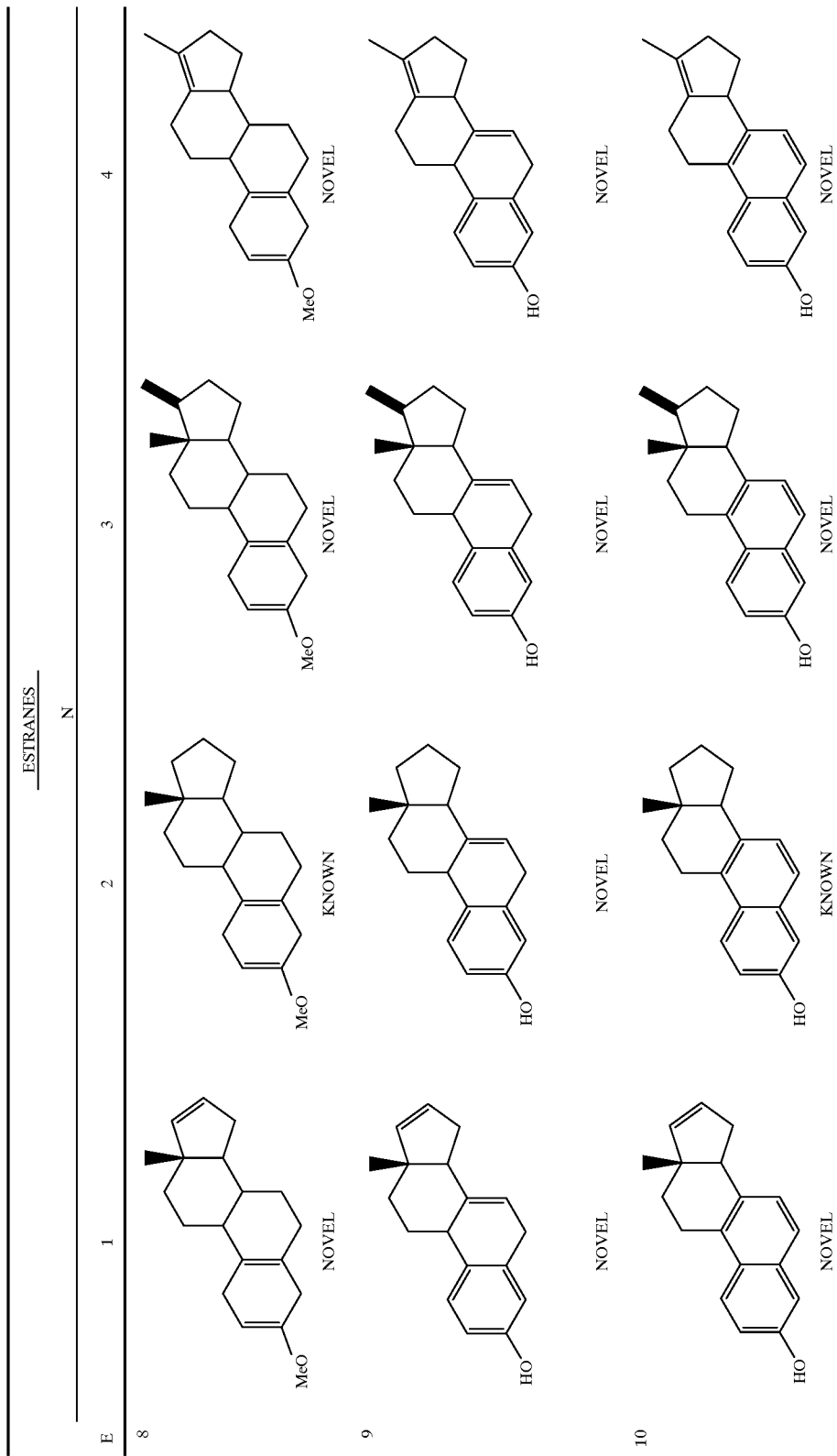

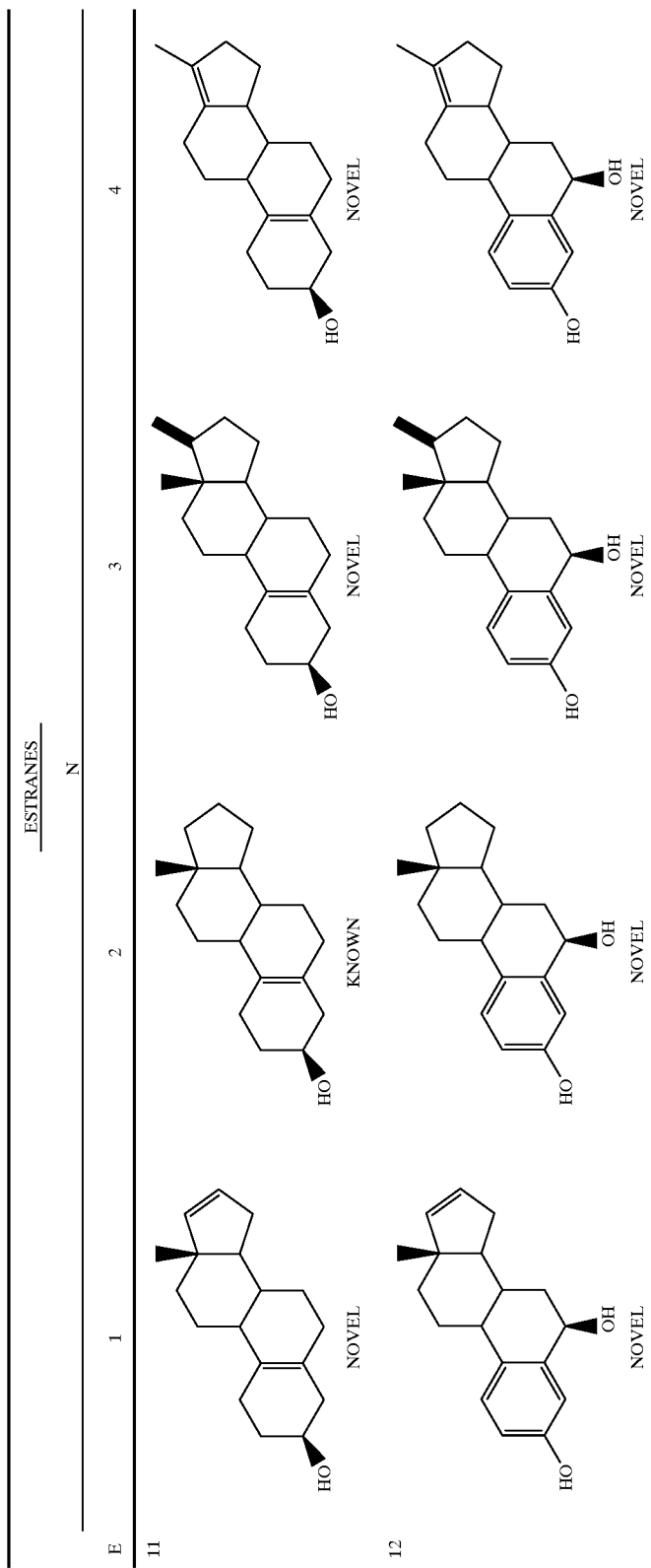

NOVEL ESTRANES

ESTRA-1,3,5(10),6,16-PENTAEN-3-YL ACETATE (Acetate of E4/N1)

ESTRA-1,3,5(10),7-TETRAEN-3-OL (E9/N2)

3-HYDROXY ESTRA-1,3,5(10),16-TETRAEN-6-ONE (E6/N1)

6-OXO ESTRA-1,3,5(10),16-TETRAEN-3-YL ACETATE (Acetate of E6/N1)

17-METHYLENE ESTRA-1,3,5,7,9-PENTAEN-3-OL (E10/N3)

ESTRA-1,3,5(10),16-TETRAEN-3,6B-DIOL (E12/N1)

6B-HYDROXYESTRA-1,3,5(10),16-TETRAEN-3-YL ACETATE (Acetate of E12/N1)

ESTRA-4,16-DIEN-3B-OL (E3/N1)

17-METHYLENE-6-OXOESTRA-1,3,5(10)-TRIEN-3-YL ACETATE (Acetate of E6/N3)

ESTRA-4,9,16-TRIEN-3-ONE (E5/N1)

ESTRA-1,3,5,7,9,16-HEXAEN-3-OL (E10/N1)

ESTRA-1,3,5(10),6-TETRAEN-3-OL (E4/N2)

3-METHOXYESTRA-2,5(10),16-TRIENE (E8/N1)

10-HYDROXYESTRA-4,16-DIEN-3-ONE (E7/N1)

17-METHYLENEESTRA-1,3,5(10),7-TETRAEN-3-OL (E9/N3)

ESTRA-5(10),16-DIEN-3a-OL (3a epimer of E11/N1)

ESTRA-5(10),16-DIEN-3a-OL (E11/N1)

17-METHYLENEESTRA-4-EN-3-ONE (E1/N3)

ESTRA-1,3,5,7,9,16-HEXAEN-3-YL ACETATE (Acetate of E10/N1)

17-METHYLGONA-4,13(17)-DIEN-3B-OL (E3/N4)

ESTRA-1,3,5,(10),7,16-PENTAEN-3-OL (E9/N1)

3-METHOXY-17-METHYLENEESTRA-2,5(10)-DIEN (E8/N3)

17-METHYLENEESTRA-4-EN-3B-OL (E3/N3)

17-METHYLENEESTRA-1,3,5(10)-TRIENE-3,6B-DIOL (E12/N3)

ESTRA-1,3,5(10),7,16-PENTAEN-3-YL ACETATE (Acetate of E9/N1)

STRA-1,3,5(10),6,16-PENTAEN-3-OL (E4/N1)

17-METHYLENEESTRA-1,3,5(10),7-TETRAEN-3-YL ACETATE (Acetate of E9/N3)

SUBSTRUCTURE SYNTHESES

Referring to the preceding table, the following are exemplary syntheses for intermediates in a given row (E1 through E12) or column (N1 through N4).

E1: Type E

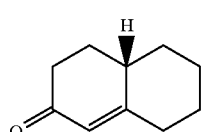

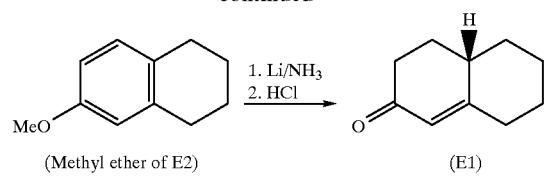

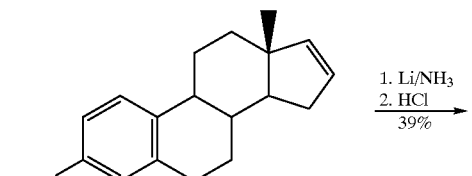

E2:

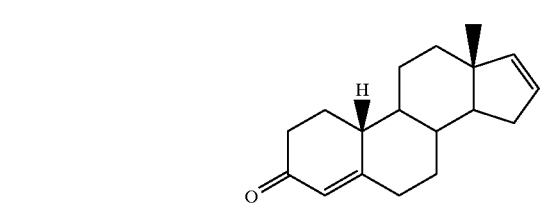

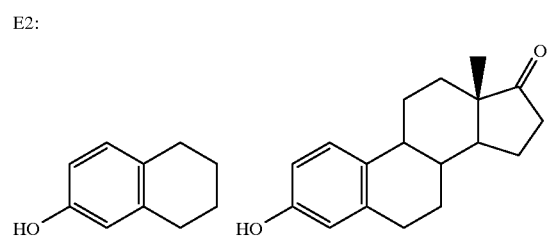

Commercially available substructure, for example, ESTRONE.

E3:

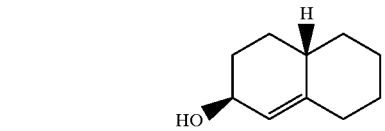

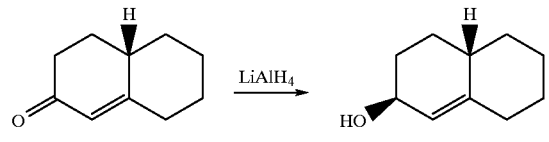

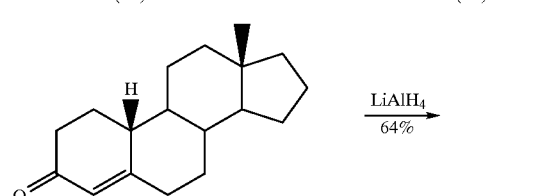

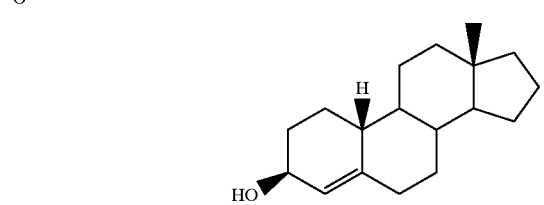

James R. Bull and Jan Floor, J. Chem. Soc. Perkin I, 1977 (7), 724.

E4:
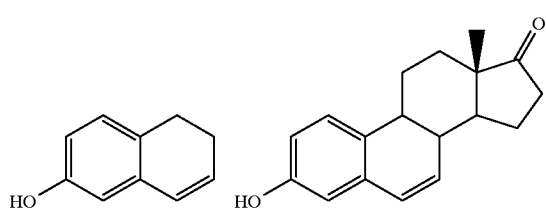
Commerically available substructure, for example, 6-DEHYDROESTRONE.
E5:
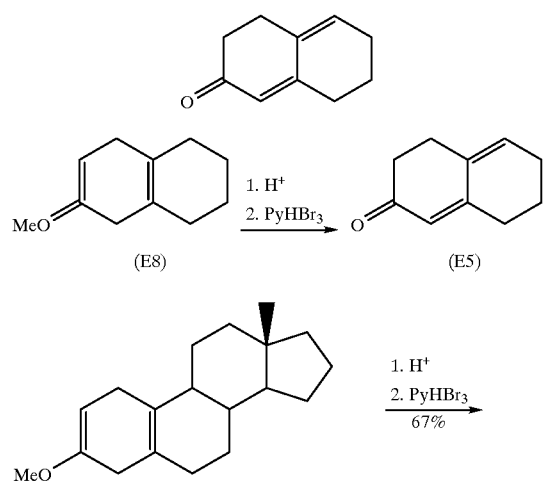
V. I. Mel'nikova and K. K. Pivnitskii, Zhurnal Organickeskoi Khisnii, 1974, Vol. 10, No. 5, pp. 1014–1019).
E6:
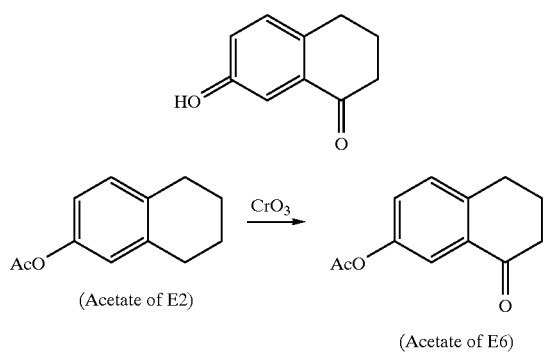
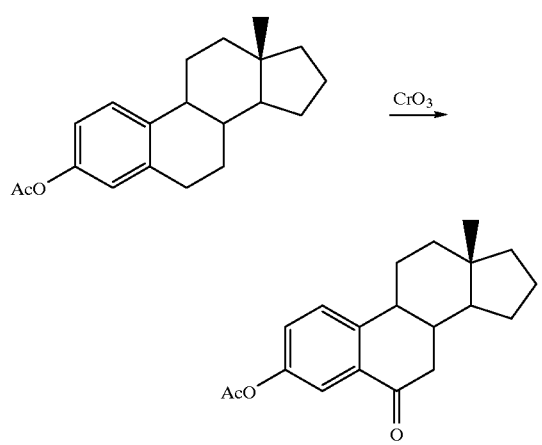
Hidetoshi Takagi, Ken-ichi Komatsu, and Itsuo Yoshisawa, Steroids, 1991, Vol. 56, p. 173.
E7:
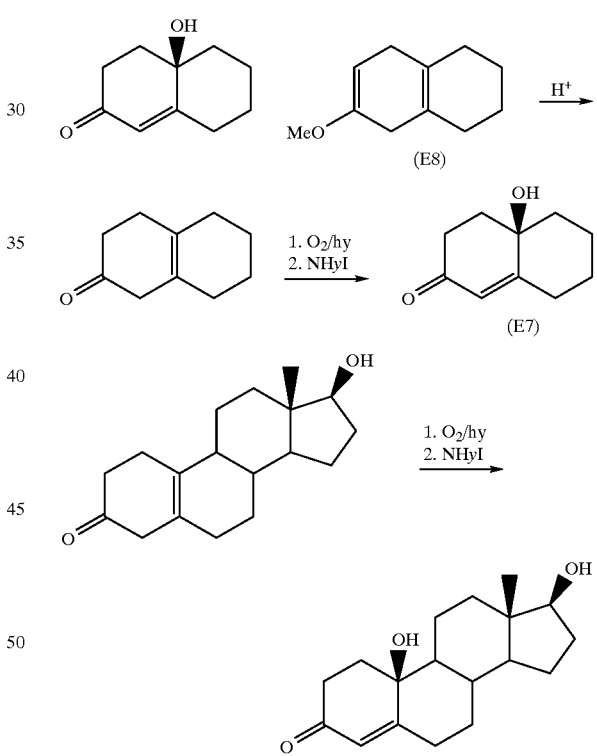
Michel Mauney and Jean Rigaudy, Bull. Soc. Chien, 1976, No. 11–12, 2021.
E8:
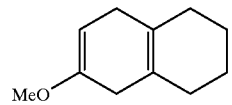

-continued
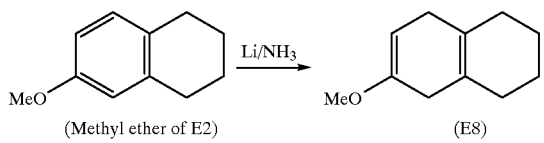
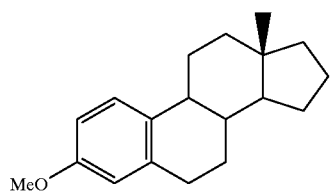
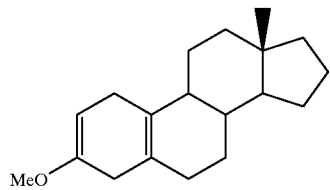
K. J. San, R. H. Blank, R. H. Evans, Jr., L. I. Feldman, and C. E. Holmbund, J. Org. Chem., 1964, 2351.
E9:
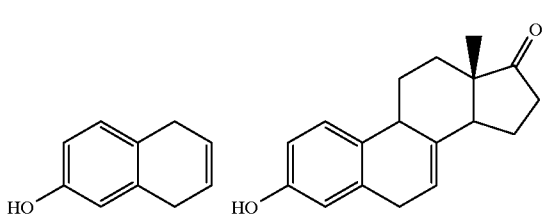
Commercially available substructure, as in EQUILIN.
E10:
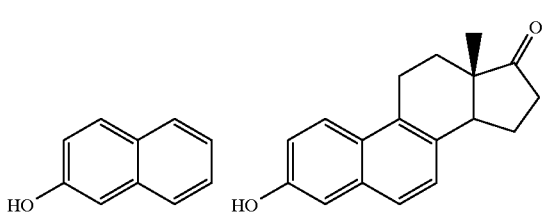
Commercially available substructure, as in EQUILENIN.
E11:
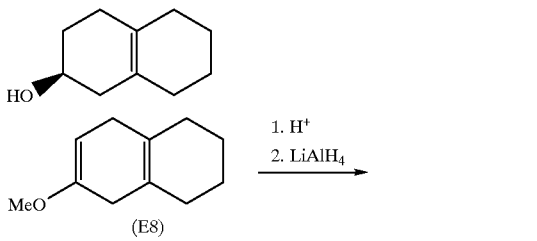
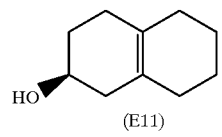
A. N. Cherkasov, A. M. Ponomarev, and K. K. Pivnitskii, Zhurnal Organiskeskoi Khimii, 1971, Vol. 7, No. 5, pp. 940–947.
E12:
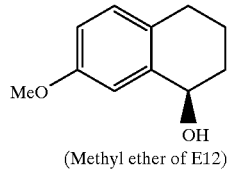
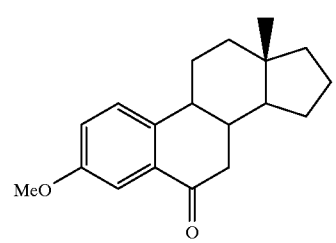
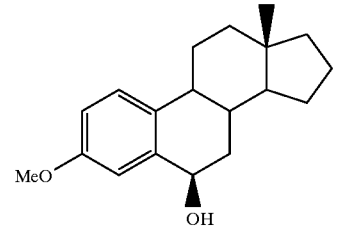

Hidetoshi Takagi, Ken-ichi Komatsu, and Itsuo Yoshisawa, Steroids, 1991, Vol. 56, p. 173.
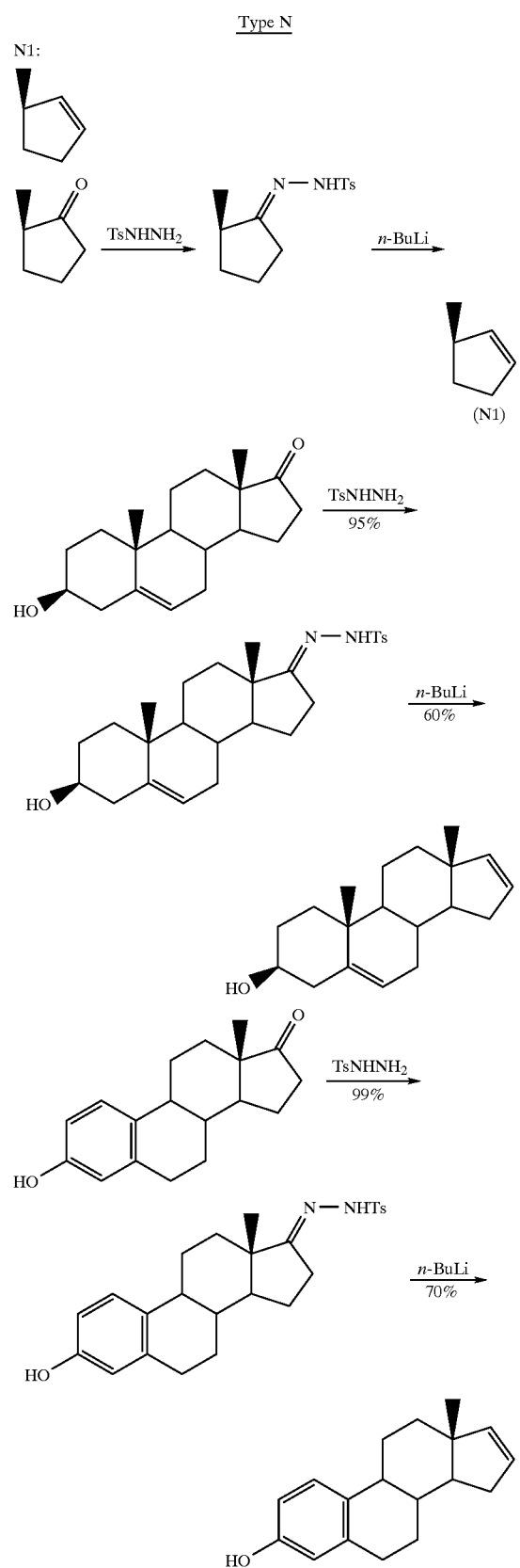
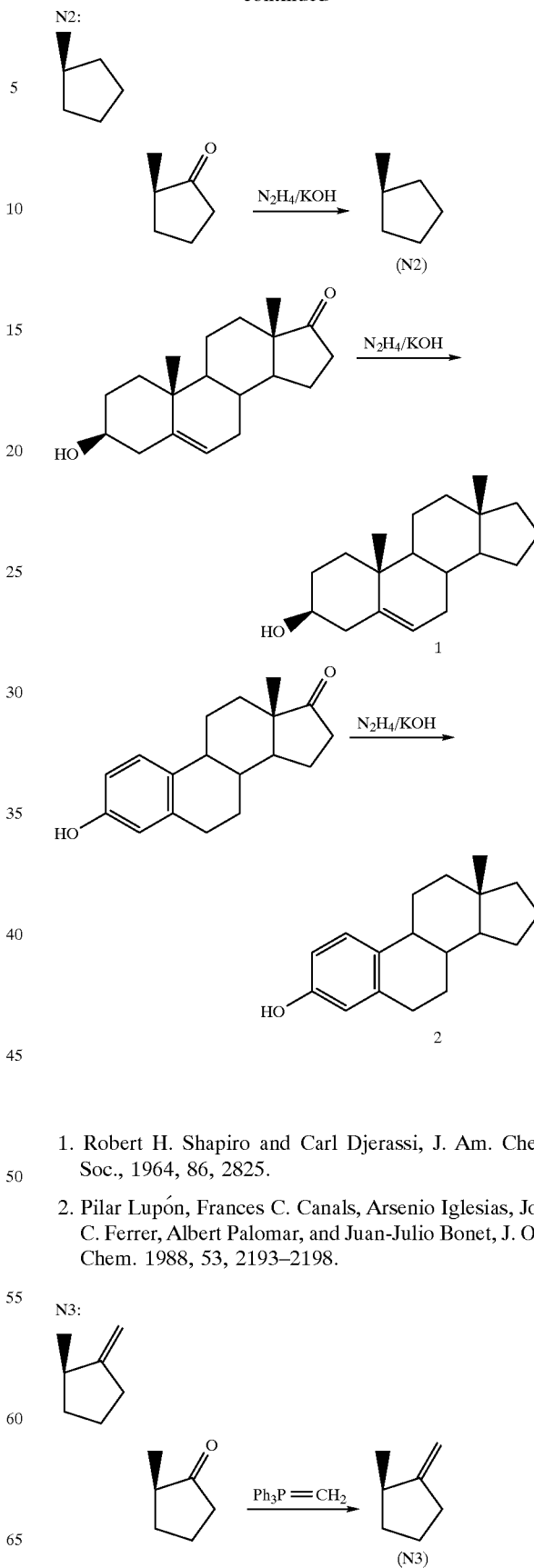
1. Robert H. Shapiro and Carl Djerassi, J. Am. Chem. Soc., 1964, 86, 2825.
2. Pilar Lupón, Frances C. Canals, Arsenio Iglesias, Joan C. Ferrer, Albert Palomar, and Juan-Julio Bonet, J. Org. Chem. 1988, 53, 2193–2198.

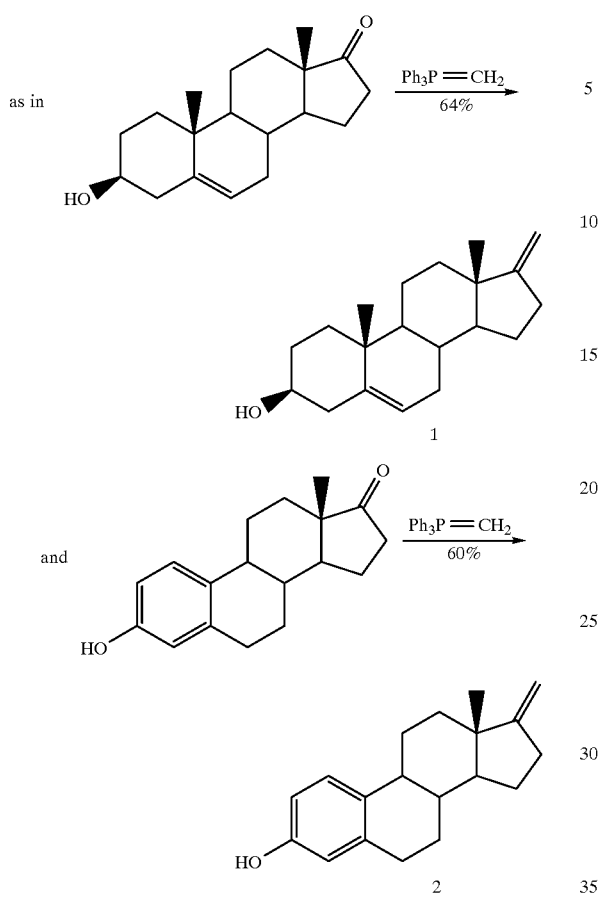
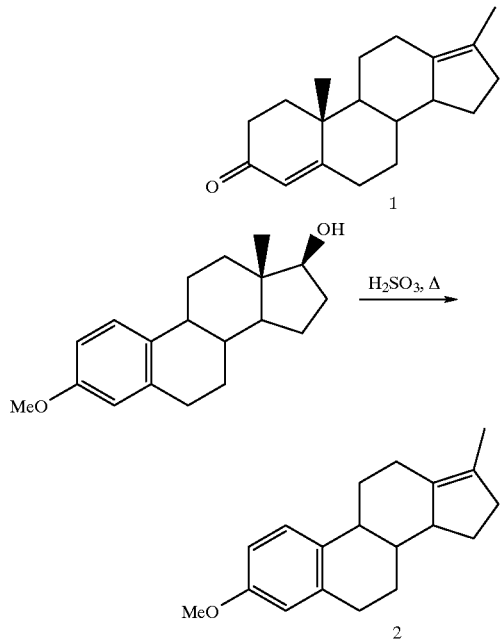
1. Franz Sonheimer, O. Moncera, M. Viquiza & G. Rosenkranz (1955) J. Am. Chem. Soc. 77:4145.
2. William F. Johns, J. Org. Chem., 1961, 26, 4583.
1. Günther Drefahl, Kurt Ponold and Hans Schick, Berichte, 1965, 98, 604.
2. Richard H. Peters, David F. Crows, Mitchell A. Avery, Wesley K. M. Chong, and Masako Tanabe, J. Med. Chem., 1989, 32, 1642.
N4:
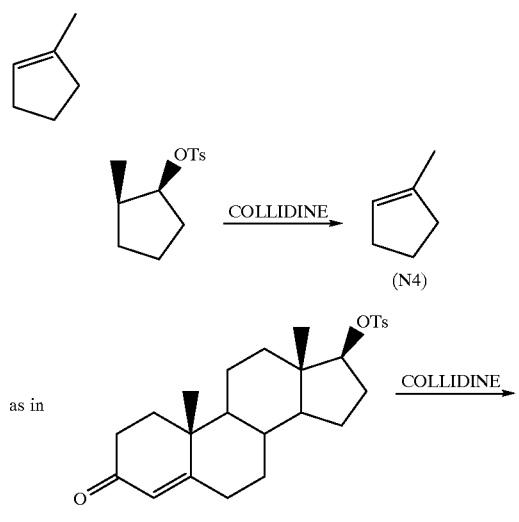
Methylestrenes
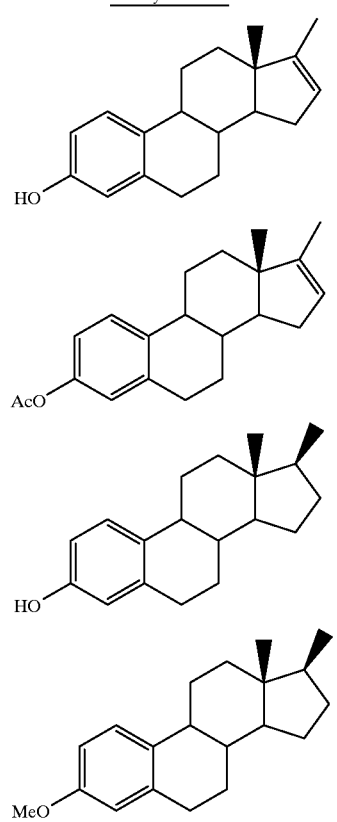

Harold J. Nicholas, J. Org. Chem., 1958, 23, 1747.

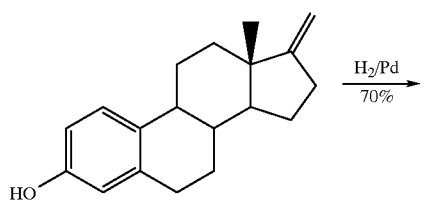

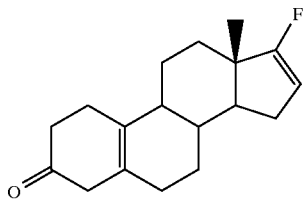

Richard H. Peters, David F. Crows, Mitchell A. Avery, Wesley K. M. Chong, and Masako Tanabe, J. Med. Chem., 1989, 32, 1642.

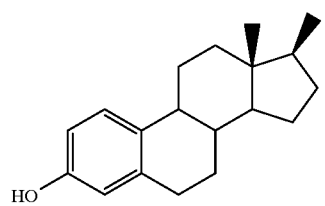

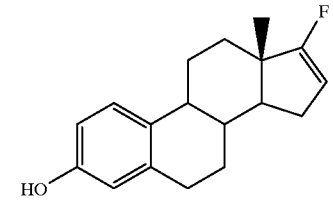

M. B. Green and F. J. Zeelen, Tetrahedron Letters, 1982, Vol. 23, No. 35, pp. 3611–3614.

Synthesisable compounds therefore include these, together with those derived from them; i.e., 17-Methyl-N1, 17β-Methyl-N2, or 14α-Methyl-N4, in combination with E1, E2, E3, E5, E6, E7, E8, E11 or E12.

Haloestrenes

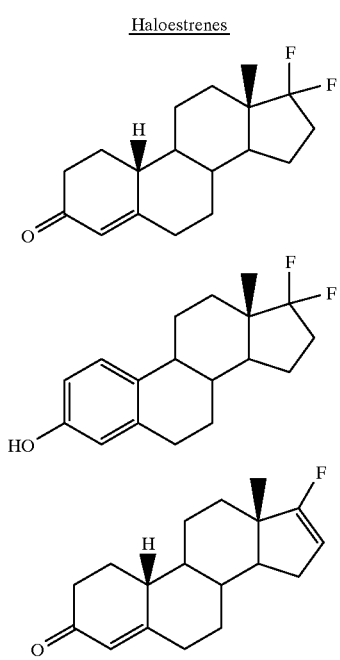

-continued

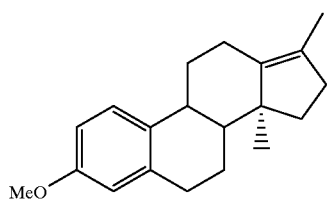

George A. Boswell in patent C.A. 70:58140 g, following.

G. Michael Blackburn, Brian F. Taylor, and Andrew F. Worrall, Journal of Labelled Compounds and Radiopharmaceuticals, 1986, Vol. XXIII, No. 2, p. 197.

Synthesisable compounds therefore include these, together with those derived from them; i.e., 17-Fluoro-N1 in combination with E1, E2, E3, E5, E6, E7, E11 or E12. In addition, 17-Iodo-N1 in combination with E2, E6 or E12.

B. Synthetic Methods

General procedures for synthetic reactions of steroids are known to those skilled in art (See for example, Fieser, L. F. and M. Fieser, *Steroids,* Reinhold, N.Y. 1959). Where time and temperature of reactions must be determined, these can be determined by a routine methodology. After addition of the required reagents, the mixture is stirred under an inert atmosphere and aliquots are removed at hourly intervals. The aliquots are analyzed by means of thin-layer chromatography to check for the disappearance of starting material, at which point the work-up procedure is initiated. If the starting material is not consumed within twenty-four hours, the mixture is heated to reflux and hourly aliquots are analyzed, as before, until no starting material remains. In this case the mixture is allowed to cool before the work-up procedure is initiated.

Alkoxy derivatives of Estrenes are prepared from their corresponding hydroxy steroids by reaction with an alkylating agent such as trimethyloxonium fluoroborate, triethyloxonium fluoroborate or methylfluorosulfonate in an inert chlorocarbon solvent such as methylene chloride. Alternatively, alkylating agents such as alkyl halides, alkyl tosylates, alkyl mesylates and dialkylsulfate may be used with a base such as silver oxide or barium oxide in polar, aprotic solvents as for example, DMF, DMSO and hexamethylphosphoramide. Alternatively, a base such as $K_2Co_3$ may be used in solvents such as ethanol or acetone.

Purification of the products is accomplished by means of chromatography and/or crystallization, as known to those skilled in the art.

C. Pharmaceutical Compositions and Methods of Use

An embodiment of the subject invention is a method of altering the hypothalamic function of an individual. Another embodiment is altering an autonomic function of an individual. These autonomic functions include, but are not limited to, heart rate, respiratory rate, brain wave patterns (percentage alpha cortical activity), body temperature. Other embodiments include, but are not limited to, methods of diminishing negative affect, negative mood or negative character traits of an individual. Another embodiment is a method of treating female premenstrual stress. All of these embodiments are accomplished by means of the nonsystemic, nasal administration of certain Estrene steroids and combinations of Estrene steroids.

This particular mode of administration is distinguished from alternative modes, such as ingestion or injection, in several important ways, these by virtue of the direct contact with the VNO provided by the nasal administration of the steroid ligand. In the methods of this invention, the appropriate ligand is administered directly to the chemoreceptors in the nasal passage and the vomeronasal organ, without pills or needles—i.e., noninvasively. Drug action is mediated through binding of the ligands, described herein, to specific receptors displayed by neuroepithelial cells in the nose, preferably in the VNO. This mode of drug action is through the nervous system and not through the circulatory system—thus brain function can be affected without consideration of the blood-brain barrier. These methods of treatment provide a direct means of affecting the hypothalamus through the nervous system because there is only one synaptic junction between pheromone receptors and the hypothalamus. Because sensory nerves are addressed to a specific location in the brain, this method has a highly specific drug effect, thereby greatly reducing the potential of undesirable side-effects.

VNO contact is important because the VNO is associated with chemoreceptive/pheromonal function. The VNO consists of a pair of blind tubular diverticula which are found at the inferior margin of the nasal septum. The VNO contains neuro-epithelia, the axons of which have direct synapses to the amygdala and from there, to the hypothalamus. The existence of the VNO has been well documented in most terrestrial vertebrates including the human fetus; however, in adult humans it is generally thought to be rudimentary (See Johnson, et al., supra).

The active compounds described herein, or their sulfated, cypionated, benzoated, propionated, halogenated or glucuronated derivatives, may be administered directly, but are preferably administered as compositions. They are prepared in a liquid dosage form such as, for example, liquids, suspensions or the like, preferably in unit dosage forms suitable for single administration of precise dosages. Liquid dosages may be administered as nose drops or as an aerosol.

Alternatively, the active compound can be prepared as a creme or an ointment composition and applied topically within the nasal cavity. As another alternative, delivery may occur by controlled release of these agents by encapsulation either in bulk or at a microscopic level using synthetic polymers, such as silicone, and natural polymers such as gelatin and cellulose. The release rate can be controlled by proper choice of the polymeric system used to control the diffusion rate (Langer, R. S. and Peppas, N. A., Biomaterials 2,201, 1981). Natural polymers, such as gelatin and cellulose slowly dissolve in a matter of minutes to hours while silicone remains intact for a period of months. The compositions will include a conventional pharmaceutical carrier or excipient, one or more of the active Estrene compound(s) of Formula I. In addition, the compositions may include other medicinal agents, pharmaceutical agents, carriers, adjuvants, etc.

The most likely means of communication of a putative human pheromone is the inhalation of a naturally occurring pheromone present on the skin of another. Several 16-Androstene steroids, including 5α-Androst-16-en-3α-ol and 5α-Androst-16-en-3-one, 4,16-Androstadien-3-one, 5α-Androstadien-3β-ol, and perhaps 5α-Androstadien-3α-ol, are naturally occurring in humans and may be present on the skin. It is estimated that the naturally occurring maximum concentration of a 16-Androstene steroid on human skin is from 2 to 7 $ng/cm^2$. During intimate contact it is estimated that a human would be exposed to no more than 700 ng of a naturally occurring steroid. Since these compounds are relatively non-volatile, it is estimated that, even during intimate contact, a human subject would inhale no more than 0.7 pg of a naturally occurring steroid from the skin of another. From the amount inhaled only about 1% would reach the receptors of the vomeronasal organ. Thus the estimated maximum natural exposure to naturally produced pheromones would be 0.007 pg.

The amount of active compound administered will of course, be dependent on the subject being treated, the severity of the affliction, the manner of administration, the frequency of administration, and the judgment of the prescribing physician. However, a single dosage of at least about 10 picograms, delivered directly into the lumen of the vomeronasal organ, is effective in eliciting a transient autonomic response when administered to the nasal cavity, the dosage is about 100 picograms to about 100 micrograms, preferably about 1 nanogram to about 10 micrograms, more preferably about 10 nanograms to about 1 microgram. The frequency of administration is desirably in the range of an hourly dose to a monthly dose, preferably from 8 times/day to once every other day, more preferably 1 to 3 times per day. Ointments containing one or more active compounds and optional pharmaceutical adjuvants in a carrier, such as, for example, water, saline, aqueous dextrose, glycerol, ethanol, and the like, can be prepared using a base such as, for example, petroleum jelly, lard, or lanolin.

Liquified pharmaceutically administrable compositions can, for example, be prepared by dissolving, dispersing, etc. an active compound as defined above and optional pharmaceutical adjuvants in a carrier, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see *Remington's Pharmaceutical Sciences,* Mack Publishing Co., Easton, Pa., 15th Ed., 1975. The composition or formulation to be administered will, in any event, contain a quantity of one or more of the active compound(s) in an amount effective to alleviate the symptoms of the subject being treated.

For aerosol administration, the active ingredient is preferably supplied in finely divided form along with a surfactant and a propellant.

Typical percentages of active ingredients are 0.001 to 2% by weight, preferably 0.004 to 0.10%.

Surfactants must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, olestearic and oleic acids with an aliphatic polyhydric alcohol or its cyclic anhydride such as, for example, ethylene glycol, glycerol, erythritol, arabitol, mannitol, sorbitol, and hexitol anhydrides derived from sorbitol (the sorbitan esters sold under the trademark "Spans") and the polyoxyethylene and polyoxypropylene derivatives of these esters. Mixed esters, such as mixed or natural glycerides, may be employed. The preferred surface-active agents are the oleates or sorbitan, e.g., those sold under the trademarks "Arlacel C" (sorbitan sesquioleate), "Span 80" (sorbitan monooleate) and "Span 85" (sorbitan trioleate). The surfactant may constitute 0.1–20% by weight of the composition, preferably 0.25–5%.

The balance of the composition is ordinarily propellant. Liquefied propellants are typically gases at ambient conditions, and are condensed under pressure. Among suitable liquefied propellants are the lower alkanes containing up to five carbons, such as butane and propane; fluorinated or fluorochlorinated alkanes, such as are sold under the trademark "Freon". Mixtures of the above may also be employed.

In producing the aerosol, a container equipped with a suitable valve is filled with the appropriate propellant, containing the finely divided active ingredient and surfactant. The ingredients are thus maintained at an elevated pressure until released by action of the valve.

Yet another means of administration is topical application of a volatile liquid composition to the skin, preferably facial skin, of an individual. The composition will usually contain an alcohol such as ethanol or isopropanol. A pleasant odorant may also be included in the composition.

D. Measuring Affect, Mood and Character Traits.

Feeling states associated with affects, moods and character traits are generally measured by use of a questionnaire. For example questionnaires comprising a number of adjectives which refer to feeling states may be administered to an individual. The individual evaluates his or her feeling state described by the adjective and rates the intensity of the feeling on a numerical scale. Clustering of related adjectives and statistical analysis of a subject's evaluation of each adjective provides a basis for the measurement of various feeling states.

Alternatively, feeling states may be measured by autonomic changes, such as those used in polygraphic evaluations (galvanic skin response, pulse rate and the like). Cabanac, M. Annual Review of Physiology (1975) 37:415; Hardy, J. D., "Body Temperature Regulation", Chapter 59, pp. 1417. In: Medical Physiology. Vol. IIEd.: VB Mountcastle (1980); Wolfram Bouscein. Electrodermal Activity (Plenum Press 1992).

In addition, non-verbal cues such as facial expression and body posture may be evaluated.

III. EXAMPLES

The following examples are intended to illustrate but not to limit the invention.

Abbreviations used in the examples are as follows: aq.= aqueous; RT.=room temperature; PE=petroleum ether (b.p. 50–70°); DMF-N, N-dimethylformamide; DMSO-dimethyl sulfoxide; THF-tetrahydrofuran.

Example 1

Synthesis of Estra-1,3,5(10),16-tetraen-3-ol (28).

Figure 1:
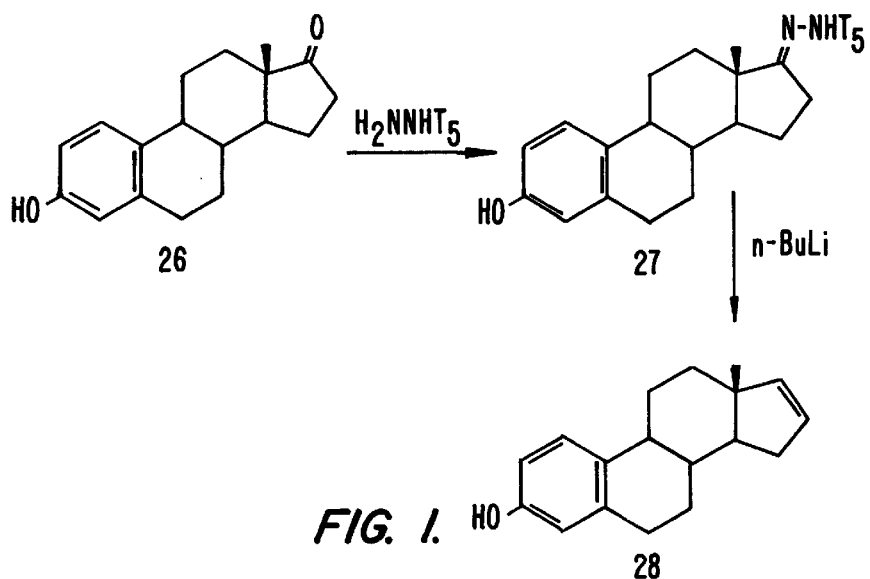
FIG. 1 illustrates the synthesis of 1, 3 ,5 (10), 16-Estratetraen-3-ol.

The following method of synthesis is depicted in FIG. 1:

Estrone p-Toluenesulfonylhydrazone (27)

Estrone (26) (270 g, 1.00 mole) and p-toluenesulfonylhydrazide (232.8 g, 1.25 mole) in dry methanol (2.5 liters) were heated under reflux for 20 hours. The mixture was transferred to a conical flask and allowed to cool. The crystalline product was filtered off under suction and washed with methanol (300 ml). Further crops of product were obtained by sequentially evaporating the filtrate to 2000 ml, 800 ml and 400 ml, and allowing to crystallize each time. Total yield was 433.5 g (99%).

1,3,5(10),16-Estratetraen-3-ol (28):

Estrone p-toluenesulfonylhydrazone (27) (219.0 g, 500 m mole) in dry tetrahydrofuran (8.0 liters) was cooled in a sodium chloride/ice bath. The mixture was mechanically stirred while n-butyl lithium (800 ml of a 2.5 M solution in hexane, 2.00 mole) was added via double-ended needle. The mixture was stirred at room temperature for 3 days. Ice (250 g) was added, followed by saturated ammonium chloride solution (500 ml). The phases were mixed by stirring and then allowed to settle. The aqueous phase was removed via aspiration with teflon tube and extracted with ether (500 ml). The two organic phases were sequentially washed with the same batch of saturated sodium bicarbonate solution (500 ml) followed by saturated sodium chloride solution (500 ml). The organic layers were dried ($MgSO_4$) and evaporated in vacuo to give crude product. This was subjected to flash filtration on 500 g silica gel 60, 230–400 mesh, eluting with ethyl acetate/hexane (25:75, 2.5 liters) The filtrate was evaporated in vacuo to give crystalline material. The product was recrystallized from methanol (300 ml)/water (75 ml) washing with methanol (80 ml)/ water (20 ml). Further recrystallization from ethyl acetate/hexane (12.5:87.5) gave pure product (88.9 g, 70%).

Example 2

Synthesis of Acyl derivatives of 1,3,5(10), 16-Estratetraen-3-ol.

To 1,3,5(10),16-Estratetraen-3-ol (254 mg, 1.00 mMole) in ether (10 ml) is added acetic anhydride (0.25 ml) (or propionic anhydride for the propionate) followed by pyridine (0.25 ml) and the mixture is stirred at room temperature for 16 hours. The mixture is poured into ice/water and extracted with ether (2×20 ml). The organic extracts are washed with water, saturated copper sulfate solution, water, and saturated sodium chloride solution, dried ($MgSO_4$) and evaporated in vacuo to give the crude material. This is purified by flash chromatography on 17.5 g silica gel 60 (230–400 mesh) eluting with 10%–12% ethyl acetate/ hexane to give the pure product (192 mg, 65%).

Example 3

Synthesis of Estra-4,16-dien-3-one (1).

To estra-1,3,5(10),16-tetraene-3-methyl ether (551.5 mg., 2.055 mmol) in 8.6 ml of anhydrous THF, approximately 30 ml of anhydrous ammonia, and 6.76 g of t-butyl alcohol was added lithium wire (0.24 g, 35 mg-atom) cut in small pieces. The reaction mixture was refluxed 4½ h under argon, after which methanol (2.3 ml) was added and the ammonia was allowed to boil off overnight. The residue was dissolved in 25 mL of methanol and was acidified to approximately pH 1 with 5N HCI. After heating in an oil bath between 55 and 70° C. for 15 min. the cooled hydrolysis mixture was partitioned between 25 ml of water and 50 ml of ethyl acetate and the aqueous phase was extracted with 25 ml of ethyl acetate. The combined organic extracts were washed with 25 ml of saturated sodium bicarbonate and 25 mL of brine, dried over magnesium sulfate, and filtered. Removal of solvent under reduced pressure yielded 0.57 g of oily residue which was purified by flash chromatography on silica gel (eluent: 15% ethyl acetate/hexane) followed by recrystallization from pentane to give crystals (206.1 mg, 39%) homogeneous to TLC, m.p. 67–71° C.

Example 4

Synthesis of Estra-2,5(10),16-triene-3-methyl ether (2).

To Estra-1,3,5(10),16-tetraene-3-methyl ether (1.22 g, 4.54 mmole) in 19 ml of anhydrous THF, 14.99 g of t-butyl alcohol, and approximately 70 ml of anhydrous ammonia was added lithium wire (0.53 g, 76 mg-atom) cut in small pieces. After refluxing under argon for 6 h the reaction was quenched with 5 ml of methanol and ammolonia was allowed to boil off overnight. A suspension of the residue in 100 ml of water was extracted twice with 100 ml portions of ethyl acetate and the combined organic extracts were washed with brine and dried over magnesium sulfate. Following solvent removal under reduced pressure the residue was flash chromatographed on silica gel using 1% ethyl acetate/hexane as eluent and then recrystallized from abs. ethanol to give fluffy white crystals (884.1 mg, 3.269 mmole, 72%), m.p. 72–73° C., homogeneous to TLC.

Example 5

Synthesis of Estra-5(10),16-dien-3-one (3).

Estra-2,5(10),16-triene-3-methyl ether (2) (646.3 mg, 2.390 mmole), dissolved in 50 ml of acetone was hydrolyzed for 6 h at room temperature using oxalic acid dihydrate (0.84 g, 6.7 mmole). The reaction mixture was quenched with 25 ml of saturated sodium bicarbonate and then extracted twice with 25 ml portions of ethyl acetate. The combined organic extracts were washed twice with 25 ml of brine, dried over magnesium sulfate, filtered, and concentrated under reduced pressure. The residue was recrystallized from hexane to give product (462.5 mg, 1.804 mmole, 75%), m.p. 112–116° C.

Example 6

Synthesis of Estra-5(10),16-dien-3-ols (4).

Estra-5(10),16-dien-3-one (3) (301.1 mg, 1.174 mmole), in 6 mL of anhydrous ether was reduced for 1 h at room temperature using lithium aluminum hydride (50.0 mg, 1.32 mmole). After quenching with sodium sulfate decahydrate (2.00 g) for 10 min. the suspension was filtered through Celite and the residue washed with four 25 mL portions of ether. The combined filtrates were concentrated under reduced pressure and purified by flash chromatography (silica gel, 5% ethyl acetate/ hexanes eluent) with subsequent preparative TLC of mixed fractions. The more polar product could be recrystallized with considerable loss from aqueous ethanol to give 4.8 mg of solid. The less polar product was recrystallized from aqueous methanol to give white crystals (59.5 mg), m.p. 98–100° C. Total yield was 64.3 mg (0.249 mmole, 21%).

Example 7

Synthesis of Estra-4,9,16-trien-3-one (5).

Estra-5(10),16-dien-3-one (3) (0.38 g, 1.5 mmole), in pyridine (5.0 mL, 62 mmole) was cooled in an ice-salt bath to −13° C. and pyridinium bromide perbromide (1.58 g, 4.94 mmole) was added in small portions so that T<−4° C. After swirling 1 min. phenol (0.25 g, 2.7 mmole) was added and reaction continued 24 h at room temperature. Ethyl acetate (50 ml) was added and the reaction mixture was washed with 25 ml of 1N HCl, two 25 ml portions of saturated copper sulfate, 25 ml of 5% sodium hydroxide, and 25 ml of brine. After drying over magnesium sulfate, filtration, and concentration under reduced pressure the residue was taken up in 10 mL of abs. ethanol, granular zinc (0.33 g, 5.0 mg-atom) was added, and the mixture was refluxed ½ h. The supernatant was removed, the residue was washed with 10 mL of abs. ethanol, and the combined supernatants were concentrated under reduced pressure. The resulting resin was flash chromatographed on silica gel using 15% ethyl acetate/ hexane as eluent. Appropriate fractions were pooled, concentrated, and then recrystallized from hexane to give solid product (117.5 mg, 0.4619 mmol, 31%), m.p. 87–92° C.

Example 8

Synthesis of Estra-1,3,5(10),16-tetraen-6-one-3-acetate (6).

Chromium trioxide (13.40 g, 0.1340 mol) was suspended in 200 mL of methylene chloride and then cooled to −10° C. in an ice-salt bath. 3,5-Dimethylpyrazole (12.90 g, 0.1342 mol) was added and the mixture was stirred 20 min. Estra-1,3,5(10),16-tetraen-3-yl acetate (4.00 g, 13.5 mmol) in a chilled solution of 20 mL of methylene chloride was added and the reaction stirred 2 h, during which time T<−8° C. The mixture was then filtered through 200 g of silica gel and the product was eluted with further methylene chloride. After combining and concentrating appropriate fractions the crude product was flash chromatographed on silica gel using 15% ethyl acetate/hexane as eluent. Pooling of appropriate fractions and concentration under reduced pressure yielded a white solid (0.92 g, 3.0 mmol, 22%), m.p. 87–103° C.

Example 9

Synthesis of Estra-1,3,5(10),16-tetraen-3-ol-6-one (7).

Estra-1,3,5(10),16-tetraen-6-one-3-acetate (203.1 mg, 0.6543 mmol) in 30 of methanol was saponified with 1.5 mL of 5% (w/w) sodium hydroxide for 40 min. The reaction mixture was concentrated under reduced pressure, taken up in 50 mL of water, neutralized with 1N HCl, and extracted three times with 25 mL portions of methylene chloride. The combined organic extracts were washed with 50 mL of brine, dried over magnesium sulfate, filtered, and concentrated to give a white solid which was purified by recrystallization from benzene/hexane and preparative TLC to give white crystalline solid (52.8 mg, 0.197 mmol, 30%), m.p. 188–191° C.

Example 10

Synthesis of Estra-1,3,5(10),16-tetraen-6α-ol-3-yl acetate (8).

Estra-1,3,5(10),16-tetraen-6-one-3-yl-acetate (6) (421.4 mg, 1.358 mmol), suspended in 35 mL of 95% ethanol was reduced with sodium borohydride (98.8 mg, 2.61 mmol) for 100 min. at room temperature. After concentrating under reduced pressure the residue was suspended in 25 mL of water, neutralized with 1N HCl, and extracted three times with 25 mL portions of methylene chloride. The combined organic extracts were washed with 25 mL of brine, dried over magnesium sulfate, filtered, and concentrated. The resulting white foam was flash chromatographed on silica gel using 25% ethyl acetate/hexane as eluent. Combining fractions and concentration gave a white solid (0.12 g, 0.38 mmol, 28%), m.p. 209–212° C.

Example 11

Synthesis of Estra-1,3,5(10),16-tetraene-3,6-diol (9).

To a suspension of lithium aluminum hydride (LAH, 95%, 46.9 mg, 1.17 mmol) in 5 mL of anhydrous THF was added estra-1,3,5(10),16-tetraen-6-one-3-yl-acetate (6)

(422.9 mg, 1.360 mmol) in 5 mL of anhydrous THF dropwise, with stirring. The reaction was stirred 50 min., after which further LAH (46.5 mg, 1.16 mmol) was added and the reaction stirred 22 h. After refluxing 4 h TLC still showed starting material. The reaction was quenched with 0.5 mL of water +0.5 mL of 20% (w/w) sulfuric acid and concentrated under reduced pressure. The residue was extracted four times with 10 mL portions of hot ethyl acetate and filtered through Celite. The combined filtrates were concentrated and purified twice by flash chromatography to give solid product (0.05 g, 0.2 mmol, 10%), m.p. 150–157° C.

Example 12

Synthesis of Estra-1,3,5(10),7-tetraen-3-ol (10).

To a suspension of equilin (100.2 mg, 0.3733 mmol) in 2 mL of diethylene glycol were added hydrazine (59 μL, 1.9 mmol) and potassium hydroxide (0.04 g, 0.7 mmol). The mixture was stirred in an oil bath at 200–214° C. for 2 h, after which the cooled reaction was diluted with 10 mL of water, neutralized with 1N HCl, and extracted three times with 25 mL of ether. The combined organic extracts were washed with 10 mL of brine, dried over magnesium sulfate, filtered, concentrated, and purified by preparative TLC (silica gel, 15% ethyl acetate/hexane eluent) to give a yellow resin.

Product was further purified by decolorizing with charcoal and recrystallization from aqueous ethanol to give tan crystals (13.2 mg, 51.9 μM, 14%), m.p. 130–134° C.

Example 13

Synthesis of 20-Homoestra-1,3,5(10). 6,8,17-hexaen-3-ol (11).

A suspension of triphenylmethylphosphonium bromide (671.0 mg, 1.878 mg) and potassium t-butoxide (212.1 mg, 1.890 mmol) in 2.1 mL of anhydrous DMSO was heated in a 76–86° C. bath under argon for 1 h, after which equilenin (100.1 mg, 0.3579 mmol) in 2.1 mL of anh. DMSO was added and the green solution was stirred 1 h. After cooling 10 mL of ice-1N HCl were added and the mixture was extracted with three 10 mL portions of ether. The combined organic extracts were washed with 10 mL of saturated sodium bicarbonate +10 mL of brine, dried over magnesium sulfate, filtered through Celite, and concentrated under reduced pressure. The residual orange oil was purified by preparative TLC (silica gel, 25% ethyl acetate/hexane) to give product (75.5 mg, 0.286 mmol, 76%) homogeneous to TLC, m.p. 113–121° C.

Example 14

Synthesis of Estra-1,3,5(10),6-tetraen-3-ol (17).

Estra-1,3,5(10),6-tetraen-3-ol-17-one (91.1 mg, 0.339 mmol), hydrazine (54 μL, 1.7 mmol), and potassium hydroxide (0.06 g) in 1.8 mL of diethylene glycol were heated in a 200° C. bath under argon for 2 h. After cooling to RT 10 mL of water were added and the solution was acidified to pH≈2 with 1N HCl. The resulting suspension was extracted three times with 10 mL of ether and the combined organic extracts were washed with 10 mL of brine, dried over magnesium sulfate, filtered through Celite, and concentrated under reduced pressure. The crude solid was purified by preparative TLC (25% ethyl acetate/hexane on silica gel) to give product homogeneous to TLC (5.9 mg, 23 μmol, 7%).

Example 15

Synthesis of Estra-4,16-dien-3-ol (18):

To estra-4,16-dien-3-one, (1) (87.2 mg, 0.340 mmol) in 1.7 mL of anh. ether was added lithium aluminum hydride (15.0 mg, 0.395 mmol) and the suspension was stirred 17 min. Reaction was then agitated 10 min. with 0.50 g of sodium sulfate decahydrate and filtered through Celite. The residue was washed with three 10 mL portions of ether and the combined filtrates were concentrated under reduced pressure. Preparative TLC (5% ethyl acetate/dichloromethane on silica gel) gave crude product (50.0 mg) as a yellow resin. This could be rechromatographed until sufficiently pure.

Example 16

Estra-4,16-dien-3-one (9).

This synthesis is depicted in FIG. 11. 19-Nor-testosterone (XIX) is commercially available, e.g., from Chemical Dynamics Corp. It provides the starting material for 19-Nor-16-androstene derivatives. 19-Nor-testosterone (XIX) was converted into the acetate (Hartman, J. A. et al., *J. Am. Chem. Soc.* (1956) 78:5662) with acetanhydride and pyridine. (a) A solution of this acetate (4.8 g, 15.17 mmol) in toluene (10 ml) was pyrolyzed (b) at 540° (200 Torr, slow $N_2$-stream) in a glass tube packed with quartz pieces. Chromatography of the crude pyrolysate (3.1 g) on silica gel (150 g) with $CH_2Cl_2$ gave 1.1 g (28%) of the homogenous oily ketone 9; +57.9° (C 1) ((27]: m.p. 71–73°).—IR. ($CHCl_3$): 1660 s, 1615 m, 1585 w, H-NMR. (90 MHz): 0.84 (s, 3 H); 5.82 (m, 2 H); 5.87 (br. s, 1 H).

Example 17

Estr-16-en-3-one (10).

This synthesis is depicted in FIG. 11. 19-nor-testosterone was reduced to 19-nor-5a-Androstan-17-ol-3-one (XX) with lithium and ammonia (c) according to the method of Villotti, R., et al. (*J. Am. Chem. Soc.* (1960) 82:5693). Androsta-5a, 17-diol-3-one (XX) was converted into the acetate (Hartman, J. A. et al., *J. Am. Chem. Soc.* (1956) 78:5662) with acetanhydride and pyridine (a). A solution of 17-B-acetoxy-5a-Estran-3-one (8.0 g, 25.1 mmol) in octane/acetone 10:1 (22 ml) was pyrolyzed (b) at 550° (200 Torr, slow $N_2$-stream) Chromatography of the crude product (5.4 g) on silica gel (600 g) with $CH_2Cl_2$ and recrystallization of the homogenous fractions from PE gave 3.13 g (48.3%). of the pure ketone 10. M.p. 51–54°, [a]-+72.8° (C 1.0).—IR. ($CHCl_3$): 1705 s, 1585 w, —$^1$H-NMR. (90 MHz): 0.79 (s, 3 H); 5.71 (m, 1 H); 5.87 (m, 1 H).

Example 18

Estra-16-en-3α-ol (11).

This synthesis is depicted in FIG. 11. L-Selectride (d, lithium tri(sec-butyl)hydridoborate, 4 ml of a 1 M solution in THF, 4 mmol) was added dropwise at 0° to a solution of ketone 10 (800 mg, 3.10 mmol) in dry ether (5 ml). After stirring for 1 h at 0°, water was added (10 ml). The boranes were oxidized by adding 10% aq. NaOH-solution (5 ml), followed by 30% aq. $H_2O_2$-solution (3 ml) and stirring for 3 h at RT. After workup (ether), the crude product (790 mg, Ca. 9:1 mixture of 11 and 12) was chromatographed on silica gel with $CH_2Cl_2$ to give 700 mg (87%) of pure alcohol 11. M.p. 119–120°→123–124° (from PE), $[a]_D$ +40.6° (C=1.0) .—IR. ($CHCl_3$): 3640 m, 3500 br., 1585 w.—$^1$H-NMR. (90 MHz): 0.78 (s, 3 H); 4.09 (m, $w_{1/2}$≈8, 1 H); 5.71 (m, 1 H), 5.87 (m, 1 H).

Example 19

Estra-16-en-3B-ol (12).

This synthesis is depicted in FIG. 11. A solution of the ketone 10 (800 mg, 3.10 mmol) in dry ether (5 ml) was added dropwise at RT. to a slurry of $LiAlH_4$ (38 mg, 1 mmol) in ether (3 ml) (e). After 1 h, the mixture was hydrolyzed with 10% aq. $H_2SO_4$. After workup (ether), the crude product (802 mg, 9:1-mixture of 12 and 11) was chromatographed on silica gel with $CH_2Cl_2$. A small fraction of 11 (70 mg) was eluted first, followed by the main fraction of 12 (705 mg, 87%). M.p. 113–115°, [a]—+36.3° (C=1.0). —IR. ($CHCl_3$): 3640 m, 3500 br., 1585 w. —$^1$H-NMR. (90 MHz): 0.78 (8, 3 H); 3.60 (m, $w_{1/2}$≈(m, 20, 1 H); 5.71 (m, 1 H), 5.87 (m, 1 H).

Example 20

Alternative Synthesis of Estra-4,16-dien-3-one 1

Estra4,16-dien-3-one, 1: To estra-1,3,5(10),16-tetraene-3-methyl ether (551.5 mg, 2.055 mmol) in 8.6 mL of anhydrous THF, approximately 30 mL of anhydrous ammonia, and 6.76 g of t-butyl alcohol was added lithium wire (0.24 g, 35 mg-atom) cut in small pieces. The reaction mixture was refluxed 4½ h under argon, after which methanol (2.3 mL) was added and the ammolonia was allowed to boil off overnight. The residue was dissolved in 25 mL of methanol and was acidified to approximately pH 1 with 5N HCl. After heating in an oil bath between 55 and 70° C. for 15 min. the cooled hydrolysis mixture was partitioned between 25 mL of water and 50 mL of ethyl acetate and the aqueous phase was extracted with 25 mL of ethyl acetate. The combined organic extracts were washed with 25 mL of saturated sodium bicarbonate and 25 mL of brine, dried over magnesium sulfate, and filtered. Removal of solvent under reduced pressure yielded 0.57 g of oily residue which was purified by flash chromatography on silica gel (eluent: 15% ethyl acetate/hexane) followed by recrystallization from pentane to give crystals (206.1 mg, 39% homogeneous to TLC, m.p. 67–71° C. (NA-1993A-38, 42D)

Example 21

Estra-2,5(10),16-triene-3-methyl ether, 2.

To estra-1,3,5(10),16-tetraene-3-methyl ether (1.22 g, 4.54 mmol) in 19 mL of anhydrous THF, 14.99 g of t-butyl alcohol, and approximately 70 mL of anhydrous ammonia was added lithium wire (0.53 g, 76 mg-atom) cut in small pieces. See FIG. 12. After refluxing under argon for 6 h the reaction was quenched with 5 mL of methanol and ammolonia was allowed to boil off overnight. A suspension of the residue in 100 mL of water was extracted twice with 100 mL portions of ethyl acetate and the combined organic extracts were washed with brine and dried over magnesium sulfate. Following solvent removal under reduced pressure the residue was flash chromatographed on silica gel using 1% ethyl acetate/hexane as eluent and then recrystallized from abs. ethanol to give fluffy white crystals (884.1 mg, 3.269 mmol, 72%), m.p. 72–73° C., homogeneous to TLC. (NA-1993A-74, 77A)

Example 22

Estra-5(10),16-dien-3-one, 3.

Estra-2,5(10),16-triene-3-methyl ether, 2 (646.3 mg, 2.390 mmol), dissolved in 50 mL of acetone was hydrolyzed for 6 h at room temperature using oxalic acid dihydrate (0.84 g, 6.7 mmol). See FIG. 12. The reaction mixture was quenched with 25 mL of saturated sodium bicarbonate and then extracted twice with 25 mL portions of ethyl acetate. The combined organic extracts were washed twice with 25 mL of brine, dried over magnesium sulfate, filtered, and concentrated under reduced pressure. The residue was recrystallized from hexane to give product (462.5 mg, 1.804 mmol, 75%), m.p. 112–116° C. (NA-1993A-78A)

Example 23

Estra-5(10),16-dien-3-ols, 4.

Estra-5(10),16-dien-3-one, 3 (301.1 mg, 1.174 mmol), in 6 mL of anhydrous ether was reduced for 1 h at room temperature using lithium aluminum hydride (50.0 mg, 1.32 mmol). See FIG. 12. After quenching with sodium sulfate decahydrate (2.00 g) for 10 min. the suspension was filtered through Celite and the residue washed with four 25 mL portions of ether. The combined filtrates were concentrated under reduced pressure and purified by flash chromatography (silica gel, 5% ethyl acetate/hexanes eluent) with subsequent preparative TLC of mixed fractions. The more polar product could be recrystallized with considerable loss from aqueous ethanol to give 4.8 mg of solid. The less polar product was recrystallized from aqueous methanol to give white crystals (59.5 mg), m.p. 98–100° C. Total yield was 64.3 mg (0.249 mmol, 21%). (NA-1993A-80, 83A, 85A)

Example 24

Estra-4,9,16-trien-3-one, 5.

Estra-5(10),16-dien-3-one, 3 (0.38 g, 1.5 mmol), in pyridine (5.0 mL, 62 mmol) was cooled in an ice-salt bath to –13° C. and pyridinium bromide perbromide (1.58 g, 4.94 mmol) was added in small portions so that T<–4° C. After swirling 1 min. phenol (0.25 g, 2.7 mmol) was added and reaction continued 24 h at room temperature. See FIG. 12.

Ethyl acetate (50 mL) was added and the reaction mixture was washed with 25 mL of 1N HCl, two 25 mL portions of saturated copper sulfate, 25 mL of 5% sodium hydroxide, and 25 mL of brine. After drying over magnesium sulfate, filtration, and concentration under reduced pressure the residue was taken up in 10 mL of abs. ethanol, granular zinc (0.33 g, 5.0 mg-atom) was added, and the mixture was refluxed ½ h. The supernatant was removed, the residue was washed with 10 mL of abs. ethanol, and the combined supernatants were concentrated under reduced pressure. The resulting resin was flash chromatographed on silica gel using 15% ethyl acetate/hexane as eluent. Appropriate fractions were pooled, concentrated, and then recrystallized from hexane to give solid product (117.5 mg, 0.4619 mmol, 31%), m.p. 87–92° C. (NA-1993A-62, 65B)

Example 25

Estra-1,3,5(10),16-tetraen-6-one-3-acetate. 6.

Chromium trioxide (13.40 g, 0.1340 mol) was suspended in 200 mL of methylene chloride and then cooled to –1° C. in an ice-salt bath. 3,5-Dimethylpyrazole (12.90 g, 0.1342 mol) was added and the mixture was stirred 20 min. See FIG. 13. Estra-1,3,5(10),16-tetraen-3-yl acetate (4.00 g, 13.5 mmol) in a chilled solution of 20 mL of methylene chloride was added and the reaction stirred 2 h, during which tine T<–8° C. The mixture was then filtered through 200 g of silica gel and the product was eluted with further methylene chloride. After combining and concentrating appropriate fractions the crude product was flash chromatographed on silica gel using 15% ethyl acetate/hexane as eluent. Pooling of appropriate fractions and concentration under reduced pressure yielded a white solid (0.92 g, 3.0 mmol, 22%), m.p. 87–103° C. (NA-1993B-39B)

Example 26

Estra-1,3,5(10),16-tetraen-3-ol-6-one. 7.

Estra-1,3,5(10),16-tetraen-6-one-3-acetate (203.1 mg, 0.6543 mmol) in 30 of methanol was saponified with 1.5 mL of 5% (w/w) sodium hydroxide for 40 min. See FIG. 13. The reaction mixture was concentrated under reduced pressure, taken up in 50 mL of water, neutralized with 1N HCl, and extracted three times with 25 mL portions of methylene chloride. The combined organic extracts were washed with 50 mL of brine, dried over magnesium sulfate, filtered, and concentrated to give a white solid which was purified by recrystallization from benzene/hexane and preparative TLC to give white crystalline solid (52.8 mg, 0.197 mmol, 30%), m.p. 188–191° C. (NA-1993B-24, 27B)

Example 27

Estra-1,3,5(10),16-tetraen-6α-ol-3-yl acetate, 8.

Estra-1,3,5(10),16-tetraen-6-one-3-yl acetate, 6 (421.4 mg, 1.358 mmol), suspended in 35 mL of 95% ethanol was reduced with sodium borohydride (98.8 mg, 2.61 mmol) for 100 min. at room temperature. See FIG. 13. After concentrating under reduced pressure the residue was suspended in 25 mL of water, neutralized with 1N HCl, and extracted three times with 25 mL portions of methylene chloride. The combined organic extracts were washed with 25 mL of brine, dried over magnesium sulfate, filtered, and concentrated. The resulting white foam was flash chromatographed on silica gel using 25% ethyl acetate/hexane as eluent. Combining fractions and concentration gave a white solid (0.12 g, 0.38 mmol, 28%), m.p. 209–212° C. (NA-1993B-42D)

Example 28

Estra-1,3,5(10),16-tetraene-3,6-diol, 9.

To a suspension of lithium aluminum hydride (LAH, 95%, 46.9 mg, 1.17 mmol) in 5 mL of anhydrous THF was added estra-1,3,5(10),16-tetraen-6-one-3-yl acetate, 6 (422.9 mg, 1.360 mmol) in 5 mL of anhydrous THF dropwise, with stirring. See FIG. 13. The reaction was stirred 50 min., after which further LAH (46.5 mg, 1.16 mmol) was added and the reaction stirred 22 h. After refluxing 4 h TLC still showed starting material. The reaction was quenched with 0.5 mL of water +0.5 mL of 20% (w/w) sulfuric acid and concentrated under reduced pressure. The residue was extracted four times with 10 mL portions of hot ethyl acetate and filtered through Celite. The combined filtrates were concentrated and purified twice by flash chromatography to give solid product (0.05 g, 0.2 mmol, 10%), m.p. 150–157° C. (NA-1993B-29, 32B)

Example 29

Estra-1,3,5(10),7-tetraen-3-ol, 10.

To a suspension of equilin (100.2 mg, 0.3733 mmol) in 2 mL of diethylene glycol were added hydrazine (59 μL, 1.9 mmol) and potassium hydroxide (0.04 g, 0.7 mmol). See FIG. 14. The mixture was stirred in an oil bath at 200–214° C. for 2 h, after which the cooled reaction was diluted with 10 mL of water, neutralized with 1N HCl, and extracted three times with 25 mL of ether. The combined organic extracts were washed with 10 mL of brine, dried over magnesium sulfate, filtered, concentrated, and purified by preparative TLC (silica gel, 15% ethyl acetate/hexane eluent) to give a yellow resin. Product was further purified by decolorizing with charcoal and recrystallization from aqueous ethanol to give tan crystals (13.2 mg, 51.9 μM, 14%), m.p. 130–134° C. (NA-1993B-25C)

Example 30

20-Homoestra-1,3,5(10),6,8,17-hexaen-3-ol, 11.

A suspension of triphenylmethylphosphonium bromide (671.0 mg, 1.878 mg) and potassium t-butoxide (212.1 mg, 1.890 mmol) in 2.1 mL of anhydrous DMSO was heated in a 76–86° C. bath under argon for 1 h, after which equilenin (100.1 mg, 0.3579 mmol) in 2.1 mL of anh. See FIG. 14. DMSO was added and the green solution was stirred 1 h. After cooling 10 mL of ice-1N HCl were added and the mixture was extracted with three 10 mL portions of ether. The combined organic extracts were washed with 10 mL of saturated sodium bicarbonate +10 mL of brine, dried over magnesium sulfate, filtered through Celite, concentrated and purified.

Example 31

Estra-1,3,5(10),6-tetraen-3-ol-17-(p-toluenesulfonyl) hydrazone, 1.

A suspension of 6-dehydroestrone (538.0 mg, 2.004 mmol) and p-toluenesulfonylhydrazide (p-TsNHNH$_2$, 466.6 mg, 2.506 mmol) in anh. methanol (5.4 mL) was refluxed 25 h with exclusion of moisture. See FIG. 15. After concentrating under reduced pressure the reaction residue was flash chromatographed (50% ethyl acetate/hexanes on silica gel) to give an off-white foam (942.5 mg), representing >100% yield. (NA-1994A-295A)

Example 32

Estra-1,3,5(10),6,16-pentaen-3-ol, 2.

To a cooled (ice water bath) solution of crude estral,3,5 (10),6-tetraen-3-ol-17-(p-toluenesulfonyl)hydrazone (1, 942.5 mg, ≦2.004 mmol) in tetrahydrofuran (THF) under argon was added n-butyllithium (2.5 M in hexane, 3.2 mL, 8.0 mol) dropwise with stirring, over a period of 7 min. See FIG. 15. Stirring was continued 48 h, during which the reaction was allowed to gradually warm to room temperature. 50 mL of 1 N hydrochloric acid were added and the reaction mixture was extracted with three 25 mL portions of ether. The combined organic extracts were washed with 50 mL of brine, dried over magnesium sulfate, and filtered through diatomaceous earth. The residue was washed with 10 mL of ether and the combined filtrates were concentrated under reduced pressure. Crude product was purified by flash chromatography (20% ethyl acetate/hexanes on silica gel) and preparative TLC (20% ethyl acetate/hexanes on silica gel GF, 1000μ thickness) to give a white, crystalline film (134.5 mg, 0.5331 mmol, 27%) homogeneous to TLC (20% ethyl acetate/hexanes on silica gel, $R_f$ 0.39). (NA-1994A-307A)

Example 33

Estra-1,3,5(10),6,16-pentaen-3-yl acetate, 3.

A solution of estra-1,3,5(10),16-pentaen-3-ol(2, 97.9 mg, 0388 mmol) in anh. pyridine (1.3 mL, 16 mmol) and acetic anhydride (0.18 mL, 1.9 mmol) was stirred 24 h, after which ethyl acetate (15 mL) was added and the mixture washed with three 5 mL aliquots of 1 N hydrochloric acid +5 mL of saturated sodium bicarbonate +5 mL brine, dried over magnesium sulfate, and filtered through diatomaceous earth. See FIG. 15. The residue was washed with 5 mL of ethyl acetate and the combined filtrates were concentrated under reduced pressure. Preparative TLC (10% ethyl acetate/hexanes on silica gel GF, 1000μ thickness) of the residue gave a slightly yellow crystalline solid (74.9 mg, 0.254 mmol, 66%) homogeneous to TLC (10% ethyl acetate/hexanes on silica gel, $R_f$ 0.40). (NA-1994B-21B)

Example 34

Estra-1,3,5(10),7-tetraen-3-ol-17-(p-toluenesulfonyl) hydrazone, 4.

Equilin (500.1 mg, 1.863 mmol) and p-TsNHNH$_2$ (433.7 mg, 2.329 mmol) suspended in anh. methanol (5.0 mL) were refluxed 24 h with exclusion of moisture. See FIG. 15. After concentrating under reduced pressure the residual reaction mixture was flash chromatographed (35% ethyl acetate/hexanes on silica gel) to give a white foam (899.9 mg) representing >100% yield. (NA-1994A-246B)

Example 35

Estra-1,3,5(10),7,16-pentaen-3-ol, 5.

To a cooled (ice water bath) solution of crude estra-1,3,5(10),7-tetraen-3-ol,-17-(p-toluenesulfonyl) hydrazone (4, 899.9 mg, ≦1.863 mmol) in anh. THF (20 mL) under argon was added n-butyllithium (2.5 M in hexane, 3.0 mL, 7.5 mmol) dropwise with stirring over a period of 3 min. See FIG. 15. Stirring was continued 48 h, during which the reaction was allowed to gradually warm to room temperature. The reaction was poured into 50 mL of 1 N hydrochloric acid and the mixture was extracted with three 25 mL portions of ether. The combined organic extracts were washed with 50 mL of brine, dried over magnesium sulfate, and filtered through diatomaceous earth. The residue was washed with 10 mL of ether and the combined filtrates were concentrated under reduced pressure. The product was flashed chromatographed (20% ethyl acetate/hexanes on silica gel) and decolorized with carbon to give a yellow crystalline solid (274.8 mg, 1.089 mmol, 58%). (NA-1994A-278A)

Example 36

Estra-1,3,5(10),7,16-2-entaen-3-yl acetate, 6.

A solution of estra-1,3,5(10),7,16-pentaen-3-ol (5, 192.1 mg, 0.7612 mmol) in anh. pyridine (2.6 mL, 32 mmol) and acetic anhydride (0.36 mL, 3.8 mmol) was stirred 6 h, after which 30 mL of ethyl acetate were added. The mixture was washed with three 10 mL portions of 1 N hydrochloric acid +10 mL of saturated sodium bicarbonate +10 mL of brine, dried over magnesium sulfate, and filtered through diatomaceous earth. See Example 15. The residue was washed with 10 mL of ethyl acetate and the combined filtrates were concentrated under reduced pressure. Preparative TLC (5% ethyl acetate/hexanes on silica gel GF, 1000μ thickness) and recrystallization from aqueous ethanol gave fine white needles (78.6 mg, 0.267 mmol, 35%), m.p. 77–80° C. TLC (4% ethyl acetate/hexanes on silica gel) showed 2 spots at R$_f$ 0.21 and 0.24. (NA-1994A-286A)

Example 37

Estra-1,3,5(10),6,8-pentaen-3-ol-17-(p-toluenesulfonyl) hydrazone, 7.

Equilenin (0.6559 mg, 2.463 mmol) and pTsNHNH$_2$ (573.6 mg, 3.080 mmol) suspended in anh. methanol (8.2 mL) were refluxed 24 h with exclusion of moisture. See FIG. 16. After cooling and concentrating under reduced pressure the reaction mixture was flash chromatographed (35–40% ethyl acetate/hexanes 57%), m.p. 95–96° C. TLC (2% ethyl acetate/hexanes on silica gel) showed product (R$_f$ 0.1) contained a trace contaminant at the origin. (NA-1994A-273B)

Example 38

Estra-1,3,5(10),6,8,16-hexaen-3-ol, 8.

To a cooled (ice water bath) solution of crude estra-1,3,5(10)6,8-pentaen-3-ol 17-(p-toluenesuffonyl)hydrozne (7, 1.0887 g, ≦2463 mmol) in anh. THF (25 mL) under argon was added n-butyllithium (2.5 M in hexane, 3.9 mL, 9.8 mmol) dropwise with stirring over 2 min. See FIG. 16. Stirring was continued 3 days, during which the reaction was allowed to gradually warm to room temperature. 50 mL of 1 N hydrochloric acid-ice were added and the mixture was extracted three times with 25 mL portions of ether. The combined organic extracts were washed with 50 mL of brine, dried over magnesium sulfate, and filtered through diatomaceous earth. The residue was washed 10 mL of ether and the combined filtrates were concentrated under reduced pressure. Flash chromatography (20% ethyl acetate/hexanes on silica gel) and recrystallization from aqueous ethanol with charcoal decolorization gave tan platelets (245.8 mg, 0.9819 mmol, 40%), m.p. 162–163° C. (NA-1994A-269A)

Example 39

Estra-1,3,5(10),6,8,16-hexaen-3-yl acetate, 9.

A solution of estra-1,3,5(10),6,8,16-hexaen-3-ol Q8, 148.8 mg, 0.5944 mmol) in anh. pyridine (2.0 mL, 25 mmol) and acetic anhydride (0.28 mL, 3.0 mmol) was stirred 6 h, after which ethyl acetate (20 mL) was added. See FIG. 16. The mixture was washed with three 10 ML portions of 1 N hydrochloric acid +10 mL of saturated sodium bicarbonate +10 mL of brine, dried over sodium sulfate, and filtered. The residue was washed with 5 mL of ethyl acetate and the combined filtrates were concentrated under reduced pressure. Recrystallization from 95% ethanol gave lustrous white platelets (99.4 mg, 0.340 mmol, 55%, m.p. 95–96° C. TLC (2% ethyl acetate/hazanes on silica gel) showed product (R$_f$ 0.1) contained a trace contaminant at the origin.

Example 40

17-Methylenestra-1,3,5(10)-trien-3-ol, 10.

A suspension of methyltriphenylphosphonium bromide (100.03 g, 0.28001 mol) and potassium t-butoxide (31.42 g, 0.2800 mol) in anh. dimethylsulfoxide (DMSO, 320 mL) under argon was stirred in an oil bath (68–81° C.) 1 h, after which estrone (15.14 g, 55.99 mmol) in anh. DMSO (320 mL) was added via syringe. See FIG. 17. Stirring was continued 1 h and the reaction allowed to cool. The mixture was poured into 800 mL of ice-1 N hydrochloric acid and then extracted three times with 400 mL aliquots of ether. The combined organic extracts were washed with 350 mL of saturated sodium bicarbonate +400 mL of brine, dried over sodium sulfate, and flash filtered through a 58 mm high×84 mm dia. column of silica gel (200–40 mesh). Product continued eluting with additional ether.

Concentration of appropriate fractions under reduced pressure and three-fold recrystallization from aqueous ethanol gave very fine white needles (11.47 g, 42.73 mmol, 76%), m.p. 134–136° C., homogeneous to TLC (20% ethyl acetate/hexanes on silica gel, R$_f$ 0.45). (NA-1994A-242B)

Example 41

17-Methylenestra-1,3,5(10)-trien-3-yl acetate, 11.

A solution of 17-methylenestra-1,3,5(10)trien-3-ol (10, 5.84 g, 21.8 mmol) in anh. pyridine (32 mL, 0.40 mol) and acetic anhydride (9.7 mL, 0.10 mol) was stirred 24, after which ethyl acetate (250 mL) was added. See FIG. 17. The mixture was washed with three 100 mL portions of 1 N hydrochloric acid +100 mL of saturated sodium bicarbonate +100 mL of saturated copper sulfate +100 mL of brine, dried over magnesium sulfate, and filtered through diatomaceous earth. The residue was washed with 25 mL of ethyl acetate and the combined filtrates were concentrated under reduced pressure. Recrystallization from aqueous ethanol gave lustrous white platelets (5.84 g, 18.8 mmol), m.p. 77–79° C. (NA-1994A-248B)

Example 42

17-Methylenestra-1,3,5(10)-trien-6-on-3-yl acetate, 12.

To a suspension of chromium trioxide (6.19 g. 61.9 mmol) cooled to −8° C. (ice-salt bath) in methylene chloride (100 mL) was added 2,4-dimethylpyrazole (5.95 g, 61.9 mmol). See FIG. 17. After stirring 20 min., a solution of 17-methylenestra-1,3,5(10)-trien-3-yl acetate (11, 2.0001 g, 6.4428 mmol) in 10 mL of chilled methylene chloride was added over a period of 2 min. so that the temperature did not reach −6° C. Stirring was continued 2 h and the mixture was then passed through a column of 100 g of silica gel (200–400 mesh). Product continued eluting with further methylene chloride. Pooling and concentration of appropriate fractions under reduced pressure gave crude product, which was further purified by two-fold recrystallization from aqueous ethanol to give lustrous off-white crystals (334.0 mg, 1.030 mmol, 16%), m.p. 91–94° C. TLC (25% ethyl acetate/hexanes on silica gel) showed product ($R_f$ 0.47) with two minor contaminants at $R_f$ 0.30 and 0.39. (NA-1994A-272A)

Example 43

17-Methylenestra-1,3,5(10)-trien-3,6β-diol, 13.

To a suspension of lithium aluminum hydride (53.6 mg, 1.41 mmol) in anh. THF (3.0 mL) under argon cooled in a dry ice/acetone bath was added 17-methylenestra-1,3,5(10)-trien-6-on-3-yl acetate (12, 251.7 mg, 0.7758 mmol) in anh. THF (3.0 mL) dropwise with stirring over 8 min. See FIG. 17. After stirring 2 h, the bath was removed and stirring continued a further hour. The reaction was quenched by stirring ½ h with Glauber's salt (1.78 g). The resulting mixture was applied to a short pad of diatomaceous earth and extracted four times with 10 mL portions of ethyl acetate. Continued extraction with five 10 mL portions of hot ethyl acetate and concentration of all extracts under reduced pressure gave a colorless film. Preparative TLC (40% ethyl acetate/hexanes on silica gel GF, $^{1000}$IL thickness) gave a white foam (15.3 mg, 53.8 ILmol, 7%). TLC (40% ethyl acetate/hexanes on silica gel) showed major ($R_f$ 0.29) and minor components ($R_f$ 0.37). (NA-1994A-283B)

Example 44

17-Methylenestra-1,3,5(10)-trien-3-yl methyl ether, 14.

To a stirred suspension of 17-methylenestra-1,3,5(10)-trien-3-ol (5.37 g, 20.0 mmol) and potassium carbonate (50.82 g, 0.3678 mol) at reflux in 90% ethanol (500 mL) was added dimethyl sulfate (5.0 mL, 53 mmol). After ½ h reflux additional dimethyl sulfate (36 mL, 0.38 mol, in three 12 mL aliquots) was added over the period of 1 h. See FIG. 17. The reaction was refluxed a further hour, following which 360 mL of water were added and the mixture was placed in the refrigerator overnight. The resulting suspension was filtered and washed with 80 mL of 60% methanol +three 80 mL portions of 5% (w/w) sodium hydroxide +three 80 mL portions of water. The residue was recrystallized from aqueous methanol to give white crystals (3.88 g, 13.7 mmol, 69%), m.p. 59–62° C. TLC (20% ethyl acetate/hexanes on silica gel) showed product ($R_f$ 0.63) with trace contaminants at $R_f$ 0.37 and at the origin. (NA-1994A-247)

Example 45

17-Methylenestra-2,5(10)-dien-3-yl methyl ether, 15.

Approximately 70 mL of anh. ammonia was distilled through a KOH tower into a 250 mL flame-dried 3-neck flask fitted with an inlet adapter, magnetic stirring bar, dry ice/acetone condenser, and ground glass stopper. See FIG. 17. A solution of 17-methylenestra-1,3,5(10)-trien-3-yl methyl ether (14, 1.1297 g, 4.0001 mmol) and t-butyl alcohol (13.21 g, 0.1782 mol) in dry THF (17 mL) was added, followed by lithium wire (0.47 g, 68 mg-atom) cut in small pieces. After refluxing under argon for 6 h anh. methanol (6.6 mL) was added and the suspension was stirred overnight while allowing ammonia to boil off. Water (100 mL) was added and the suspension was extracted three times with 50 mL portions of methylene chloride. The combined organic extracts were washed with 100 mL of brine, dried over sodium sulfate, and filtered. The residue was washed with 25 mL of methylene chloride and the combined filtrates were concentrated under reduced pressure. The resulting light yellow oil was crystallized from aqueous ethanol to give lustrous white crystals (815.0 mg, 2.865 mmol, 72%), m.p. 77–78° C., homogeneous to TLC ($R_f$ 0.60, 10% ethyl acetate/hexanes on silica gel). (NA-1994A-257)

Example 46

17-Methylenestr-4-en-3-one, 16:

Con. hydrochloric acid (6.0 mL) and water (6.0 mL) were added to a solution of 17-methylenestra-2,5(10)-dien-3-yl methyl ether (15, 702.8 mg. 2.471 mmol) in methanol (6 mL) and acetone (20 mL). See Example 17. After stirring 1 h, sodium bicarbonate (7.50 g) was added cautiously. The mixture was concentrated under reduced pressure once effervescence had ceased and water (50 mL) was added. The mixture was extracted three times with 25 mL portions of methylene chloride. The combined organic extracts were washed with 50 mL of brine, dried over magnesium sulfate, and filtered through diatomaceous earth. The residue was washed with 10 mL of methylene chloride and the combined filtrates were concentrated under reduced pressure. The product was purified by decolorization with charcoal, flash chromatography (20% ethyl acetate/hexanes on silica gel), and recrystallization from aqueous ethanol to give a white powder (302.8 mg. 1.120 mmol, 45%), m.p. 83–89° C. (NA-1994A-271)

Example 47

17-Methylenestr-4-en-3β-ol, 17.

Lithium tri-t-butoxyaluminohydride (766.6 mg, 3.015 mmol) was added to a solution of 17-methylenestr-4-en-3-one (16, 203.7 mg, 0.7533 mmol) in 10 mL of anh. ether and the reaction was stirred 4 h. See FIG. 18. Glauber's salt (3.80 g) was added and the suspension was stirred an additional ½ h. The mixture was filtered through diatomaceous earth and the residue was washed five times with 10 mL portions of ether. The combined filtrates were concentrated under reduced pressure and then subjected to preparative TLC (5% ethyl acetate/methylene chloride on silica gel GF, 1000μ thickness) to give white needles (60.2 mg. 0.221 mmol, 29%) homogeneous to TLC (Rf 0.37, 5% ethyl acetate/methylene chloride on silica gel). (NA-1994A-282)

Example 48

17-Methylenestra-1,3,5(10),7-tetraen-3-ol, 18.

Methyltriphenylphosphonium bromide (1.9967 g, 5.5892 mmol) and potassium t-butoxide (627.2 mg, 5.589 mmol) suspended in 6.1 mL of anh. DMSO under argon were 1 h in an oil bath (71–83° C., after which equilin (300.0 mg, 1.118 mmol) in 6.1 mL of anh. DMSO was added via syringe. See FIG. 18. After stirring a further 70 min., the reaction mixture was poured into 40 mL of ice water and extracted three times with 25 mL portions of ether. The combined organic extracts were washed with 25 mL of brine, dried over magnesium sulfate, and filtered through diatomaceous earth. The residue was washed with 10 mL of ether and the combined filtrates were concentrated under reduced pressure. Flash chromatography (15% ethyl acetate/hexanes on silica gel) followed by preparative TLC (20% ethyl acetate/hexanes on silica gel GF, 1000μ thickness) gave an opaque white film (162.3 mg, 0.6093 mmol, 54%). (NA)-1994A-258)

Example 49

17-Methylenestra-1,3,5(10),7-tetraen-3-yl acetate, 19.

Methyltriphenylphosphonium bromide (3.33 g, 9.32 mmol) and potassium t-butoxide (1.05 g, 9.36 mmol) suspended in 10 mL of anh. DMSO under argon was stirred 1 h in an oil bath (77–79° C.), following which equiilin (500.0 mg, 1.863 mmol) in 10 mL of anh. DMSO was added via syringe. See FIG. 18. After stirring a further hour the cooled reaction mixture was poured into 50 mL of ice-1 N hydrochloric acid and extracted three times with 25 mL portions of ether. The combined organic extracts were washed with 25 mL of brine, dried over magnesium sulfate, and filtered through diatomaceous earth. The residue was washed with 10 mL of ether and combined filtrates concentrated under reduced pressure. The resulting light yellow syrup was taken up in anh. pyridine (6.3 mL, 78 mmol), acetic anhydride was added (0.88 mL, 9.3 mmol), and the reaction mixture was stirred 16 h.

The mixture was then poured into 100 mL of 1 N hydrochloric acid and extracted three times with 50 mL portions of ether. The combined organic extracts were washed with 100 mL of saturated sodium bicarbonate +100 mL of brine, dried over magnesium sulfate, and filtered through diatomaceous earth.

The residue was washed with 25 mL of ether and the combined filtrates were concentrated under reduced pressure. The crude acetate was flash chromatographed (5% ethyl acetate/hexanes on silica gel) to give a yellow resin (494.7 mg, 1,604 mmol, 86%). (NA-1994A-305)

Example 50

Estra-4,16-dien-10β-ol-3-one, 2.

To a frozen (dry ice/acetone) suspension of estra-5(10), 16-dien-3-one (1, 115.7 mg, 0.4513 mol) in chloroform (3 mL) was added m-chloroperbenzoic acid (MCPBA, 77.4%, 420.8 mg, 1.89 mEquiv. of peracid) suspended in ether (4.3 mL) and the mixture was stirred 2 h. See FIG. 19. The reaction was then stored in a refrigerator for 18 h, after which sodium thiosulfate pentahydrate [5% (w/w), 25 g] was added. After stirring 5 min., the mixture was extracted three times with 10 mL portions of ether. The combined organic extracts were washed with 25 mL of saturated sodium bicarbonate +25 mL of brine, dried over magnesium sulfate, and filtered through diatomaceous earth. The residue was washed with 10 mL of ether and the combined filtrates were concentrated under reduced pressure. TLC suggested the intermediate 5B,10β-epoxide had undergone partial elimination. Elimination was completed by refluxing the white crystalline residue for 1 h in 20 g of 5% (w/w) potassium hydroxide in anh. methanol. The reaction mixture was poured into 50 mL of ice water and extracted with 50 mL of ether. The organic extract was washed twice with 50 mL portions of water, dried over sodium sulfate, and filtered through diatomaceous earth. The residue was washed with 20 mL of ether and the combined filtrates were concentrated under reduced pressure. The residue was subjected to preparative TLC (50% ethyl acetate/hexanes on silica gel GF, 1000μ thickness) to give a colorless resin (19.7 mg, 72.3μ mol, 16%). (NA-1993B-80)

Example 51

18-Nor-17-methylestra-4,13(17)-dien-3-ol, 4.

To a cooled (ice water bath) solution of 18-nor-17-methylestra-4,13(17)-dien-3-one (3, 0.23 g, 0.90 mmol) in anh. methanol (2.3 mL) was added sodium borohydride (0.23 g, 6.1 mmol) and the reaction was stirred for 2 h. See FIG. 19. Solvent was removed under reduced pressure and 10 mL of water were added to the residue. The mixture was then extracted three times with 10 mL portions of methylene chloride. The combined organic extracts were washed with 10 mL of brine, dried over magnesium sulfate, and filtered through diatomaceous earth. The residue was washed twice with 5 mL of methylene chloride and the combined filtrates were concentrated under reduced pressure. The resulting slightly yellow solid was purified by preparative TLC (5% ethyl acetate/methylene chloride on silica gel GF, 1000μ thickness) to give a yellow solid (53.6 mg, 0.207 mmol, 23%) homogeneous to TLC (5% ethyl acetate/methylene chloride on silica gel; $R_f$ 0.32). (NA-1993B-120)

Example 52

Electrophysiology of Estrene Stimulation of the Human VNO and Olfactory Epithelium.

A non-invasive method has been employed to record local electrical potentials from the human vomeronasal organ (VNO) and from the olfactory epithelium (OE). Localized gaseous stimulation was applied to both nasal structures at different instances using specially designed catheter/electrodes connected to a multichannel drug delivery system. The local response of the VNO and the OE showed a correlation with the concentration of the ligand stimulus.

The study was performed on ten clinically normal (screened) volunteers—2 males and 8 females, ranging in age from 18 to 85 years. The studies were conducted without general or local anesthetics.

The catheter/electrodes were designed to deliver a localized stimulus and simultaneously record the response. In the case of VNO recording, the right nasal fosa of the subject was explored using a nasoscope (nasal specula) and the vomeronasal opening was localized close to the intersection of the anterior edge of the vomer and the nasal floor. The catheter/electrode was gently driven through the VNO-opening and the electrode tip placed in the organ's lumen at 1 to 3 mm from the opening. The nasoscope was then removed. In the case of the OE, recording the procedure was similar except the positioning of the catheter/electrode was gently placed deep in the lateral part of the medial nasal duct, reaching the olfactory mucosa.

Localized gaseous stimulation was done through the catheter/electrode. A constant stream of clean, nonodorous, humidified air at room temperature was continuously passed through a channel of the stimulating system. The stimulating ligand substances were diluted in propylene glycol, mixed with the humidified air, and puffed for from 1 to 2 seconds through the catheter/electrode. It is estimated that this administration provides about 25 pg of steroid-ligand to the nasal cavity.

Figure 2A:
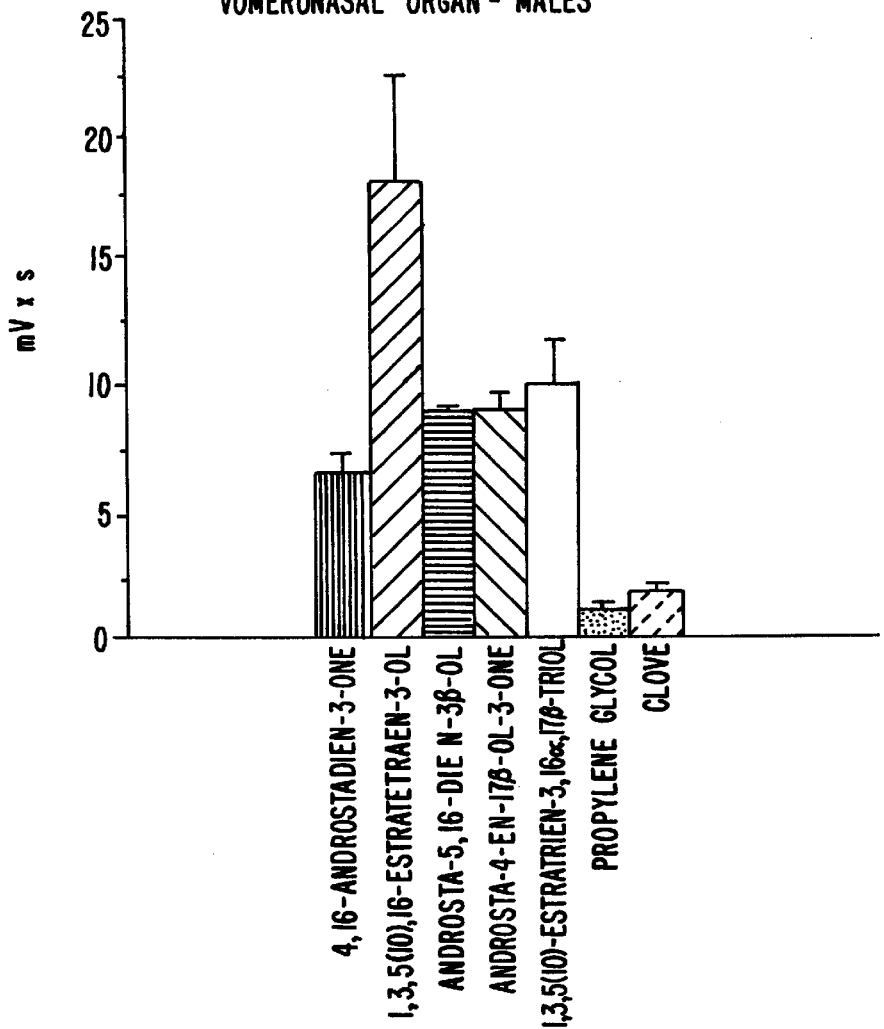
FIGS. 2A, 2B, and 2C are graphic representations of the electrophysiological effect on receptor potential of the localized administration of particular steroids to the vomeronasal organ of male subjects (FIG. 2A) and to the olfactory epithelium (FIG. 2C).
Figures 1, 2B:
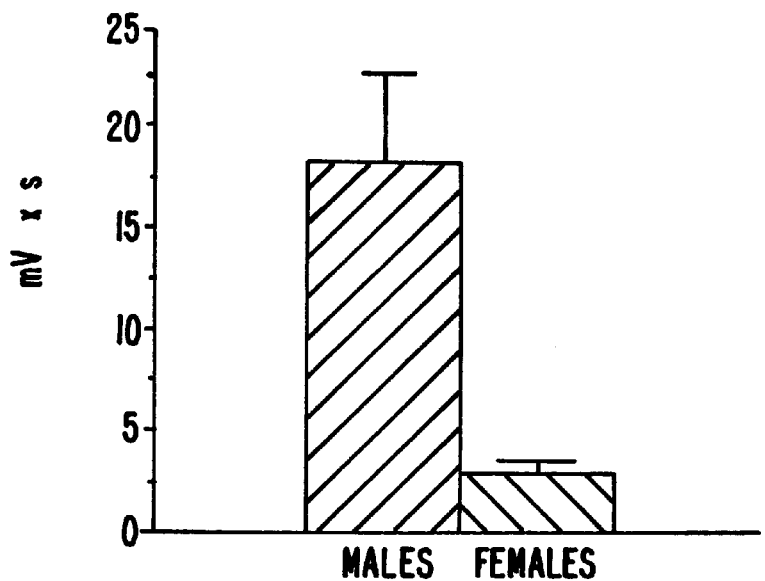
Figures 2, 2B:
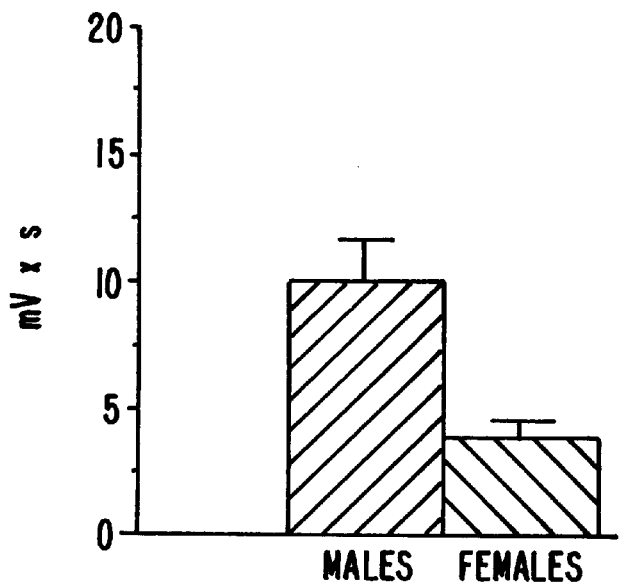

The results of this study are presented in FIG. 2. The response is measured in millivolt-seconds (mV×s). 1,3,5

Figure 2C:
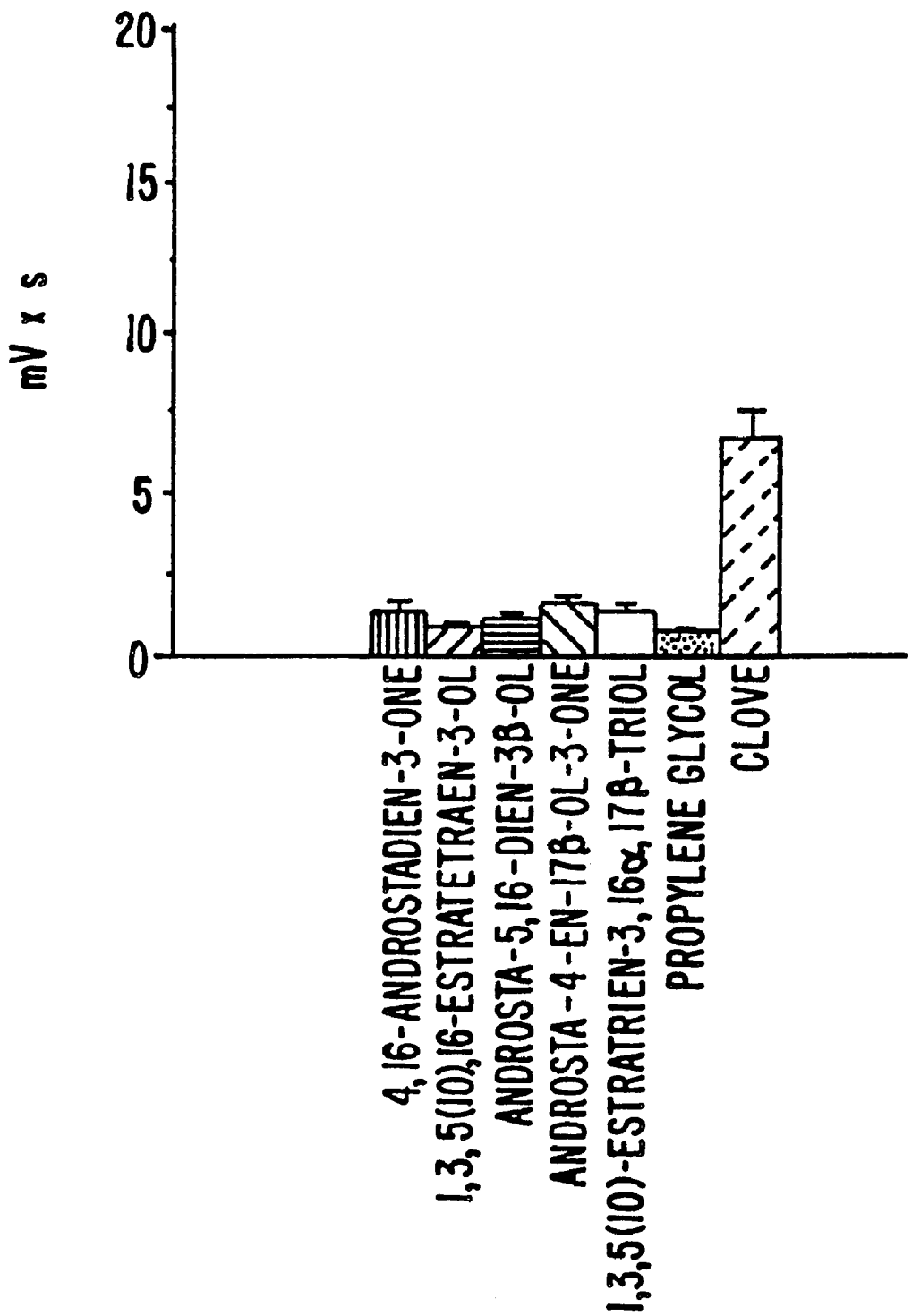

(10),16-Estratetraen-3-ol elicits a significantly stronger VNO response in males than do the other compounds tested (FIG. 2A). 1,3,5(10)-Estratrien-3, 16α,17β-triol also elicits a strong VNO response. Furthermore, the VNO response to these two Estrenes is sexually dimorphic approximately four times as strong in males as it is in females (FIG. 2B). In contrast, the OE response in both males and females is low compared to a strong odorant such as clove (FIG. 2C).

Example 53

Measurement of the Change in Receptor Potential of the Neuroepithelium of the VNO in Response to Various steroids.

Figure 3A:
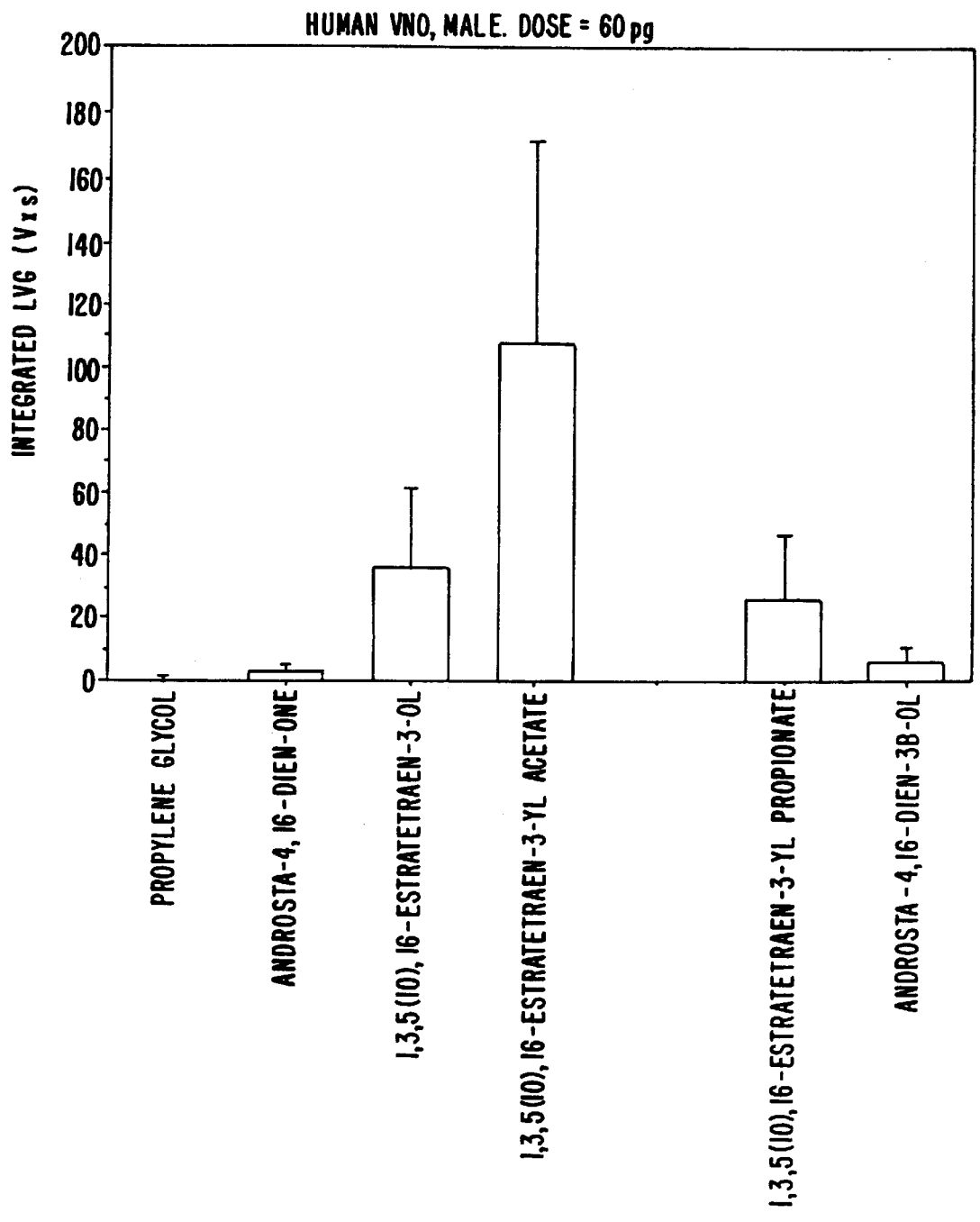
FIG. 3 is a graphic representation of the electrophysiological effect of the localized administration of particular steroids to the vomeronasal organ of male (3A) and female (3B) subjects.
Figure 3B:
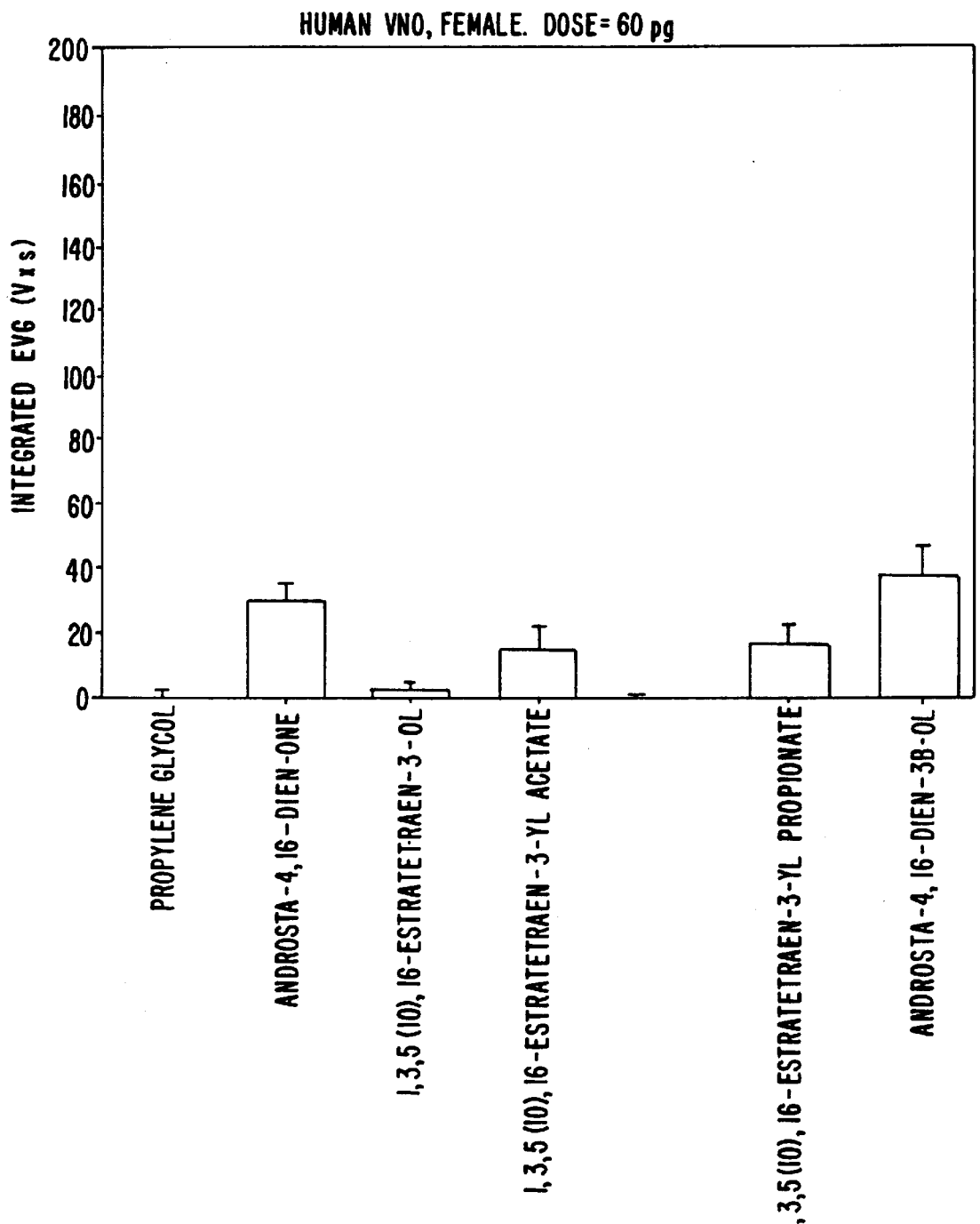

The change in receptor potential in response to seven different ligands was measured in 40 female (FIG. 3A) and 40 male (FIG. 3B) subjects. Each subject was administered 60 pg of each of seven substances as indicated in the Figures. The substances were administered, each separately for 1 second, using the procedure described in Example 20. The change in potential of the neuroepithelium of VNO was recorded over time and the integral of the change in potential for each of the forty subjects was averaged. The results are shown in the figure. Comparison of FIGS. 3A and 3B show that each steroid is sexually dimorphic in its activity and that some ligand substances are stronger in males while others are stronger in females.

Example 54

Measurement of Autonomic Responses to Estrene Stimulation of the VNO.

Figure 4A:
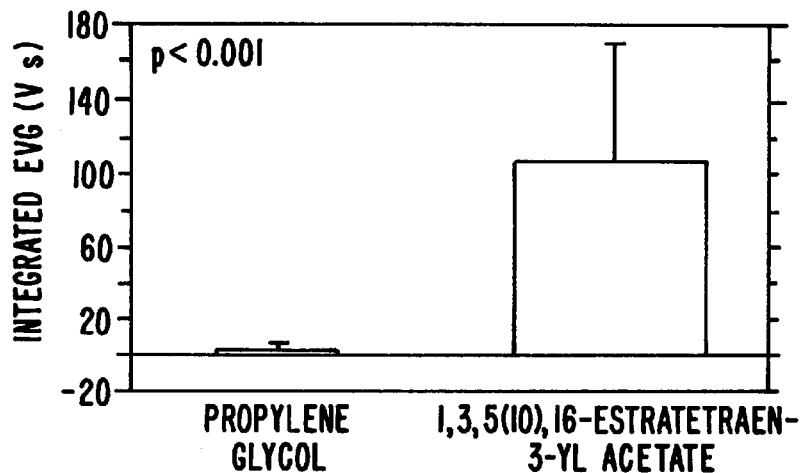
FIG. 4 depicts various autonomic responses of male subjects to 1,3,5(10), 16-Estratetraen-3-yl cetate. A=receptor potential of the vomeronasal euroepithelium; B=change in galvanic skin response (K-ohms); C=change in skin temperature (degrees C.).
Figure 4B:
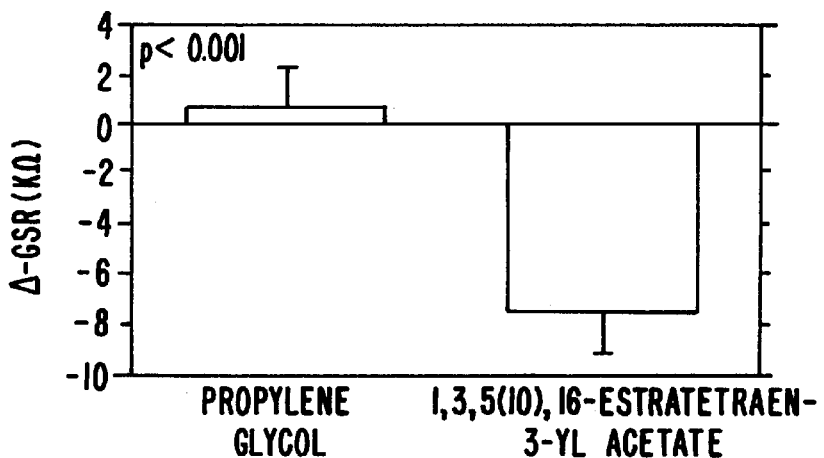
Figure 4C:
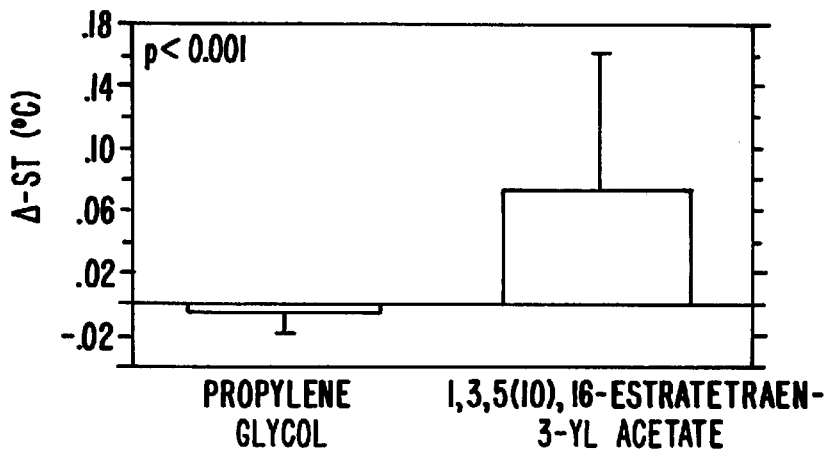

Various autonomic parameters were monitored while 1,3,5(10), 16-Estratetraen-3-yl-acetate was administered to 40 male subjects using the procedure described in Example 20. Propylene glycol was also administered as a control. The ligand was administered as a 1 second pulse. The change in autonomic function was first noted within 2 seconds and lasted for up to 45 seconds. As shown in FIG. 4, when compared to a propylene glycol control, the Estrene, induced a significant change in the integrated receptor potential in the VNO (4A), galvanic skin response (4B), and skin temperature (4C).

Example 55

Comparison of the Chance in Receptor Potential Induced by Two Estrene Steroids.

Figure 5:
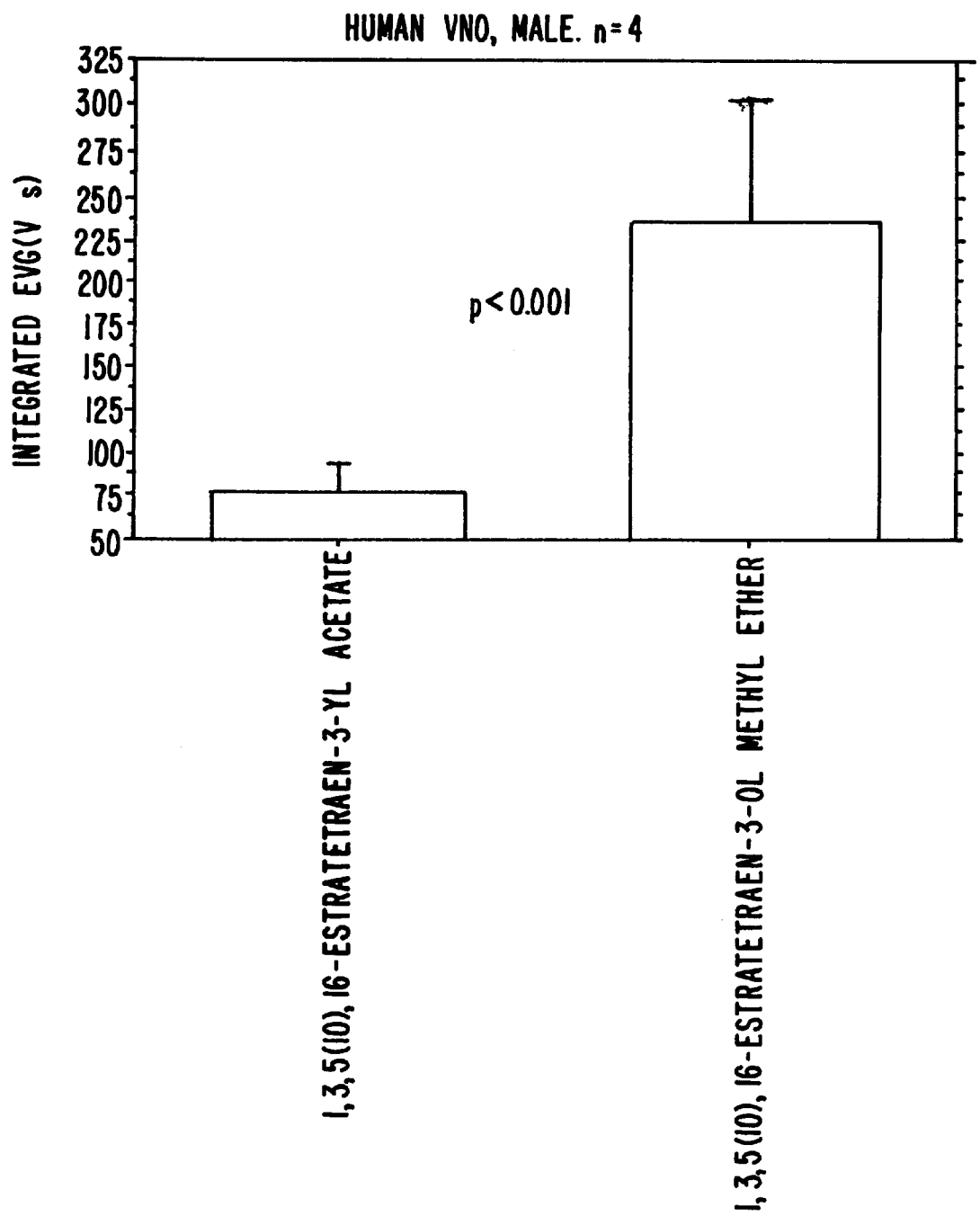
FIG. 5 depicts comparative changes in potential of the VNO after exposure to the methyl ether and the acetate of 1,3,5(10),16-Estratetraen-3-ol.

60 picograms of each steroid and of a propylene glycol control were administered to a male subject as described in Example 21. As shown in FIG. 5, 1,3,5(10),16-Estratetraen-3-ol methyl ether induced a greater change in receptor potential than did 1,3,5(10),16-Estratetraen-3-yl acetate.

Example 56

Psychophysiological Effect of Estrene Stimulation of the VNO.

The psychophysiological effect of Estrene stimulation of the VNO is measured by the coordinate administration of pheromone and questionnaire evaluation of the subject before and after administration. The questionnaire includes a panel of adjectives used as part of the standard Derogatis Sexual Inventory evaluation.

40 subjects, all in good health, are randomly assigned—20 exposed to placebo and 20 exposed to about 20 picograms of 1,3,5(10),16-Estratetraen-3-ol, administered as described in Example 3, supra. Subjects are given a 70 item questionnaire evaluating feeling states immediately before and 30 minutes after administration of either placebo or experimental substance. The 70 adjectives of the questionnaire are randomly administered and subsequently clustered for evaluation based on their relevance to each mood, feeling, or character trait.

Example 57

Electrophysiological Studies

The following electrophysiological studies were performed in 60 clinically normal human volunteers of both sexes (30 male and 30 female) whose ages ranged from 20 to 45 years. No anesthetics were used, and female subjects were excluded if pregnant.

The stimulation and recording system consists of a "multifunctional miniprobe" described elsewhere (Monti-Bloch, L. and Grosser, B. l. (1991) "Effect of putative pheromones on the electrical activity of the human vomeronasal organ and olfactory epithelium," *J. Steroid Biochem. Molec. Biol.* 39:573–582.). The recording electrode is a 0.3 mm silver ball attached to a small (0.1 mm) silver wire insulated with Teflon© the surface of the electrode is first treated to produce a silver chloride interface, and is then covered with gelatin It is positioned within a small caliber Teflon© catheter (dia=5 mm) such that the tip of the electrode protrudes approximately 2 mm. The Teflon© catheter is 10 cm in length and constitutes the terminal extension for a multichannel delivery system which delivers a continuous air stream carrying discreet pulses of chemosensory stimuli. The air stream first passes into a small chamber and is bubbled through a solution containing either a vomeropherin or an olfactant in a diluent or the diluent alone. A solenoid is used to rapidly redirect the air stream from the chamber to a route which bypasses the chamber. This creates a discreet pulse of stimulant in the air stream. A second, outer Teflon© tube with a diameter of 2 mm surrounds the catheter-electrode assemblage, and its central end is connected to an aspirator that provides continuous suction of 3 ml/s. This concentric arrangement of the outer suction tube allows the emitted chemosensory stimuli to be localized to an area we call a "minifield" (approx. dia=1 mm), and it avoids diffusion of substances either to the area outside the intended stimulation site or into the respiratory system. The entire stimulating and recording assemblage may be positioned either on the neurosensory epithelium within the VNO, or on the surface of the olfactory or respiratory epithelium.

Electro-vomeronasogram (EVG): Recordings are carried out in a quiet room with the subject supine; the multifunctional miniprobe is initially stabilized within the nasal cavity using a nasal retractor placed in the vestibule. Reference and ground electrodes consist of silver discs (8 mm), both of which are positioned on the glabella.

The entrance to the VNO, or vomeronasal pit, is identified by first dilating the nasal aperture and vestibule. A 6× magnifying binocular loupe with halogen illumination is then used to introduce the tip of the Teflon© catheter and recording electrode assemblage into the VNO opening where it is stabilized at an approximate depth of 1 mm within the vomeronasal passage. Optimal placement of the recording electrode is signaled after testing for an adequate depolarization in response to a test substance.

Electrical signals from the recording electrode are fed to a DC amplifier after which they are digitized, computer monitored, and stored. The peak-to-peak amplitude of the signals is measured, and the area under the depolarization wave is integrated, while continuously monitoring the signal both on the computer screen and on a digital oscilloscope. Artifacts produced by respiratory movements are deleted by training the subjects to practice mouth breathing with velopharyngeal closure.

Chemosensory Stimulants: Olfactory test substances are cineole, and 1-carvone; vomeropherins are A, B, C, E and F. (Vomeropherins were supplied by Pherin Corporation, Menlo Park, Calif.), Samples of vomeropherins In concentration of 25–800 fmoles are delivered in the continuous air stream for durations from 300 milliseconds to 1 second. Usually, intervals of 3 to 5 minutes separated each series of short test pulses. All components of the lines carrying the test stimuli are made of Teflon©, glass or stainless steel and are carefully cleaned and sterilized before each use.

Electro-olfactgram (EOG): Olfactory recordings employed the same stimulating and recording multifunctional miniprobe as that used for the VNO. The tip was slowly introduced until the recording electrode touched the olfactory mucosa. Adequate placement was signaled by a depolarization in response to a pulse of the odorant test substance.

Cortical evoked activity was induced by VNO stimulation with vomeropherins, and olfactory stimulation with odorants delivered in 300 ms air pulses. It was recorded using standard electroencephalographic (EEG) electrodes placed at positions Cz-A1 and Tz-A1 of the international 10120 system; the ground electrode was placed on the mastoid process. Electrodermal activity (EDA) was recorded using standard 8 mm silver electrodes in contact with palmar skin of the medial and ring fingers respectively, through a conductive gel interface. Skin temperature (ST) was recorded by a small (1.0 mm) thermistor probe placed in the right ear lobe. Peripheral arterial pulse (PAP) was monitored with a plethysmograph attached to the tip of the index finger. Respiratory frequency (RF) was measured with an adjustable strain gauge placed around the lower thorax. All electrical signals were DC amplified, digitized (NP-100, Biopac Systems) and continuously monitored utilizing a computer.

Statistical Analysis: EVGs or EOGS, peak-to-peak changes and frequency changes of other parameters were measured and statistically analyzed. The significance of the results was determined by either using paired t-tests or analysis of variance (ANOVA).

Figure 6A:
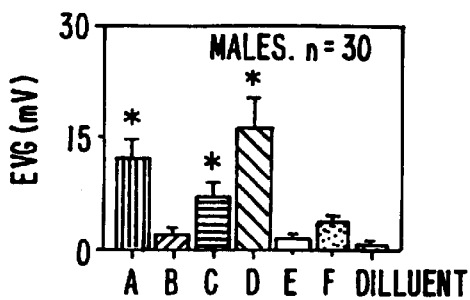
FIGS. 6A & B: EVG responses were measured as described in male (A) and female (B) subjects.
Figure 6C:
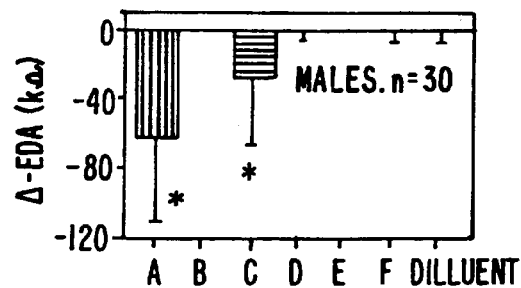
FIGS. 6C & D: Electrodermal activity was measured as described. Changes (measured in xΩ) in response due to delivery of vomeropherins to the VNO of each subject are shown in male (C) and female (D) subjects.
Figure 6B:
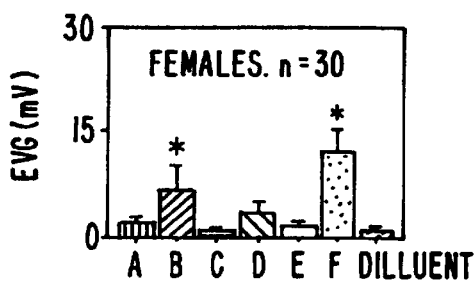
FIG. 6 depicts sexual dimorphism in local and autonomic responses to the stimulation of the VNO with vomeropherins. Various vomeropherins (200 fmoles) and the diluent control were administered to 30 male and 30 female subjects (ages 20 to 45) as described. Bars indicate the mean response of the population.
FIGS. 6E & F: Alpha-cortical activity was measured as described. Changes in response due to delivery of vomeropherins to the VNO of male (E) and female (F) subjects.
FIGS. 6G & H: Skin temperature (ST) was measured as described. Changes in response due to delivery of vomeropherins to the VNO of each subject are shown in male (G) and female (H) subjects.
Figure 6D:
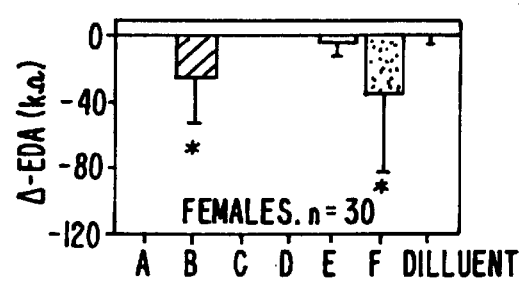
Figure 6E:
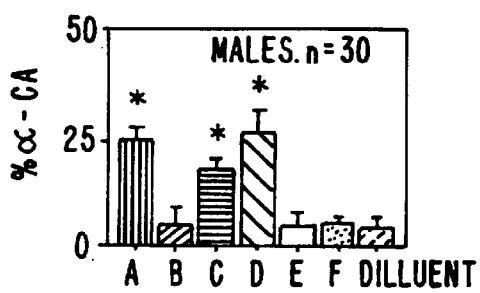

Effect of Vomeropherins on the EVG: Each of the vomeropherins was found to produce a sexually dimorphic receptor potential (FIGS. 6A–B). Recordings of the EVG were performed on 30 men and 30 women (ages 20 to 45). Vomeropherins were diluted and applied as 1 second pulses to the VNO with b minute intervals between pulses when questioned, the subjects were not able to "smell" or otherwise consciously detect any of the vomeropherins. This finding is in agreement with results previously reported (Nonti-Bloch, L. and Grosser, B. 1. (1991) "Effect of putative pheromones on the electrical activity of the human vomeronasal organ and olfactory epithelium," J. Steroid Biochem. Molec. Biol. 39:573–582.) which indicated that neither olfactory nor vomeropherin test stimuli delivered to the VNO elicit a perceptible sensation at the delivered concentration.

FIG. 6A shows the average response of male subjects (ages 20 to 38) to the diluent, and to equimolar quantities (100 fmoles) of five vomeropherins (A, B, C, D , and F), and to E, a stereoisomer of F. The profile of the response to each of the substances was similar in all subjects regardless of age, and no significant differences were revealed either by t-tests or by analysis of variance. For example, A, C and D produced significant effects ($M_{15}$=11.4 mV, SD=3.6 mV; $M_{76}$=6.4 mV, SD 2.5 mV, and $M_{84}$=15.1 mV, SD=4.9 mV; $p<0.01$), that were consistent in all individual cases. Other vomeropherins depolarized the VNO-receptors to a much lesser extent, but with consistent mean response amplitudes from individual to individual. Vomeropherins active in male subjects produced larger responses than the diluent ($p<0.001$). B, F and similar concentrations of olfactants induced significantly reduced responses in the male VNO (FIG. 6A and FIG. 7).

A similar experimental protocol was followed with the 30 female subjects (ages 20–45). Among the vomeropherins, F (100 fmoles) produced the most significant differences within the group (FIG. 6B). Here, A induced a small effect that was significantly different from F ($p<0.01$). In both populations of subjects, active vomeropherins induced receptor responses having large standard deviations (FIG. 6). When the frequency distribution of the effects of A and F was studied in males and females respectively, we found a bimodal distribution. The significance of this observation is being studied at this point.

E, a stereoisomer of F, does not stimulate the VNO in female subjects while F does (FIG. 6B). This is a demonstration of the specificity of VNO recognition of vomeropherins. In this regard it is interesting to note that while F is a superior vomeropherin, E generates a stronger olfactory effect than does F (FIG. 6B and FIG. 7).

Figure 7A:
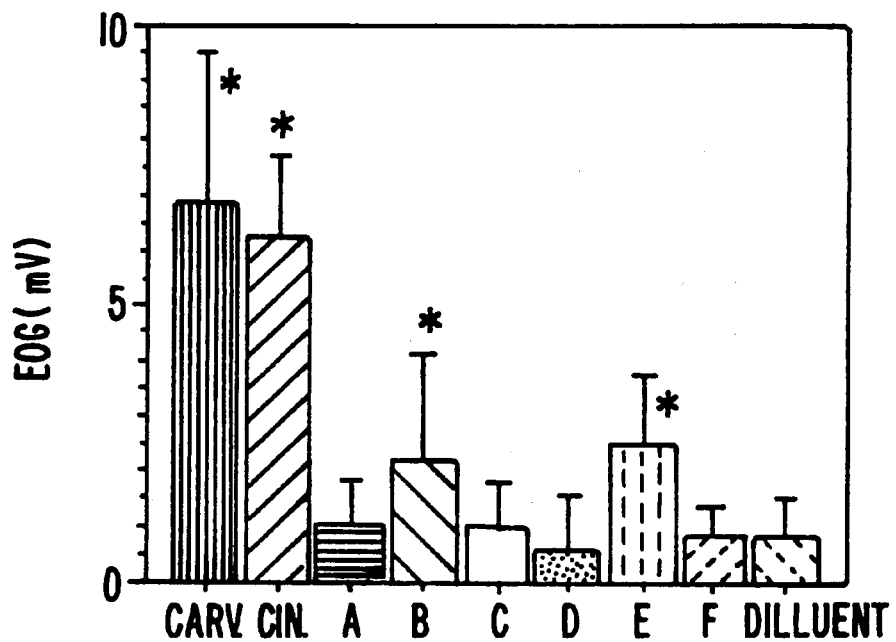
FIG. 7 depicts electro-olfactgrams of male and female subjects induced by stimulation of the OE with olfactants and vomeropherins A: 400 fmoles of the olfactants 1-carvone and cineole as well as 200 fmoles of the vomeropherins A, B, C, D and F; and the stereoisomer E were applied separately as one second pulses to the OE of 20 subjects (both male and female) and each EOG response was recorded as described. The olfactants as well as E and B produced significant (p<0.01) local response. B: 400 fmoles of the olfactants 1-carvone and cineole do not induce a significant EVG response when delivered to the VNO of male and female subjects.

Effects of Vomeropherins on the EOG: The summated receptor potential from the olfactory epithelium (OE) was recorded in 20 subjects: 10 males and 10 females. In contrast to the sensitivity of the VNO to vomeropherins, the OE is less sensitive to these substances. This is true for both males and females (FIG. 7A). The mean receptor potential amplitude ranged from 2.3 mV to 0.78 mV. In this study, B was the only vomeropherin having significant effect in the OE ($p<0.02$). Of the subjects questioned about odorant sensations following each stimulus presentation, 16 reported no olfactory sensation, while three males and one female described B as an unpleasant odor. This finding reveals that at the concentrations used in our study, most vomeropherins are not effective stimulants of the olfactory receptors, but do have a clear effect on vomeronasal receptors.

Figure 7B:
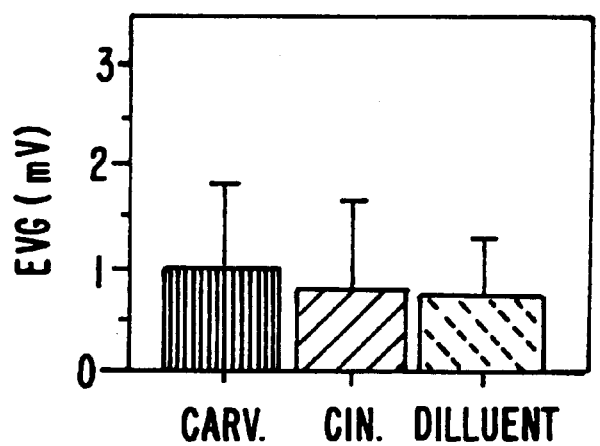
Figure 8A:
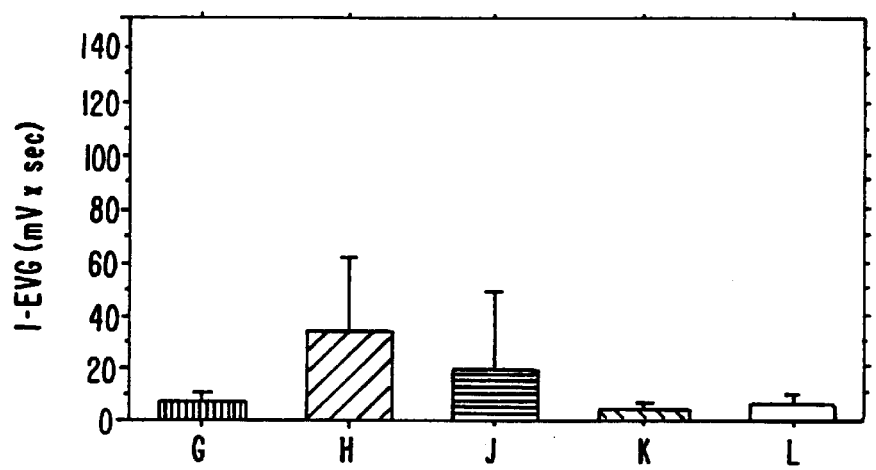
FIG. 8 depicts the electrophysiological effect of the following vomeropherins on the vomeronasal organ of 20 female subjects.
Figure 8B:
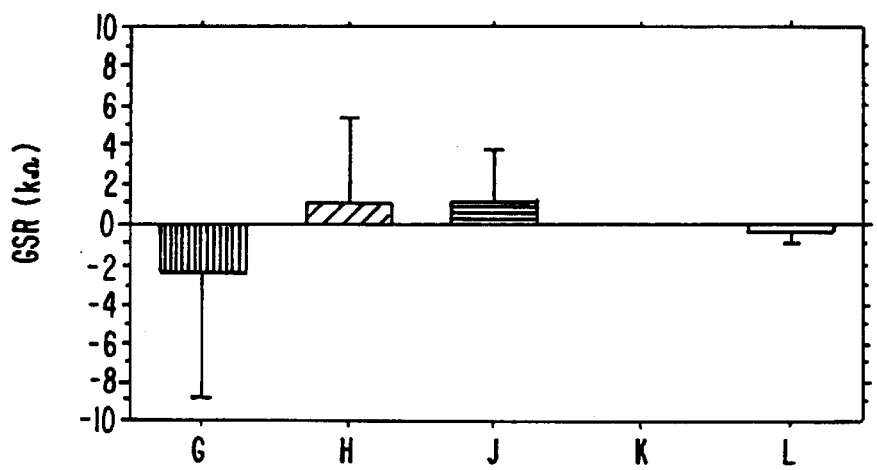
Figure 8C:
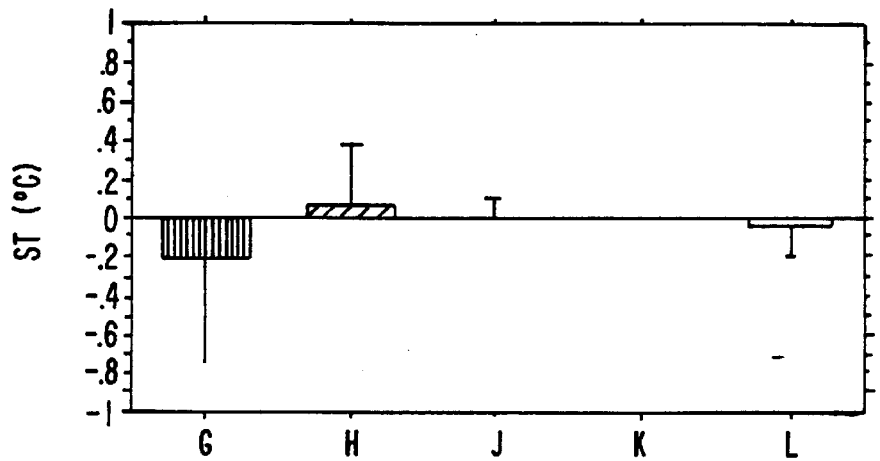
Figure 9A:
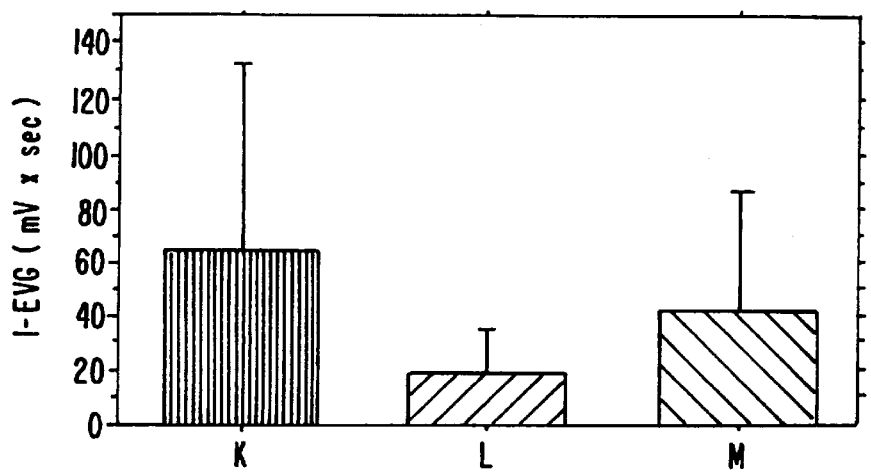
FIG. 9 depicts the electrophysiological effect of vomeropherins on the vomeronasal organ of 20 male subjects.
Figure 9B:
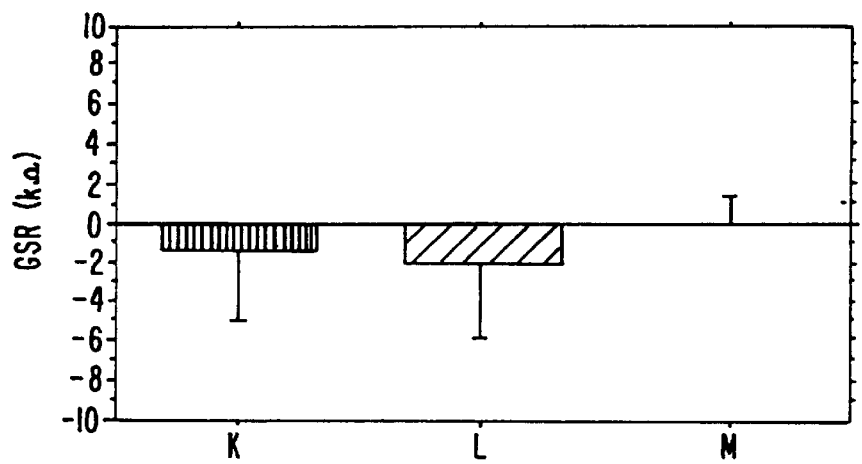
Figure 9C:
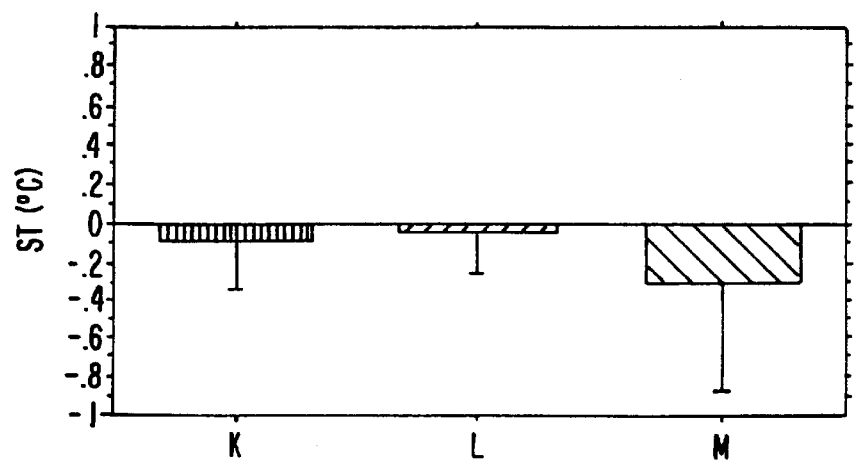

Effects of Olfactants on the EVG and EOG: In contrast to vomeropherins, the olfactants l-carvone and cineole produce only a minor local response in the VNO (FIG. 7B). This was true for both men and women. As expected, these olfactants produced a strong response in both men and women ($p<0.01$) when locally applied to the OE (FIG. 7A). The diluent depolarized olfactory receptors to a lesser extent than cineole or I-carvorn ($p<0.01$), and it did not produce an olfactory sensation.

Reflex Effects of Vomeropherins: Studies were conducted to determine the central nervous system (CNS) reflex responses to vomeropherin stimulation of the VNO. The sexually dimorphic local responses induced by vomeropherins (FIGS. 6A and B) were mirrored in the autonomic response of male & female subjects. In male subjects (FIG. 6C), A and C decreased skin resistance (electrodermal acuity EDA) ($p<0.01$, n=30). In female subjects. (FIG. 6B), F and B produced greater decrease in EDA than A or C ($p<0.01$, n=30).

Vomeropherins A and C induced a significant increase in skin temperature (ST) (FIG. 6G) in 30 male subjects ($p<0.01$); however D induced significant temperature decrease ($p<0.01$). In 30 female subjects (FIG. 6H) B and F evoked a significant increase in skin temperature (ST) ($p<0.01$) compared to A and C. In female subjects vomeropherins produced changes in EDA and ST with a greater standard deviation than in males.

Figure 6G:
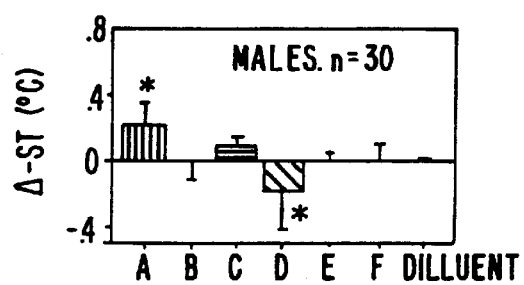
Figure 6F:
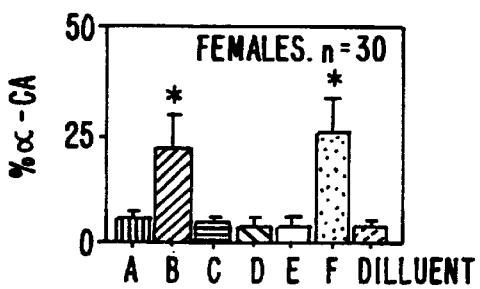
Figure 6H:
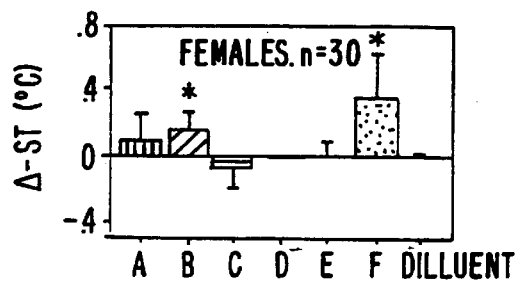

Cortical activity was recorded from Cz and Tz in male and female subjects during application to the VNO of air pulses (300 ms to 1 sec) containing 200 fmoles of vomeropherin (FIGS. 6G and H). In males (FIG. 6E) A, C and D significantly increased alpha cortical activity with a latency of 270–380 ms. D and A evoked the strongest effect (p<0.01). Synchronization of the EEG was sustained for 1.5 to 2.7 minutes after application of a single pulse of active substance. In females (FIG. 6F), a single pulse (200 fmoles) of B or F applied to the VNO increased alpha cortical independent of the response of olfactory receptors. We found characteristic specificities in the response of the human VNO and the olfactory epithelium which suggests that they are independent functional systems with separate connections to the CNS (Brookover, C. (1914) The nervus terminalis in adult man. J. Comp. Neurol. 24:131–135.) There is also preliminary evidence that the EVG is not associated with trigeminal nociceptor endings since application of a local anesthetic (2% lidocaine) to the respiratory epithelium of the nasal septum neither blocks nor diminishes the EVG (Monti-Bloch, L. and Grosser, B. 1. (1991) "Effect of putative pheromones on the electrical activity of the human vomeronasal organ and olfactory epithelium," *J. Steroid Biochem. Molec. Biol.* 39:573–582.), also, subjects failed to report sensations of pain as a consequence of any of the stimulation procedures.

Figure 31A:
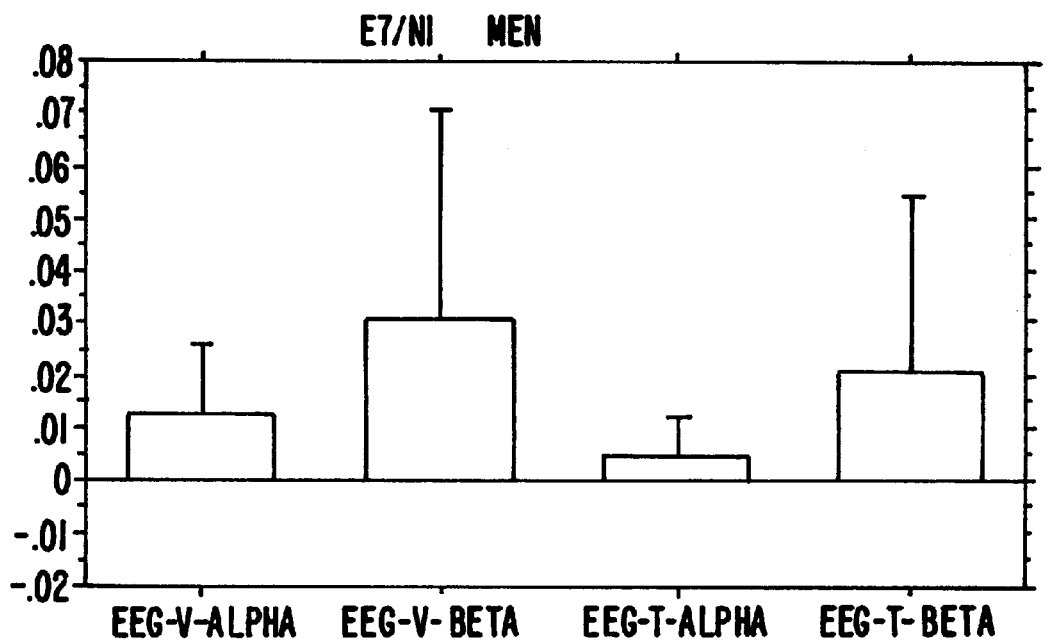
Figure 31B:
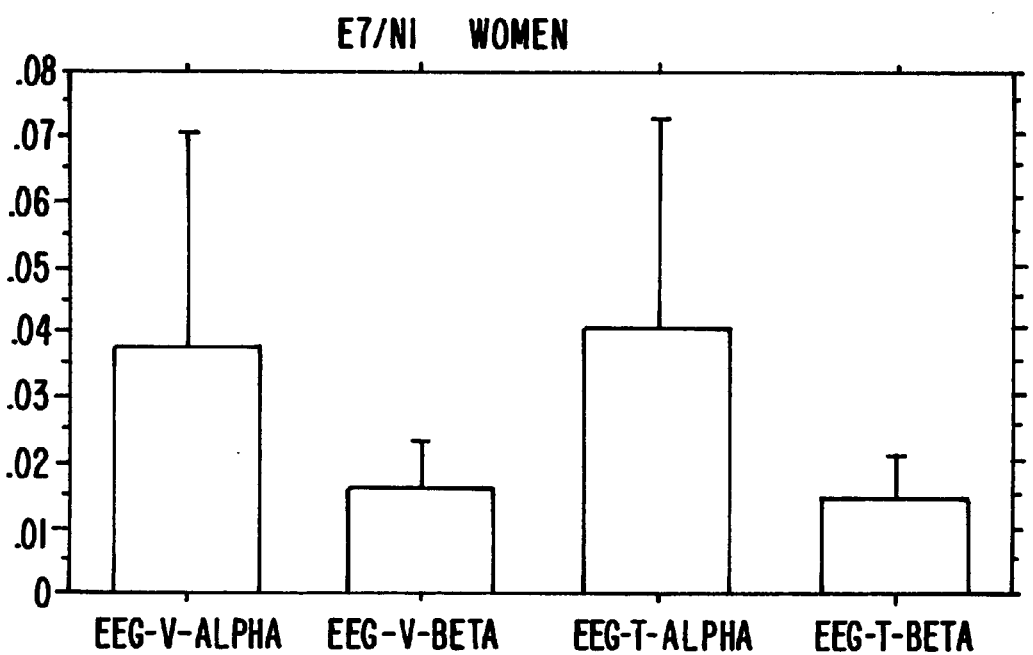
Figure 32A:
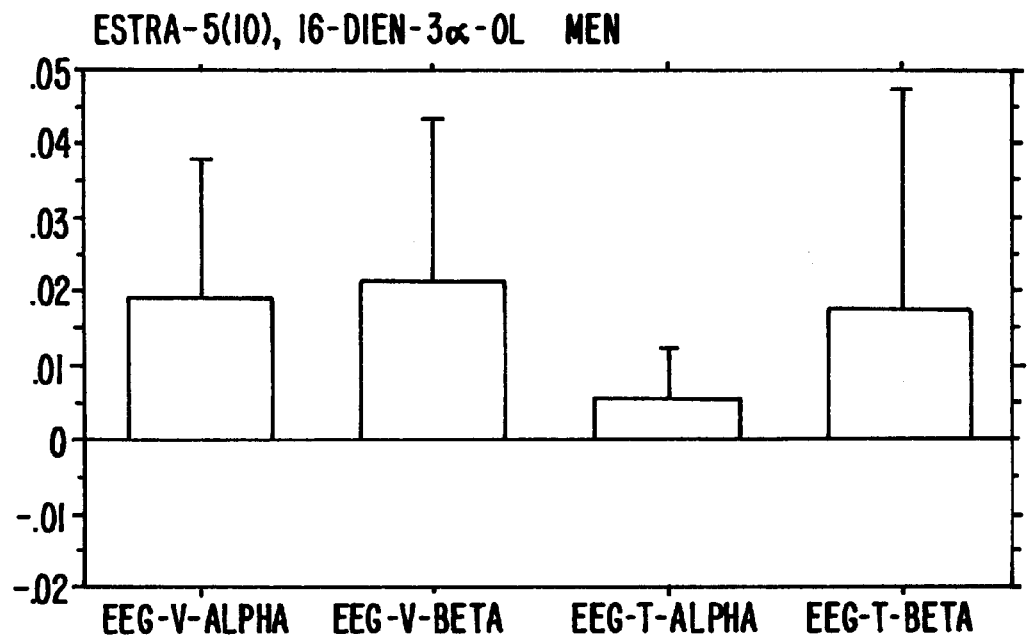
Figure 32B:
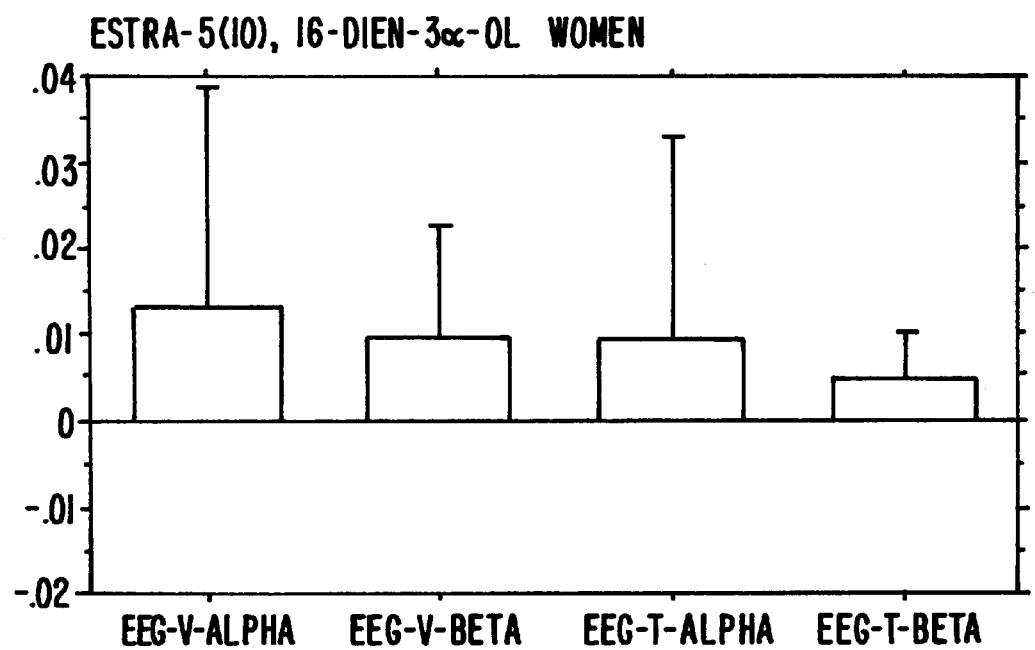
Figure 33A:
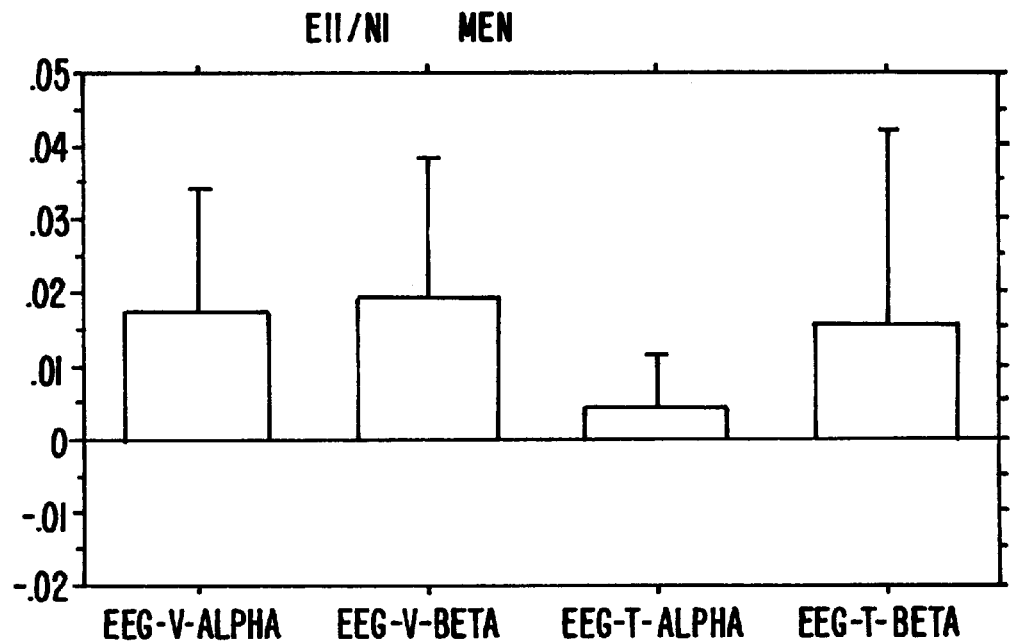
Figure 33B:
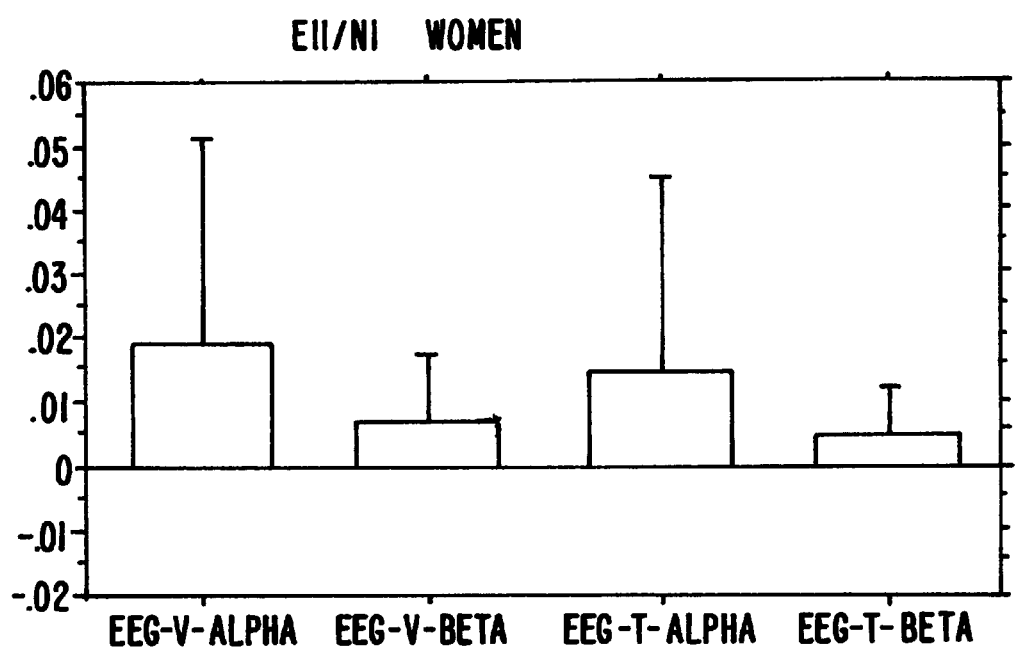
Figure 34A:
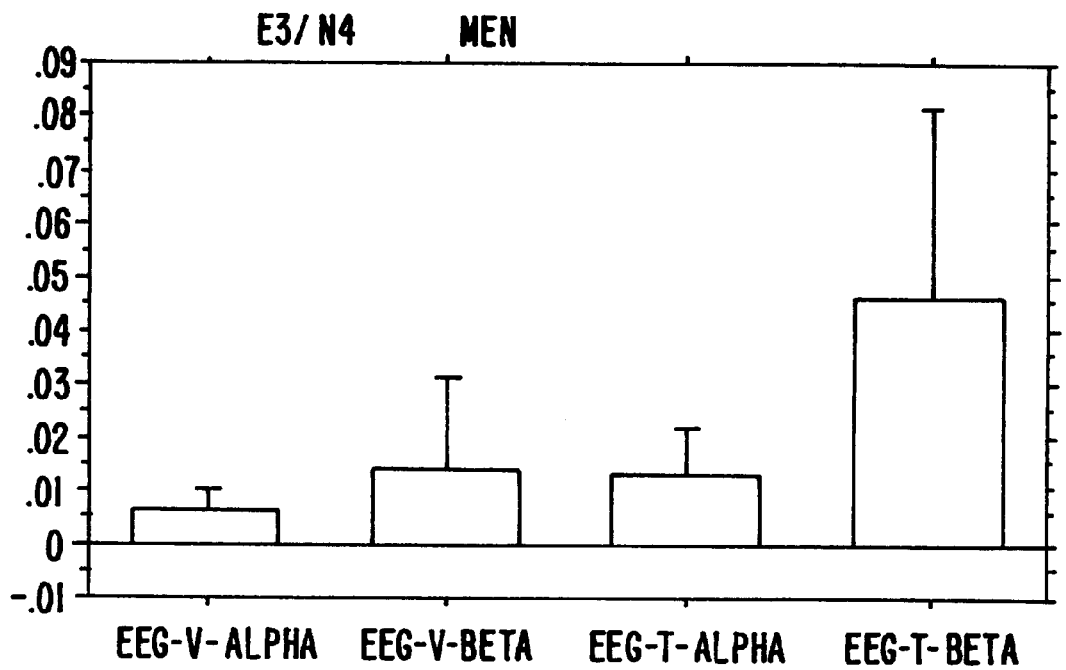
Figure 34B:
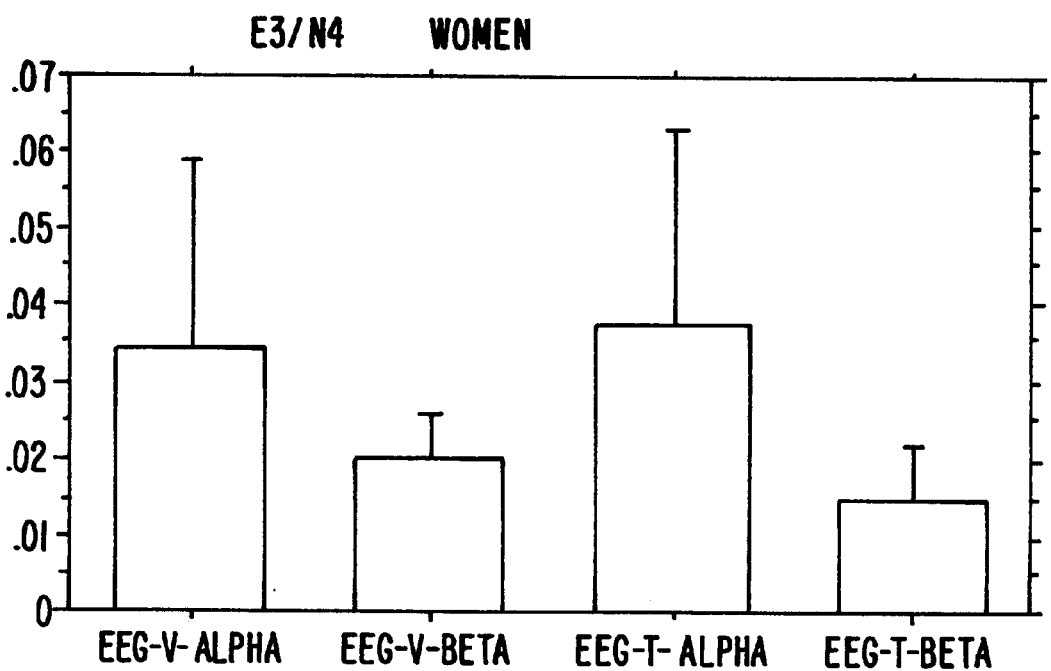

Additional EVG, GSR, ST and EEG tests were performed on 13 estranes in men and women identified in Chart 1 and FIG. 20. The steroid E12/N1 exhibited the best EEG-alpha activity in men. The steroid E8/N1 exhibited the best EEG-beta activity in men. The steroid E7/N1 exhibited the best EEG-alpha activity in women. Additionally, it is noted that E7/N1 exhibited excellent organ response, as shown by the EVG data, in both men (FIG. 21A) and women (FIG. 20A), but there were gender differences in the CNS (high EEG-alpha in women, high EEG-beta in men, FIGS. 31A and B).

VNO receptors are clearly more sensitive to vomeropherins than to any of the olfactants tested; the opposite is true for olfactory receptors. While the OE may have receptor sites for some vomeropherins, the response specificity of the VNO is clearly different.

Sexual differences were noted in the specificities and effects of two groups of vomeropherins, A, C and D; and B and F. This suggests a possible receptor-related sexual dimorphism. The findings suggest the activation of components of the autonomic nervous system In the adult human by vomeropherin stimulation of the VNO.

Furthermore, the results suggest that stimulation of the VNO with voneropherins produces synchronization of the EEG (FIGS. 6G and H) Thus, the evidence herein indicates that the vomeronasal system responds to a variety of chemosensory stimuli, and that some are able to induce reflex autonomic activity.

We claim:
1. A steroid compound of the formula:

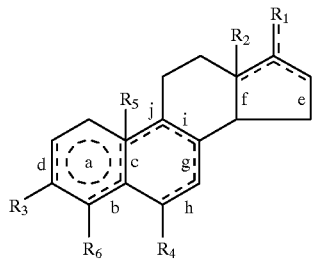

wherein $R_1$ is methyl; $R_2$ is absent or is hydrogen or methyl; $R_3$ is oxo, hydroxy, lower alkoxy, lower acyloxy, benzoyl, cypionyl, glucuronide or sulfonyl; $R_4$ is hydrogen, hydroxy, lower alkoxy, lower acyloxy, oxo or halo; $R_5$ is absent or is hydrogen, hydroxy, lower alkoxy or lower acyloxy; $R_6$ is a hydrogen or a halo; except that $R_4$ and $R_6$ are not simultaneously hydrogen; and "a" represents optional aromatic unsaturation of ring A of said steroid, or "b", "c", and "d" are each optional double bonds; and "e", "f", "g", "h", "i" and "j" are each optional double bonds; with the provisios that:
(I) when "a" is present, $R_3$ is hydroxy, and "j", "i", "g" and "h" are all absent, then (a) $R_4$ cannot be hydrogen; or (b) $R_4$ cannot be oxo if "e" and "f" are also absent;
(II) when "a", "h" and "i" are present, then (a) at least one of "e" or "f" is present;
(III) when "b" is present, $R_3$ is oxo, "g", "h", "i", "j" are all absent, $R_5$ is hydrogen, then f is absent;
(IV) when "b" and "j" are present and $R_3$ is oxo, then at least one of "e" or "f" must be present;
(V) when "c" is present, "d" is absent and $R_3$ is hydroxy, then at least "e" or "f" must be present;
(VI) when "c" and "d" are present and $R_3$ is methoxy, then at least "e" or "f" must be present;
(VII) when "b" is present, $R_3$ is hydroxy and $R_5$ is hydrogen, then at least "e" or "f" must be present.

2. A compound according to claim 1 wherein "a" is present and "g", "h" or "i" are optional double bonds.

3. A compound according to claim 1 wherein $R_2$ is methyl and "e" is a double bond.

4. A compound according to claim 1 wherein $R_4$ is hydroxy, lower alkoxy, lower acyloxy, oxo or halo.

5. A compound according to claim 1 wherein $R_5$ is hydrogen, hydroxy, lower alkoxy or lower acyloxy.

6. A compound according to claim 1 wherein $R_6$ is a halo.

7. A steroid compound of the formula:

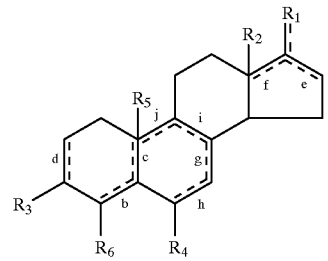

wherein $R_1$ is methyl; $R_2$ is absent or is hydrogen or methyl; $R_3$ is oxo, hydroxy, lower alkoxy, lower acyloxy, benzoyl, cypionyl, glucuronide or sulfonyl; $R_4$ is hydrogen, hydroxy, lower alkoxy, lower acyloxy, oxo or halo; $R_5$ is absent or is hydrogen, hydroxy, lower alkoxy or lower acyloxy; $R_6$ is a hydrogen or a halo; and "b", "c", and "d" are each optional double bonds; and "e", "f", "g", "h", "i" and "j" are each optional double bonds; with the provisios that:
(I) when "b" is present, $R_3$ is oxo, "g", "h", "i" "j" are all absent, $R_5$ is hydrogen, then f is absent;
(II) when "b" and "j" are present and $R_3$ is oxo, then at least one of "e" or "f" must be present;
(III) when "c" is present, "d" is absent and $R_3$ is hydroxy, then at least "e" or "f" must be present;
(IV) when "c" and "d" are present and $R_3$ is methoxy, then at least "e" or "f" must be present;
(V) when "b" is present, $R_3$ is hydroxy and $R_5$ is hydrogen, then at least "e" or "f" must be present;
(VI) when $R_2$ is absent; $R_4$, $R_5$, $R_6$ are all hydrogen; f is present, and a, b, c, d, g, h, i, j and e are all absent; then $R_3$ cannot be oxo;

(VII) when $R_2$ is methyl; $R_4$, $R_5$ and $R_6$ are hydrogen; e and b are present; a, d, c, h, g, i, j and f are absent; then $R_3$ cannot be oxo.

8. A compound according to claim 7 wherein "b" is a double bond.

9. A compound according to claim 7 wherein "c" and "d" are double bonds.

10. A steroid compound of the formula:

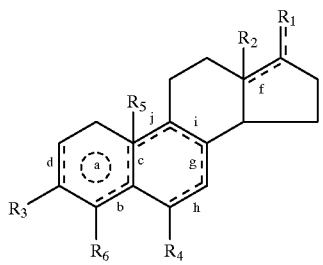

wherein $R_1$ is methyl; $R_2$ is absent or is hydrogen or methyl; $R_3$ is oxo, hydroxy, lower alkoxy, lower acyloxy, benzoyl, cypionyl, glucuronide or sulfonyl; $R_4$ is hydrogen, hydroxy, lower alkoxy, lower acyloxy, oxo or halo; $R_5$ is absent or is hydrogen, hydroxy, lower alkoxy or lower acyloxy; $R_6$ is a hydrogen or a halo; and "a" represents optional aromatic unsaturation of ring A of said steroid, or "b", "c", and "d" are each optional double bonds; with the proviso that when "f" is a double bond, one or both of "h" and "i" is a double bond; and "g" and "j" are each optional double bonds.

11. A steroid compound according to claim 10 wherein "h" is a double bond.

12. A steroid compound according to claim 10 wherein "i" is a double bond.

13. A steroid compound according to claim 11 wherein "i" is not a double bond.

14. The steroid 17-METHYLGONA-4,13(17)-DIEN-3β-OL.

* * * * *